United States Patent
Kodama et al.

(10) Patent No.: US 6,395,753 B1
(45) Date of Patent: May 28, 2002

(54) CYCLIC AMINE COMPOUNDS AND PHARMACEUTICAL COMPOSITION CONTAINING THE SAME

(75) Inventors: Tatsuhiko Kodama, Tokyo; Masahiro Tamura, Higashimurayama; Toshiaki Oda, Higashimurayama; Yukiyoshi Yamazaki, Higashimurayama; Masahiro Nishikawa, Higashimurayama; Shunji Takemura, Hachioji; Takeshi Doi, Higashimurayama; Yoshinori Kyotani, Higashiyamato; Masao Ohkuchi, Tokorozawa, all of (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/941,684

(22) Filed: Aug. 30, 2001

(51) Int. Cl.[7] ................ A61K 31/4545; C07D 401/06; C07D 401/14
(52) U.S. Cl. ............... 514/318; 546/194; 546/216; 546/223; 546/225; 546/256; 548/530; 548/541; 548/557; 514/333; 514/330; 514/329; 514/327; 514/423; 514/424
(58) Field of Search ................. 514/318, 333, 514/327, 329, 330, 423, 424, 426; 546/194, 256, 216, 223, 225; 548/530, 541, 557

(56) References Cited

FOREIGN PATENT DOCUMENTS

| | | | |
|---|---|---|---|
| JP | 9-143075 | 6/1997 | |
| JP | 10-67656 | 3/1998 | |
| JP | 10-147568 | 6/1998 | |
| JP | 10-182550 | 7/1998 | |
| JP | 11-92382 | 4/1999 | |
| JP | 2000-86641 | 3/2000 | |
| JP | 2000-509070 | 7/2000 | |
| JP | 2000-319277 | 11/2000 | |
| WO | 98/50534 | * 11/1998 | ................ 546/256 |
| WO | WO 01/14333 | 3/2001 | |

OTHER PUBLICATIONS

Yuichi Ohkawara, et al., In Situ Expression of the Cell Adhesion Molecules in Bronchial Tissues from asthmatics with Air Flow Limitation: In Vivo Evidence of VCAM–1/VLA–4 Interaction in Selective Eosinophil Infiltration, Am. J. Respir. Cell Mol. Biol. vol. 12, pp. 4–12, 1995.

Atsushi Sakai, et al., P–Selectin and Vascular Cell Adhesion Molecule–1 Are Focally Expressed in Aortas of Hypercholesterolemic Rabbits Before Initimal Accumulation of Macrophages and T Lymphocytes, Arteriosclerosis, Thrombosis, and Vascular Biology, vol. 17, No. 2, pp. 310–316, 1997.

Hisashi Wakita, et al., E–selectin and vascular cell adhesion molecule–1 as critical adhesion molecules for infiltration of T lymphocytes and eosinophils in atopic dermatitis, Journal of Cutaneous Pathology, vol. 21 pp. 33–39, 1994.

Takahiro Satoh, et al., Cyclophosphamide–induced blood and tissue eosinophilia in contact sensitivity: mechanism of hapten–induced eosinophil recruitment into the skin, Eur. J. Immunol vol. 27, pp. 85–91, 1997.

Paul P. Tak, et al., Expression of Adhesion Molecules in Early Rheumatoid Synovial Tissue, Clinical Immunology and Immunopathology, vol. 77, No. 3, pp. 236–242, 1995.*

Steven M. Albelda, et al., Adhesion molecules and inflammatory injury, The FASEB Journal, vol. 8, pp. 504–512, 1994.*

Timothy A. Springer, et al., TRAFFIC SIGNALS ON ENDOTHELIUM FOR LYMPHOCYTE RECIRCULATION AND LEUKOCYTE EMIGRATION, Annu. Rev. Physiol., vol. 57 pp. 827–872, 1995.*

(List continued on next page.)

Primary Examiner—Charanjit S. Aulakh
(74) Attorney, Agent, or Firm—Oblon, Spivak, McClelland, Maier & Neustadt, P.C.

(57) ABSTRACT

A cyclic amine compound represented by the following general formula (1):

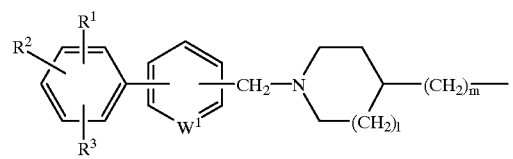

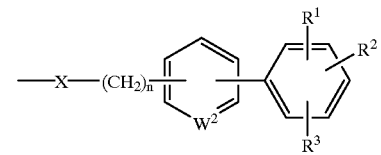

wherein, $R^1$, $R^2$ and $R^3$ each independently represent a hydrogen atom or an alkoxy group;

$W^1$ and $W^2$ each independently represent N or CH;

X represents O, $NR^4$, $CONR^4$ or $NR^4CO$;

$R^4$ each independently represents a hydrogen atom, or an alkyl, aryl, heteroaryl, aralkyl, or heteroaralkyl group; and l, m and n each represents a number of 0 or 1, a salt thereof and a hydrate thereof are provided.

These compounds have inhibitory effects on both cell adhesion and cell infiltration and are useful as anti-asthmatic agents, anti-allergic agents, anti-rheumatic agents, anti-arteriosclerotic agents, anti-inflammatory agents, anti-Sjogren's syndrome agents or the like.

18 Claims, No Drawings

OTHER PUBLICATIONS

S.A. Michie, et al., The Roles of 4–Integrins in the Development of Insulin–Dependent Diabetes Mellitus, Curr. Top. Microbiol. Immunol., vol. 231 pp. 65–83, 1998.*

Nobuyuki Ebihara, et al., Anti VLA–4 monoclonal antibody inhibits eosinophil infiltration in allergic conjunctivitis model of guinea pig, Current Eye Research, vol. 19, pp. 20–25, 1999.*

Scott M. Whitcup, et al., Blocking ICAM–1 (CD54) AND LFA–1 (CD11a) Inhibits Experimental Allergic Conjunctivitis, Clinical Immunology, vol. 93, No. 2, pp. 107–133, 1999.*

Antonio Soriano, et al., VCAM–1, but Not ICAM–1 or MAdCAM–1, Immunoblockade Ameliorates DSS–Induced Colitis in Mice, Laboratory Investigation, vol. 80, No. 10, pp. 1541–1551, 2000.*

Angela Zeidler, et al., THERAPEUTIC EFFECTS OF ANTIBODIES AGAINST ADHESION MOLECULES IN MURINE COLLAGEN TYPE II–INDUCED ARTHRITIS, Autoimmunity, vol. 21, pp. 245–252, 1995.*

B. Bendjelloul, et al., Intercellular adhesion molecule–1 (ICAM–1) deficiency protects mice against severe forms of experimentally induces colitis, Clin. Exp. Immunol. vol. 119 pp. 57–63, 2000.*

Walter W. Wolyniec, et al., Reduction of Antigen–induced Airway Hyperractivity and Eosinophilia in ICAM–1–deficient Mice, Am. J. Respir. Cell Mol. Biol., vol. 18, pp. 777–785, 1998.*

Daniel C. Bullard, et al., Reduced Susceptibility to Collagen–Induced Arthritis in Mice Deficient in Intercellular Adhesion Molecule–1, Journal of Immunology, vol. 157 pp. 3153–3158, 1996.*

Diane H. Boschelli, et al., Inhibition of E–Selectin–, ICAM–1–, and VCAM–1–Mediated Cell Adhesion by Benzo[b]thiphene–,Benzofuran–,Indole–, and Naphthalene– 2–carboxamides: Identification of PD 144795 as an Antinflammatory Agent, J. Med. Chem. vol. 38 pp. 4597–4614, 1995.*

Robert I. Fox, et al., SJÖGREN'S SYNDROME, Arthritis and Rheumatism, vol. 29, No. 5 pp. 577–585, 1996.*

* cited by examiner

CYCLIC AMINE COMPOUNDS AND PHARMACEUTICAL COMPOSITION CONTAINING THE SAME

BACKGROUND OF THE INVENTION

1. Field of the Invention

The present invention relates to novel cyclic amine compounds which have inhibitory effects on both cell adhesion and cell infiltration and are useful as anti-asthmatic agents, anti-allergic agents, anti-rheumatic agents, anti-arteriosclerotic agents, anti-inflammatory agents, anti-Sjogren's syndrome agents or the like, and medicines containing such compounds.

2. Description of the Background Art

In various inflammatory diseases, infiltration of leukocytes into inflammatory sites is observed. For example, infiltration of eosinophils into the bronchus in asthma (Ohkawara, Y. et al., Am. J. Respir. Cell Mol. Biol., 12 4–12 (1995)), infiltration of macrophages and T lymphocytes into the aorta in arteriosclerosis (Sakai, A. et al., Arterioscler Thromb. Vasc. Biol., 17, 310–316 (1997)), infiltration of T lymphocytes and eosinophils into the skin in atopic dermatitis (Wakita, H. et al., J. Cutan. Pathol., 21 33–39 (1994)) or contact dermatitis (Satoh, T. et al., Eur. J. Immunol., 27, 85–91 (1997)), and infiltration of various leukocytes into rheumatoid synovial tissue (Tak, P P. et al., Clin. Immunol. Immunopathol., 77, 236–242 (1995)), have been reported. Sjogren's syndrome in humans is an organ-specific autoimmune disease characterized by lymphocytic infiltration into the salivary and lacrimal glands, resulting in symptoms of dry mouth and dry eye due to insufficient secretion (Fox R I et al.: "Sjogren's syndrome: proposed criteria for classification" Arthritis Rheum 29, 577–585 (1986).

Infiltration of these leukocytes is elicited by cytokines, chemokines, lipids, and complements produced in inflammatory sites (Albelda, S M. et al., FASEB J., 8, 504–512 (1994)). Activated leukocytes adhere to vascular endothelial cells through an interaction called rolling or tethering with endothelial cells activated likewise. Thereafter, the leukocytes transmigrate through endothelium to infiltrate into the inflammatory sites (Springer, T A., Annu. Rev. Physiol., 57 827–872 (1995)). In adhesion of leukocytes to the vascular endothelial cells in this process, various cell adhesion molecules such as an immunoglobulin superfamily (ICAM-1, VCAM-1 and the like), a selectin family (E-selectin and the like), an integrin family (LFA-1, VLA-4 and the like) and CD44, which are induced on the surfaces of the cells by stimulation by cytokines or the like, play important roles ("Rinsho Meneki (Clinical Immune)", 30, Supple. 18 (1998)), and a relationship between the disorder state and aberrant expression of the cell adhesion molecules is noted.

Accordingly, an agent capable of inhibiting cell adhesion or cell infiltration can be useful as an agent for preventing and treating allergic diseases such as bronchial asthma, dermatitis, rhinitis and conjunctivitis; autoimmune diseases such as rheumatoid arthritis, nephritis, Sjogren's syndrome, inflammatory bowel diseases, diabetes and arteriosclerosis; and chronic inflammatory diseases. In fact, it has been reported that antibodies against adhesion molecules or leukocytes such as LFA-1, Mac-1 and VLA-4 on antibodies against ICAM-1, VCAM-1, P-selectin, E-selectin and the like on vascular endothelial cells, which become ligands thereof, inhibit infiltration of leukocytes into inflammatory sites in animal models. For example, neutralizing antibodies against VCAM-1 and VLA-4, which is a counter receptor thereof, can delay development of diabetes in an NOD mouse model which spontaneously causes the diabetes (Michie, S A. et al., Curr. Top. Microbiol. Immunol., 231 65–83 (1998)). It has also been reported that an antibody against VLA-4 or ICAM-1 and its counter receptor, LFA-1, inhibits infiltration of eosinophils in a guinea pig and mouse allergic conjunctivitis model (Ebihara et al., Current Eye Res., 19, 20–25 (1999); Whitcup, S M et al., Clin. Immunol., 93, 107–113 (1999)), and a monoclonal antibody against VCAM-1 inhibits infiltration of leukocytes in a mouse DSS-induced colitis model to attenuate colitis (Soriano, A. et al., Lab. Invest., 80, 1541–1551 (2000)). Further, an anti-VLA-4 antibody and an anti-CD44 antibody reduce the incidence of disease symptoms in a mouse collagen arthritis model (Zeidler, A. et al., Autoimmunity, 21, 245–252 (1995)). Even in cell adhesion molecule deficient-mice, inhibition of infiltration of leukocytes into inflammatory tissues is observed likewise in inflammatory models (Bendjelloul, F. et al., Clin. Exp. Immunol., 119, 57–63 (2000); Wolyniec, W W. et al., Am. J. Respir. Cell Mol. Biol., 18, 777–785 (1998); Bullard, D C. et al., J. Immunol., 157, 3153–3158 (1996)).

However, it is difficult to develop antibody-based drugs because they are polypeptides and so oral administration is a problem. Moreover, the possible side effects due to antigenicity and allergic reactions are problems.

On the other hand, there have been various investigations of low-molecular weight compounds having an inhibitory effect on cell adhesion with a view toward permitting oral administration. These compounds include benzothiophene derivatives (Boschelli, D H. et al., J. Med. Chem., 38, 4597–4614 (1995)), naphthalene derivatives (Japanese Patent Application Laid-Open No. 10-147568), hydroxybenzoic acid derivatives (Japanese Patent Application Laid-Open No. 10-182550), lignans (Japanese Patent Application Laid-Open No. 10-67656), 2-substituted benzothiazole derivatives (Japanese Patent Application Laid-Open No. 2000-086641 through PCT route), condensed pyrazine compounds (Japanese Patent Application Laid-Open No. 2000-319377 through PCT route), 2,6-dialkyl-4-silylphenol (Japanese Patent Application Laid-Open No. 2000-500970 through PCT route) and the like. However, the goal has not often been sufficiently achieved under the circumstances. Cyclic diamine compounds described in Japanese Patent Application Laid-Open Nos. 9-143075 and 11-92382 and Japanese Patent Application No. 2000-271220 do not exhibit a sufficient inhibitory effect on cell adhesion, and so there is a demand for further improvement in activity.

SUMMARY OF THE INVENTION

An object of the present invention is to provide a substance having inhibitory effects on both cell adhesion and cell infiltration, plus excellent anti-asthmatic effects, anti-allergic effects, anti-rheumatic effects, anti-arteriosclerotic effects, anti-inflammatory effects and anti-Sjogren's syndrome effect.

With the foregoing circumstances in mind, the present inventors carried out an extensive investigation to find a substance which inhibits cell adhesion and cell infiltration. As a result, we found that compounds represented by the general formula (1) having phenyl-pyridyl or biphenyl groups at both ends of the cyclic amine, have excellent cell adhesion-inhibiting effects and cell infiltration-inhibiting effects and are useful as anti-allergic agents, anti-asthmatic agents, anti-rheumatic agents, anti-arteriosclerotic agents or anti-inflammatory agents or anti-Sjogren's syndrome agents.

The present invention provides a cyclic amine compound represented by the following general formula (1):

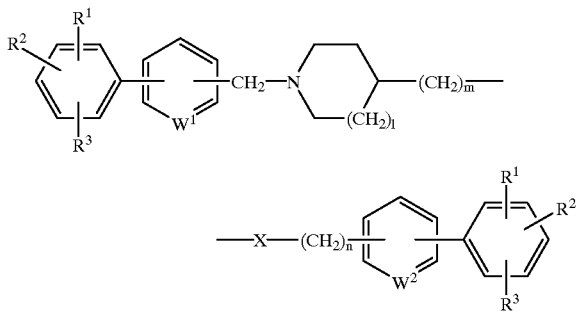

(I)

wherein,

R$^1$, R$^2$ and R$^3$ each independently represent a hydrogen atom, a halogen atom, or hydroxy, alkyl, halogen-substituted alkyl, alkoxy, alkylthio, carboxyl, alkoxycarbonyl or alkanoyl group;

W$^1$ and W$^2$ each independently represent N or CH;

X represents O, NR$^4$, CONR$^4$ or NR$^4$CO;

R$^4$ each independently represents a hydrogen atom, or an alkyl, alkenyl, alkynyl, substituted or unsubstituted aryl, substituted or unsubstituted heteroaryl, substituted or unsubstituted aralkyl, or substituted or unsubstituted heteroaralkyl group; and l, m and n each represents a number of 0 or 1.

According to the present invention, there is also provided a medicine comprising the above cyclic amine compound, a salt thereof, or a hydrate thereof as an active ingredient.

According to the present invention, there is further provided a pharmaceutical composition comprising the above cyclic amine compound, the salt thereof, or the hydrate thereof and a pharmaceutically acceptable carrier.

According to the present invention, there is still further provided a method for treating a disease caused by cell adhesion and/or cell infiltration, which comprises administering an effective amount of the above cyclic amine compound, a salt thereof, or a hydrate thereof to a patient who requires such treatment.

DETAILED DESCRIPTION OF THE PREFERRED EMBODIMENTS

The compound of the present invention is characterized in that the cyclic amine has two phenyl-pyridyl or biphenyl groups. It has not been known at all that compounds having such structure have both of excellent cell adhesion-inhibiting effects and cell infiltration-inhibiting effects.

In the general formula (1), the halogen atoms for R$^1$, R$^2$ and R$^3$ include fluorine, chlorine, bromine and iodine atoms.

The alkyl group for R$^1$, R$^2$, R$^3$ and R$^4$ typically includes straight, branched or cyclic C$_1$–C$_8$ alkyl groups, such as straight or branched C$_1$–C$_8$ alkyl groups, for example, methyl, ethyl, propyl, butyl, pentyl, hexyl, heptyl and octyl groups, and C$_3$–C$_8$ cycloalkyl groups, for example, cyclopropyl, cyclobutyl, cyclopentyl, cyclohexyl, cyclohexylmethyl and cyclohexylethyl groups. Among them, particularly preferred are C$_1$–C$_6$ alkyl groups such as methyl, ethyl, n-propyl, isopropyl, n-butyl and the like.

The halogen-substituted alkyl group for R$^1$, R$^2$ and R$^3$ typically includes C$_1$–C$_8$ alkyl groups substituted with 1 to 3 halogen atoms. Among them, particularly preferred are C$_1$–C$_6$ alkyl groups substituted with 1 to 3 halogen atoms, such as trifluoromethyl, 2,2,2-trifluoroethyl, etc.

The alkoxy group typically includes straight, branched or cyclic C$_1$–C$_8$ alkoxy groups, such as straight or branched C$_1$–C$_8$ alkoxy groups, for example, methoxy, ethyoxy, propoxy, butoxy, pentyloxy and hexyloxy groups; and C$_3$–C$_8$ cycloalkyloxy groups, for example, cyclopropyloxy, cyclobutyloxy, cyclopentyloxy, cyclohexyloxyl, cyclohexylmethyloxy and cyclohexylethyloxy groups. Among them, particularly preferred are C$_1$–C$_6$ alkoxy groups such as methoxy, ethyoxy, n-propoxy, isopropoxy and n-butyloxy groups.

The alkylthio group typically includes C$_1$–C$_8$ alkylthio groups, and is preferably a C$_1$–C$_6$ alkylthio group such as, for example, methylthio, ethylthio, n-propylthio, isopropylthio or the like.

The alkoxycarbonyl group typically includes C$_1$–C$_6$ alkoxycarbonyl groups, and is preferably a C$_1$–C$_6$ alkoxycarbonyl group such as methoxycarbonyl, ethoxycarbonyl, tert-butoxycarbonyl or the like.

The alkanoyl group typically includes C$_1$–C$_6$ alkanoyl groups and is preferably a C$_1$–C$_4$ alkanoyl group such as acetyl, propionyl, butyryl, isobutyryl or the like.

The alkenyl group for R$^4$ typically includes C$_3$–C$_8$ alkenyl groups and is preferably a C$_3$–C$_6$ alkenyl group such as 2-propenyl, 3-butenyl or the like. The alkynyl group typically includes C$_3$–C$_8$ alkynyl groups and is preferably a C$_3$–C$_6$ alkynyl group such as 2-propynyl, 3-butynyl or the like.

The aryl group for R$^4$ typically includes C$_6$–C$_{14}$ aryl groups and is preferably phenyl, naphthyl, anthryl, indenyl, indanyl, 5,6,7,8-tetrahydronaphthyl or the like. The heteroaryl group for R$^4$ typically includes heteroaryl groups of 5- or 6-membered ring containing 1 to 4 nitrogen atoms in the ring, and is preferably imidazolyl, pyridyl, pyrimidinyl or the like. The aralkyl group typically includes C$_6$–C$_{14}$ aryl—C$_1$–C$_6$ alkyl groups such as phenyl C$_1$–C$_6$ alkyl groups and naphthyl C$_1$–C$_6$ alkyl groups, for example, benzyl, naphthylmethyl, phenylethyl, phenylpropyl, etc. The heteroaralkyl group typically includes 5- or 6-membered ring heteroaryl containing 1 to 4 nitrogen atoms—C$_1$–C$_6$ alkyl groups, such as imidazolyl-C$_1$–C$_6$ alkyl, pyridyl-C$_1$–C$_6$ alkyl, pyrimidinyl-C$_1$–C$_6$ alkyl, etc.

The groups which can substitute the above-mentioned aryl, heteroaryl, aralkyl and heteroaralkyl include 1 to 3 groups or atoms selected from alkyl, alkoxy, halogen-substituted alkoxy, alkylthio, halogen, nitro, amino, acetylamino, trifluoromethyl and alkylenedioxy, wherein said alkyl, alkoxy and alkylthio include those illustrated for R$^1$–R$^3$. The halogen-substituted alkoxy includes C$_1$–C$_8$ alkoxy groups substituted by 1 to 3 halogen atoms, and is preferably a C$_1$–C$_6$ alkoxy group substituted by 1 to 3 halogen atoms such as trifluoromethoxy or 2,2,2-trifluoroethoxy. The alkylenedioxy group typically includes C$_1$–C$_3$ alkylenedioxy groups such as methylenedioxy, ethylenedioxy and propylenedioxy groups.

Preferably, X represents NR$^4$. More preferably, X represents NR$^4$ and R$^4$ represents a substituted or unsubstituted C$_6$–C$_{14}$ aryl group or a substituted or unsubstituted 5- or 6-membered ring heteroaryl group containing 1 to 4 nitrogen atoms in the ring. The compounds of the formula (1) wherein X represents NR$^4$ have particularly strong cell adhesion-inhibiting action as shown later in Test Example 1.

Preferably, R$^1$, R$^2$ and R$^3$ are attached to the phenyl group at the 3, 4 and 5-positions thereof. In this case, it is more preferable that $R^1$ and $R^3$ (at the 3- and 5-positions of the phenyl ring) are an alkoxy group. It is also preferable that $R^2$ (at the 4-position of the phenyl ring) is a hydrogen atom, a halogen atom, or a hydroxy, alkyl, halogen-substituted alkyl, alkoxy, alkylthio, carboxy, alkoxycarbonyl or alkanoyl group. l denotes 0 or 1, and is preferably 1.

No particular limitation is imposed on the salts of the compounds (1) according to the invention as long as they are pharmaceutically acceptable salts. Examples include the acid-addition salts of mineral acids, such as hydrochlorides, hydrobromides, hydriodides, sulfates and phosphates; and acid-addition salts of organic acids, such as benzoates, methanesulfonates, ethanesulfonates, benzenesulfonates, p-toluenesulfonates, oxalates, maleates, fumarates, tartrates, citrates and acetates.

The compounds of formula (1) may be present in the form of solvates typified by hydrates, and the solvates are embraced in the present invention.

The compounds of formula (1) can be prepared in accordance with the following processes A~J:

Process A: Preparation of the compound of the formula (1) wherein l=1, m=0, n=1 and X=CONR$^4$ ing compound (4) is treated with thiophenol in the presence of a base such as potassium carbonate to eliminate the 2-nitrobenzenesulfonyl group, thereby giving amine compound (5). Alternatively, when $R^4$ is H. it is possible to react compound (2) with potassium phthalimide and then treat the resulting phthalimide derivative (6) with hydrazine to give the corresponding amine compound (5).

On the other hand, compound (2) is reacted with ethyl isonipecotate (7) in a solvent such as acetonitrile, N,N-dimethylformamide (DMF), dimethyl sulfoxide (DMSO), tetrahydrofuran (I), dioxane, toluene, benzene, etc. in the presence of a base such as potassium carbonate or the like at a temperature between 0° C. and a reflux temperature for several hours to several days, preferably at room temperature overnight, to give compound (8). The compound (8) is subjected to a usual alkaline hydrolysis to give the corresponding carboxylic acid compound (9).

The carboxylic acid compound (9) is reacted with the amine compound (5) using a dehydration condensing agent such as 1-(3-dimethylaminopropyl)-3-ethylcarbodiimide hydrochloride (water-soluble carbodiimide), 2-(1H-benzotriazol-1-yl)-1,1,3,3-tetramethyluronium hexafluorophosphate (HBTU) or the like in a solvent such as

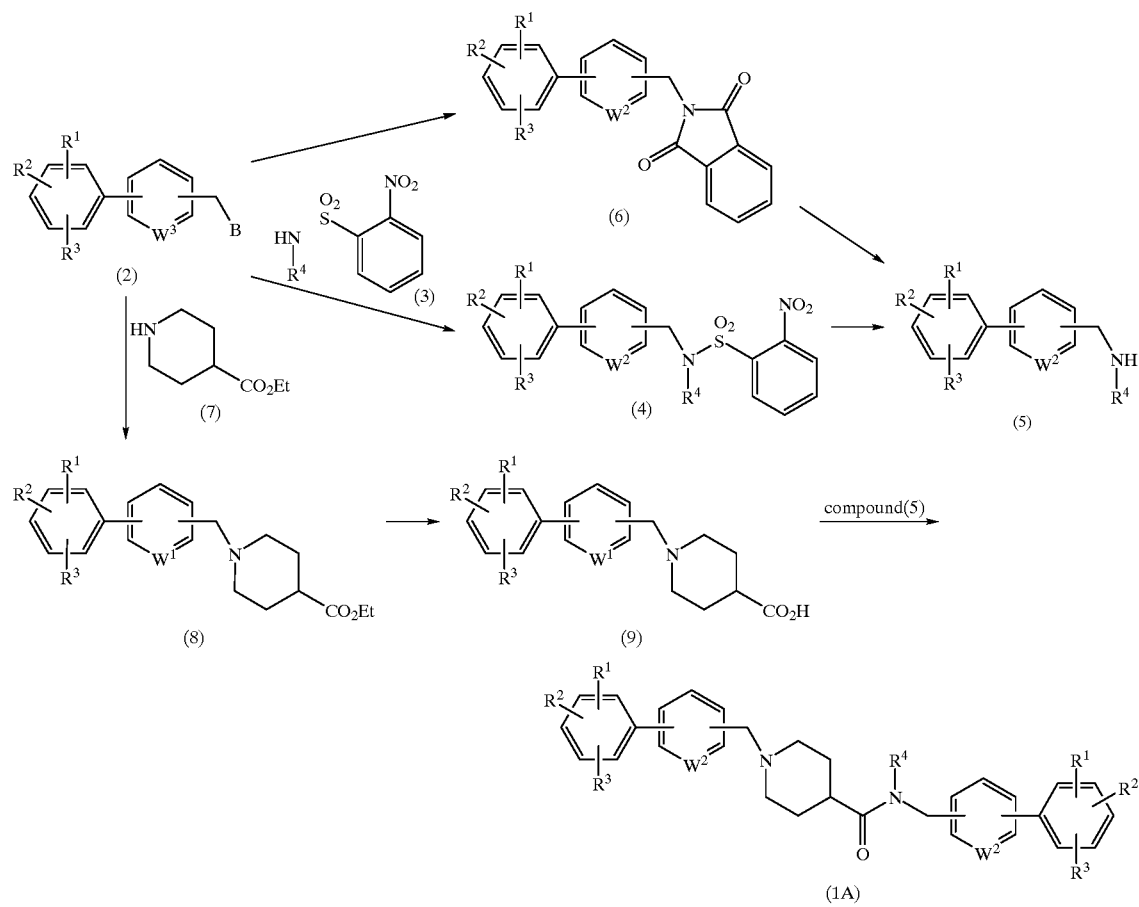

wherein, $W^1$, $W^2$, $R^1$, $R^2$, $R^3$ and $R^4$ are as defined above, $W^3$ has the same meaning as $W^1$ or $W^2$, and B denotes a leaving group such as a halogen atom, or methanesulfonyloxy or p-toluenesulfonyloxy group.

Compound (2) and an N-(2-nitro)benzenesulfonylamine derivative (3) are reacted to give compound (4). The result-chloroform, dichloroethane, THF, dioxane, acetonitrile, etc. at a temperature between 0° C. and a reflux temperature for several hours to several days, preferably at room temperature for 12 hours, to give an end product (1A).

Process B: Preparation of the compound of the formula (1) wherein l=1, m=0, n=1 and X=O

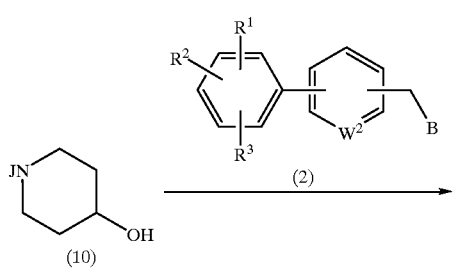
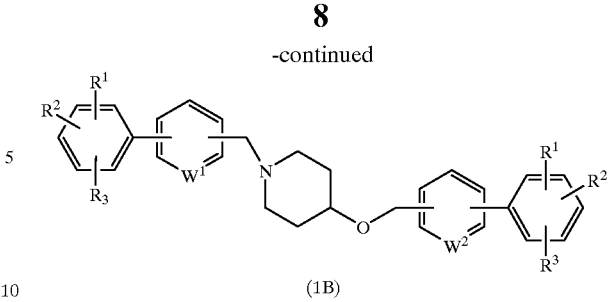

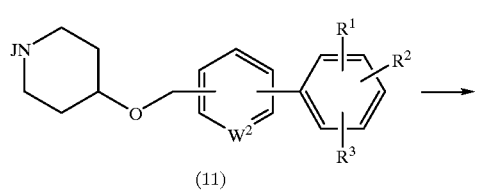

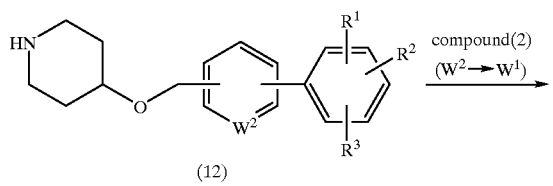

wherein, B, $W^1$, $W^2$, $R^1$, $R^2$ and $R^3$ are as defined above, and J denotes a protecting group such as benzyloxycarbonyl, tert-butoxycarbonyl, acetyl, benzoyl or benzyl group. Incidentally, in the reaction schemes shown above and below, the expression "($W^2 \rightarrow W^1$)" following the term "compound(2)" means that $W^2$ in the formula representing compound (2) is changed to $W^1$.

4-hydroxypiperidine compound (10) with a protected amino group is reacted with compound (2) in the presence of sodium hydride or potassium iodide in a solvent such as DMF, DMSO, etc. at a temperature between 0° C. and a reflux temperature for several hours to several days, preferably at room temperature for 2 days, to give compound (11). The protecting group in the compound (11) is removed in a known manner. The resulting compound (12) is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give an end product (1B).

Process C: Preparation of the compound of the formula (1) wherein l=1, m=0, n=0, X=$NR^4$ and $R^4$=H or Me

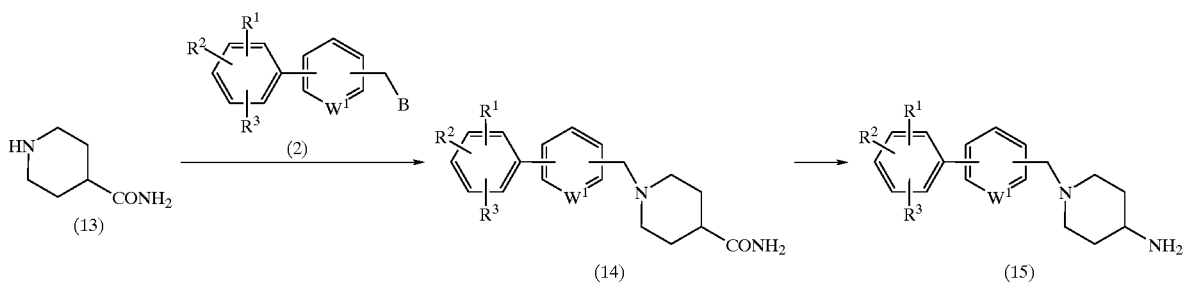

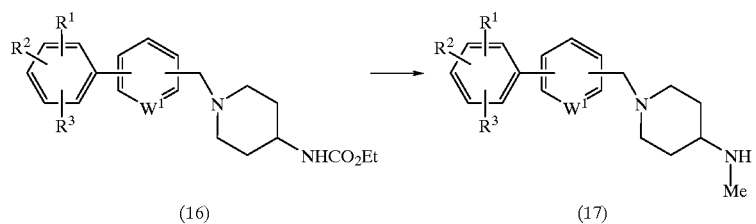

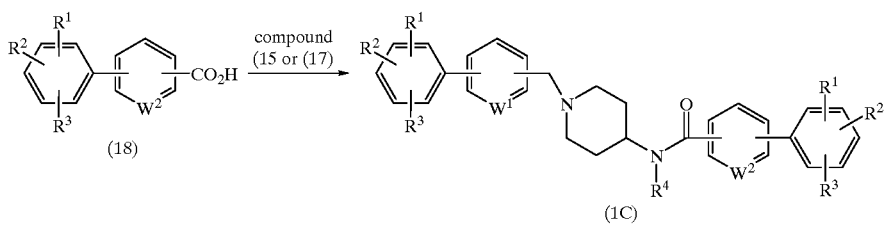

wherein, B, $W^1$, $W^2$, $R^1$, $R^2$ and $R^3$ are as defined above, and $R^4$ denotes a hydrogen atom or methyl group.

Isonipecotamide (13) is reacted with compound (2) in the presence of a base such as potassium carbonate, sodium carbonate or the like in a solvent such as acetonitrile, DMF, DMSO, THF, dioxane, etc. at a temperature between 0° C. and a reflux temperature for several hours to several days, preferably at room temperature for 4 hours, to give compound (14). The compound (14) is subjected to Hofmann rearrangement reaction to give amine compound (15).

On the other hand, by subjecting the compound (14) to Hofmann rearrangement reaction in ethanol, carbamate compound (16) is obtained. Then, by subjecting the compound (16) to a reduction reaction using lithium aluminum hydride, methylamine compound (17) is obtained.

By reacting carboxylic acid compound (18) with the amine compound (15) or methylamine compound (17) similarly to the condensation reaction in Process A, an end compound (1C) is obtained.

Process D: Preparation of the compound of the formula (1) wherein l=1, m=0, n=1 and X=$NR^4$ wherein, B, $W^1$, $W^2$, $R^1$, $R^2$ and $R^3$ are as defined above, and $R^4$ denotes an alkyl, alkenyl, alkynyl, aralkyl or heteroaralkyl group.

The amine compound (15) mentioned in the above is reacted with 2-nitrobenzenesulfonyl chloride (19) according to a known manner to give compound (20). The compound (20) is reacted with compound (2) in the presence of a base such as potassium carbonate in a solvent such as acetonitrile, DMF, DMSO, THF, dioxane or the like at a temperature between 0° C. and a reflux temperature for several hours to several days, preferably at room temperature for 4 hours, to give compound (21). The benzenesulfonyl group of the compound (21) is removed similarly to the procedure for the compound (4) in Process A to give an end compound (1D) ($R^4$=H). The compound (1D) is reacted with $R^4$—B in the presence of a base such as sodium carbonate, sodium bicarbonate, potassium carbonate, cesium carbonate or the like in a solvent such as acetonitrile, THF, dioxane, chloroform, dichloromethane, DMF, DMSO or the like at a temperature between 0° C. and a reflux temperature for several hours to several days, preferably at 80° C. for 12 hours, to give compound (1D').

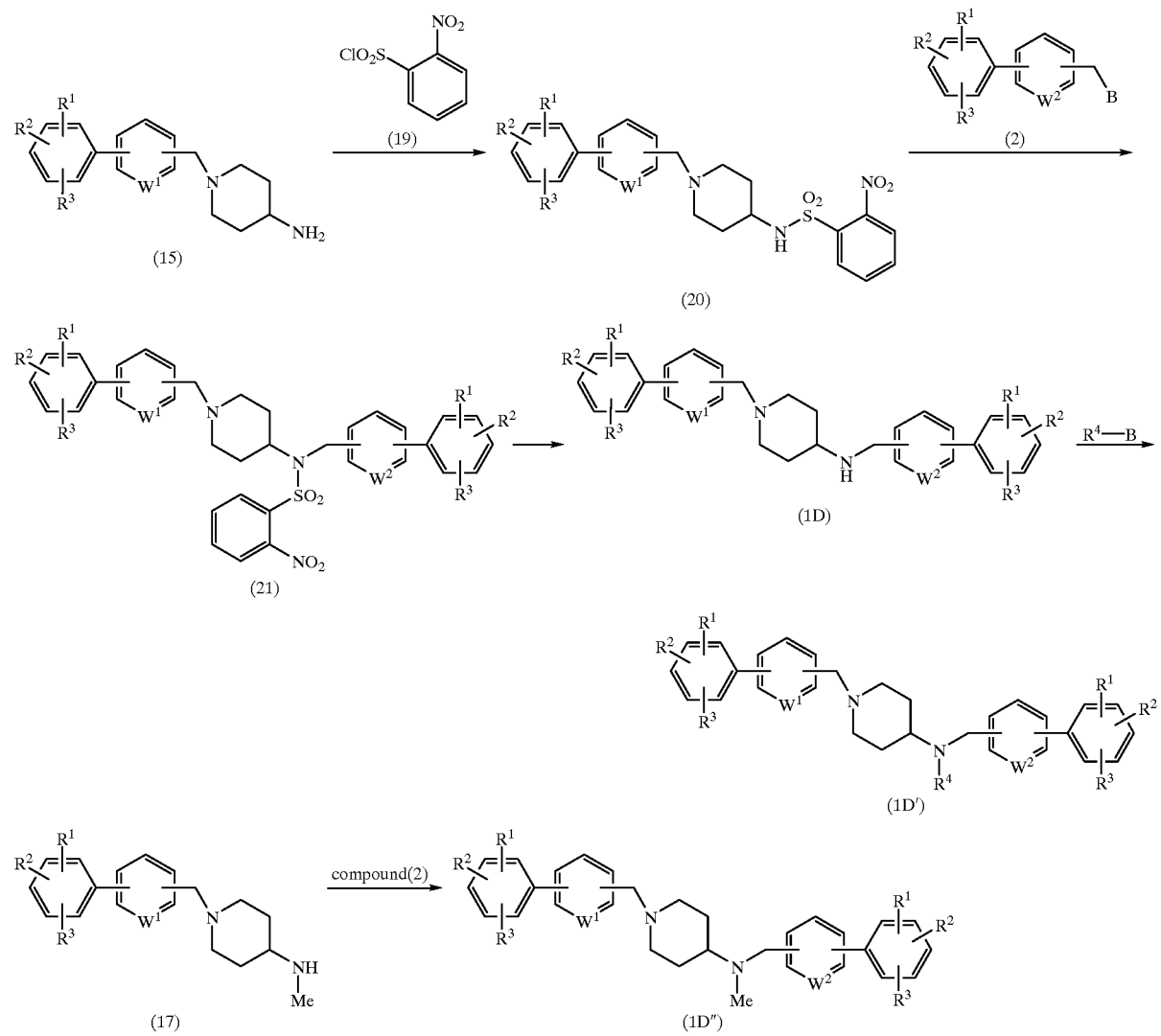

On the other hand, the methylamine compound (17) is reacted compound (2) in the presence of a base such as potassium carbonate in a solvent such as acetonitrile, DMF, DMSO, THF, dioxane or the like at a temperature between 0° C. and a reflux temperature for several hours to several days, preferably at room temperature for 4 hours, to give an end compound (1D") (R⁴=Me).

Process E: Preparation of the compound of the formula (1) wherein l=1, m=0 or 1, n=1 and X=NR⁴,

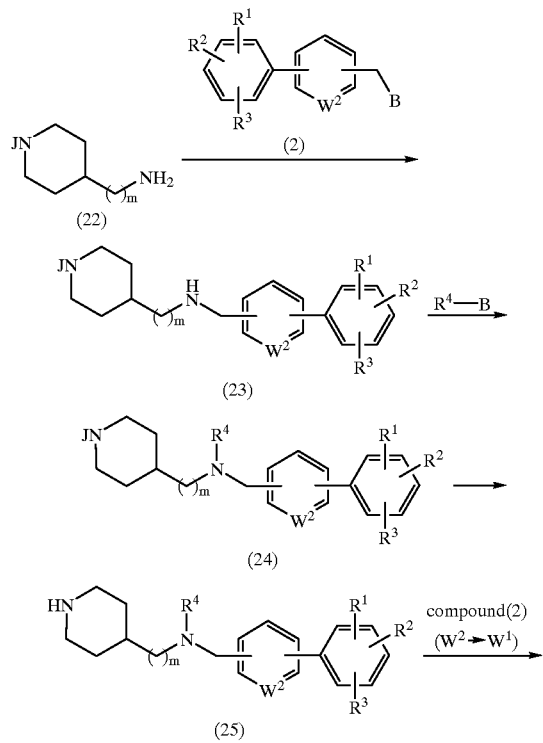

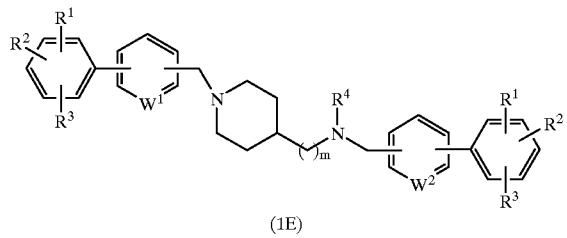

wherein, B, J, W¹, W², R¹, R² and R³ are as defined above, and R⁴ denotes an alkyl, alkenyl, alkynyl, aralkyl or heteroaralkyl group.

Aminopiperidine derivative (22) in which the amino group on the ring is protected is reacted with compound (2) in the presence of a base such as potassium carbonate in a solvent such as acetonitrile, DMF, DMSO, THF, dioxane or the like at a temperature between 0° C. and a reflux temperature for several hours to several days, preferably at room temperature for 4 hours, to give compound (23). The compound (23) is reacted with R⁴—B in the presence of a base such as sodium carbonate, sodium bicarbonate, potassium carbonate, cesium carbonate or the like in a solvent such as acetonitrile, THF, dioxane, chloroform, dichloroethane, DMF, DMSO or the like at a temperature between 0° C. and a reflux temperature for several hours to several days, preferably at 80° C. for 12 hours, to give compound (24). After removal of the protecting group, the compound (25) is reacted compound (2) in the presence of a base such as potassium carbonate in a solvent such as acetonitrile, DMF, DMSO, THF, dioxane or the like at a temperature between 0° C. and a reflux temperature for several hours to several days, preferably at room temperature for 4 hours, to give compound (1E).

Process F: Preparation of the compound of the formula (1) wherein l=1, m=0, n=1 and X=NR⁴,

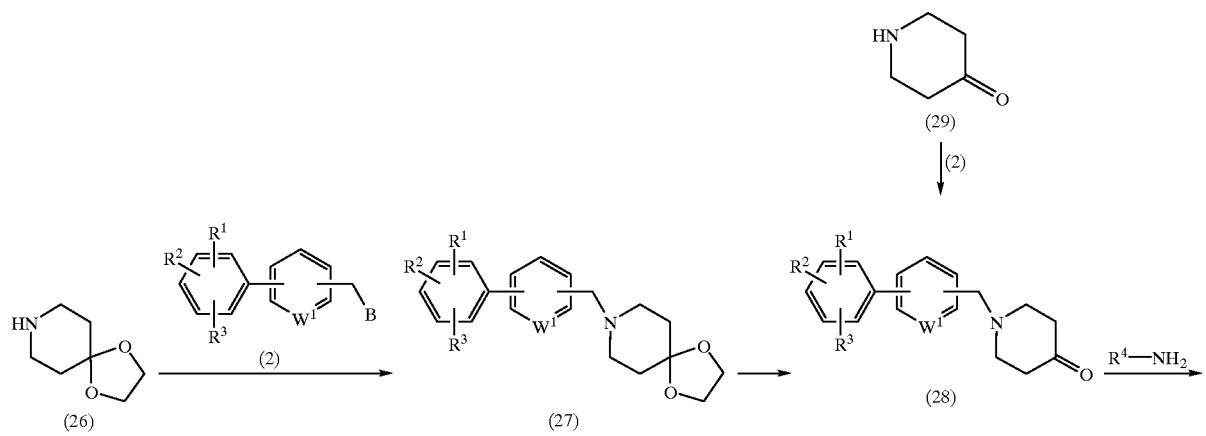

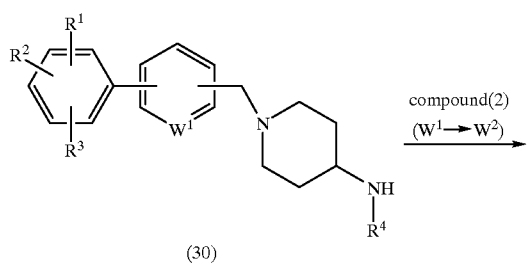

(30)

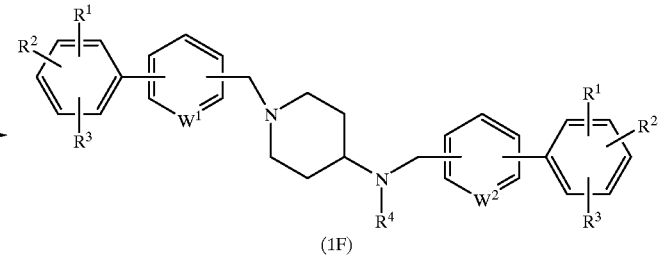

(1F)

wherein, B, $W^1$, $W^2$, $R^1$, $R^2$ and $R^3$ are as defined above, and $R^4$ denotes an alkyl, alkenyl, alkynyl, aralkyl, heteroaralkyl, aryl or heteroaryl group.

4-piperidone ethylene ketal (26) is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give compound (27), which in turn is deketalized by using an acid to give ketone compound (28).

On the other hand, 4-piperidone (29) is reacted compound (2) in the presence of a base such as potassium carbonate in a solvent such as acetonitrile, DMF, DMSO, THF, dioxane or the like at a temperature between 0° C. and a reflux temperature for several hours to several days, preferably at room temperature for 4 hours, to give compound (28). Using the compound (28), amine compound (30) can be prepared according to either of the following two synthesis processes:

Synthesis process 1: The compound (28) is reacted with an amine compound of the formula: $R^4$—$NH_2$ in the presence of molecular sieves in toluene or benzene at a temperature between 0° C. and a reflux temperature for several hours to several days, preferably at reflux temperature for 12 hours, followed by reaction with a reducing agent such as sodium borohydride or sodium cyanoborohydride at a temperature between 0° C. and a reflux temperature for several minutes to several days, preferably at room temperature for 1 hour, to give the amine compound (30).

Synthesis process 2: The compound (28) is reacted with an amine compound of the formula: $R^4$—$NH_2$ in the presence of a reducing agent such as sodium triacetoxy boron hydride in a solvent such as dichloromethane, 1,2-dichloroethane, methanol, ethanol, etc. at a temperature between 0° C. and a reflux temperature for several minutes to several days, preferably at room temperature for 4 hours, to give the amine compound (30).

The resulting compound (30) is reacted compound (2) in a solvent such as acetonitrile, DMF, DMSO, THF, dioxane, etc. at a temperature between 0° C. and a reflux temperature for several hours to several days, preferably at room temperature for 4 hours, to give an end product (IF).

Process G: Preparation of the compound of the formula (1) wherein l=1, m=0, n=1 and X=$NR^4$

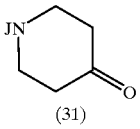

(31)

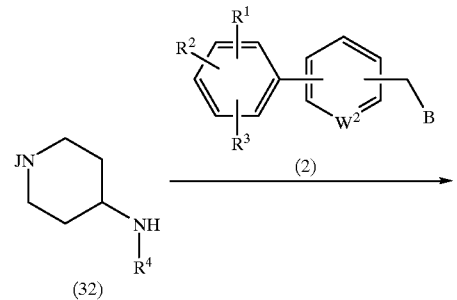

(32)

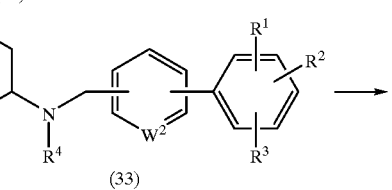

(33)

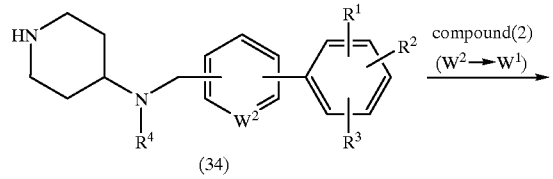

(34)

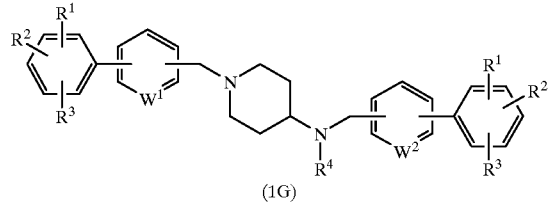

(1G)

wherein, B, J, $W^1$, $W^2$, $R^1$, $R^2$ and $R^3$ are as defined above, and $R^4$ denotes an alkyl, alkenyl, alkynyl, aralkyl, heteroaralkyl, aryl or heteroaryl group.

4-piperidone derivative (31) in which the amino group on the ring is protected is reacted with an amine compound $R^4$—$NH_2$ similarly to the procedure for preparation of compound (30) in Process F to give compound (32). The compound (32) is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give compound (33). After removal of the protecting group from the compound (33), the resulting compound (34) is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give an end product (1G).

Process H: Preparation of the compound of the formula (1) wherein l=0, m=0, n=1 and X=NH

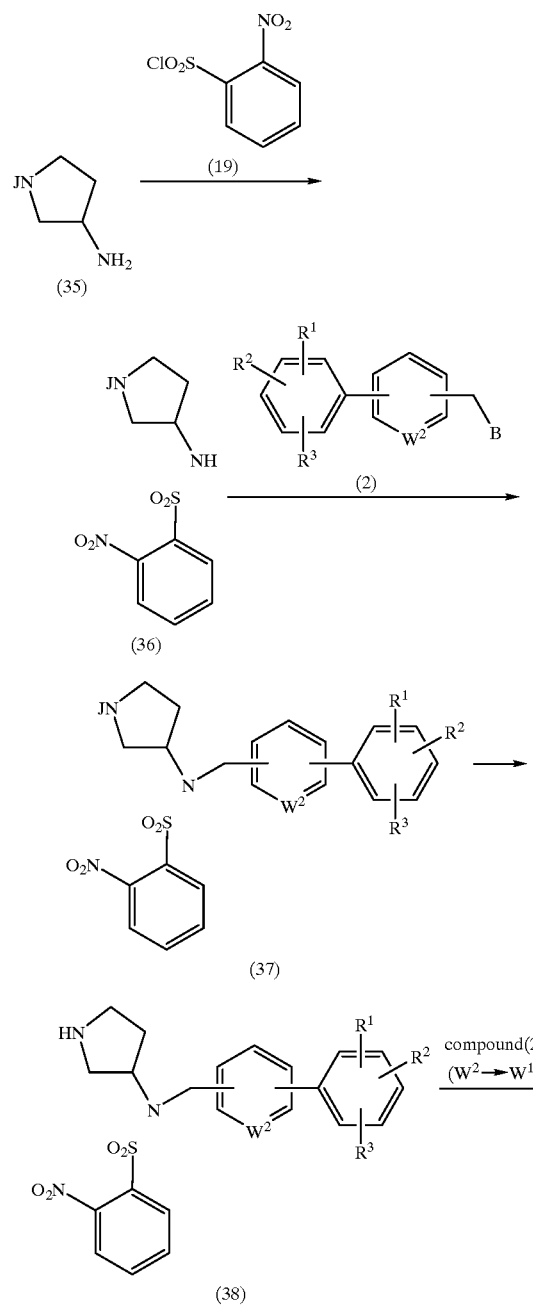

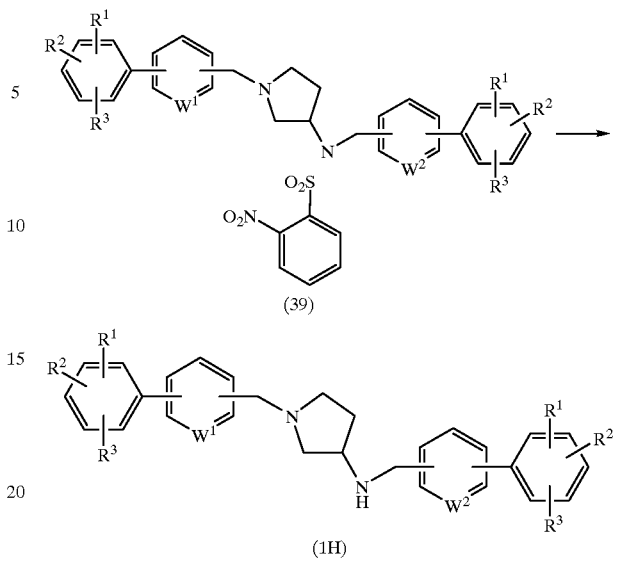

wherein, B, J, W$^1$, W$^2$, R$^1$, R$^2$ and R$^3$ are as defined above.

3-aminopyrrolidine derivative (35) with a protected amino group on the ring is reacted with 2-nitrobenzenesulfonyl chloride (19) under usual conditions to give a benzenesulfonyl derivative (36). The derivative (36) is reacted with compound (2) in the presence of a base such as potassium carbonate in a solvent such as acetonitrile, DMF, DMSO, THF; dioxane, etc. at a temperature between 0° C. and a reflux temperature for several hours to several days, preferably at room temperature for 4 hours, to give compound (37). The protecting group of the amino group is removed from the compound (37) to give compound (38), which in turn is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give compound (39). By subjecting the compound (39) to a reaction similar to that in the preparation of compound (5) in Process A, an end product (1H) is obtained.

Process I: Preparation of the compound of the formula (1) wherein l=0, m=0, n=1 and X=NR$^4$

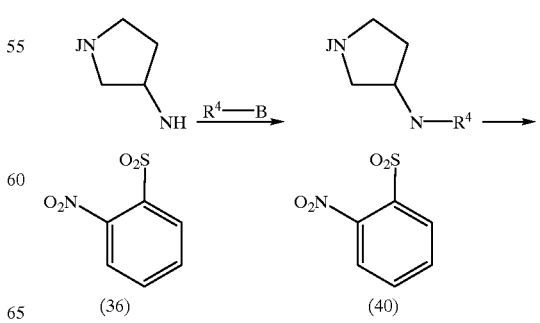

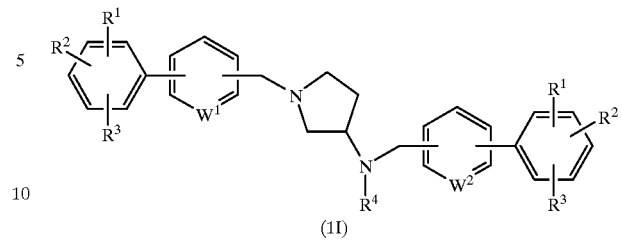

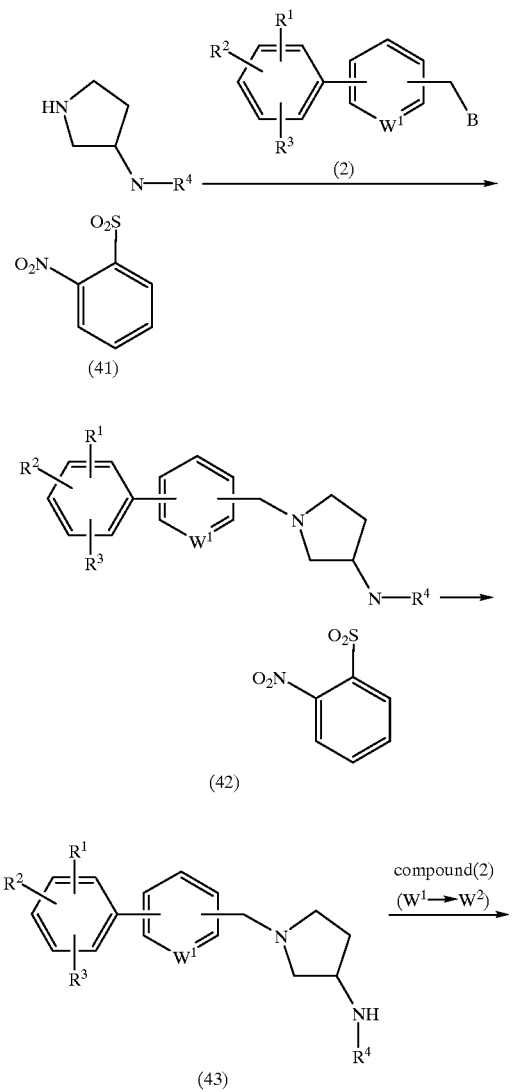

wherein, B, J, $W^1$, $W^2$, $R^1$, $R^2$ and $R^3$ are as defined above, and $R^4$ denotes an alkyl, alkenyl, alkynyl or aralkyl group.

Compound (36) is reacted with $R^4$—B in the presence of a base such as sodium carbonate, potassium carbonate, etc. in a solvent such as acetonitrile, THF, dioxane, chloroform, dichloroethane, DMF, DMSO, etc. at a temperature between 0° C. and a reflux temperature for several hours to several days, preferably at 80° C. for 12 hours, to give compound (40). The amino-protecting group is removed from the compound (40), and the resulting compound (41) is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give compound (42). By subjecting the compound (42) to a reaction similar to that in the preparation of compound (5) in Process A, compound (43) is obtained. The compound (43) is reacted with compound (2) in the presence of a base such as potassium carbonate in a solvent such as acetonitrile, DMF, DMSO, THF, dioxane, etc. at a temperature between 0° C. and a reflux temperature for several hours to several days, preferably at room temperature for 4 hours, to give an end product (1I).

Process J: Preparation of the compound of the formula (1) wherein $R^2$=OH

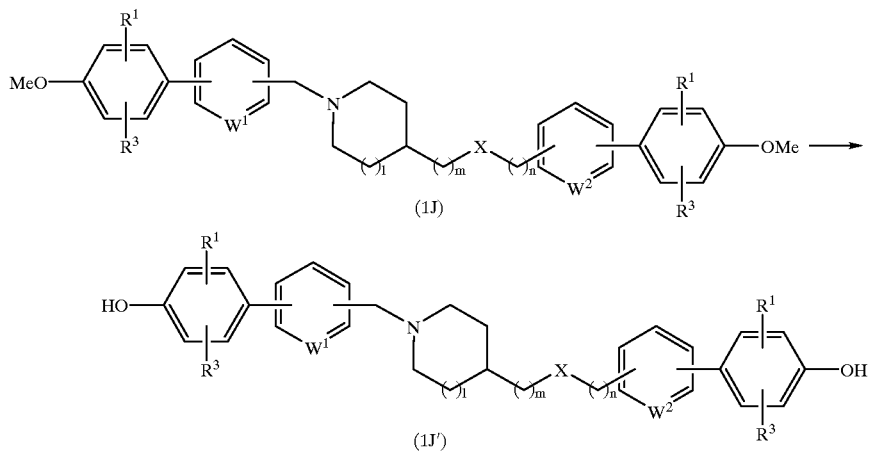

wherein, X, $W^1$, $W^2$, $R^1$, $R^3$, l, m and n have the same meanings as initially defined.

By reacting methoxy compound (1J) with iodotrimethylsilane in a solvent such as toluene, chloroform, dichloromethane, etc. at a temperature between −25° C. and a reflux temperature for several minutes to several days, preferably at 0° C. for 2 hours, there can be obtained an end product (1J').

The compounds (1) according to the present invention are obtained by any of the above-described processes and may further be purified by using an ordinary purification means such as recrystallization or column chromatography as needed. As needed, the compounds may also be converted into the desired salts or solvates in a method known per se in the art. When the compounds (1) have an asymmetric carbon atom, the present invention includes any configurational isomers.

The compounds (1) according to the present invention, or salts or solvates thereof thus obtained have an excellent inhibitory effect on cell adhesion as demonstrated in the examples, which will be described subsequently, and are useful as medicines for treatment and prevention of diseases of animals including humans, caused by cell adhesion or cell infiltration, for example, asthma, allergy, rheumatism, arteriosclerosis, inflammation, Sjogren's syndrome, etc.

The medicine according to the present invention comprises a compound (1), a salt thereof, or a solvate thereof as an active ingredient. The form of administration may be suitably selected as necessary for the therapeutic application intended without any particular limitation, including oral preparations, injections, suppositories, ointments, inhalants, eye drops, nose drops and plasters. A composition suitable for use in these administration forms can be prepared by blending a pharmaceutically acceptable carrier in accordance with the conventional preparation method publicly known by those skilled in the art.

When an oral solid preparation is formulated, an excipient, and optionally, a binder, disintegrator, lubricant, colorant, a taste corrigent, a smell corrigent and the like are added to compound (1) and the resulting composition can be formulated into tablets, coated tablets, granules, powders, capsules, etc. in accordance with methods known in the art.

As such additives described above, any additives may be used which are generally used in the pharmaceutical field. Examples include excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dry starch, sodium alginate, agar powder, sodium hydrogencarbonate, calcium carbonate, sodium lauryl sulfate, monoglyceryl stearate and lactose; lubricants such as purified talc, stearic acid salts, borax and polyethylene glycol; and taste corrigents such as sucrose, orange peel, citric acid and tartaric acid.

When an oral liquid preparation is formulated, a taste corrigent, buffer, stabilizer, smell corrigent and/or the like are added to compound (1) and the resulting composition can be formulated into internal liquid preparations, syrup preparations, elixirs, etc. in accordance with methods known in the art. In this case, vanillin as the taste corrigent, may be used. As the buffer, sodium citrate may be mentioned. As examples of the stabilizer, tragacanth, gum arabic and gelatin may be mentioned.

When an injection is formulated, a pH adjustor, buffer, stabilizer, isotonicity agent, local anesthetic and the like may be added to compound (1) according to the present invention, and the resultant composition can be formulated into subcutaneous, intramuscular and intravenous injections in accordance with methods known in the art. Examples of the pH adjustor and buffer in this case include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the isotonicity agent include sodium chloride and glucose.

When a suppository is formulated, a carrier preparation known in the art, for example, polyethylene glycol, lanoline, cacao butter, fatty acid triglyceride or the like, and optionally, a surfactant such as Tween (trade mark) and the like are added to the compound (1), and the resultant composition can be formulated into suppositories in accordance with methods known in the art.

When an ointment is formulated, a base material, stabilizer, wetting agent, preservative and the like, which are generally used, are blended with compound (1) as needed, and the resulting blend is mixed and formulated into ointments in accordance with known method known methods. Examples of the base material include liquid paraffin, white vaseline, bleached beeswax, octyldodecyl alcohol and paraffin. Examples of the preservative include methyl p-hydroxybenzoate, ethyl p-hydroxybenzoate and propyl p-hydroxybenzoate.

Besides the above preparations, inhalants, eye drops and nose drops may also be formulated in accordance with known methods.

The dose of the medicine according to the present invention varies according to the age, weight and condition of the patient to be treated, the administration method, the number of times of administration, and the like. It is however preferred that the medicine is generally orally or parenterally administered at once or in several portions in a dose of 1 to 1,000 mg per day in terms of compound (1), for an adult.

The present invention will hereinafter be described in more detail by Examples. However, the present invention is not limited to these examples.

PREPARATION EXAMPLE 1

Synthesis of ethyl 2-(3,4,5-trimethoxyphenyl)isonicotinate:

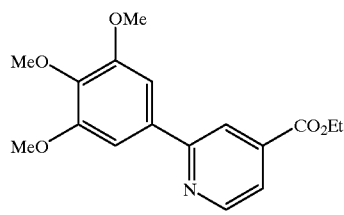

3,4,5-Trimethoxyphenylboronic acid (20.10 g) and ethyl 2-chloroisonicotinate (18.56 g) were suspended in a mixed solvent of toluene (200 mL) and THF(100 mL), and to the suspension 2 M sodium carbonate (200 mL) and tetrakis (triphenyl phosphine) palladium(0) (5.78 g) were added. The mixture was stirred at 90° C. overnight under an argon atmosphere. Ethyl acetate was added to the reaction mixture to separate an organic layer. The organic layer was washed with brine, dried over anhydrous sodium magnesium and concentrated under reduced pressure. The residue was purified by column chromatography on silica gel using hexane-ethyl acetate (5:1) to give the title compound.

Yield: 27.99 g (88%). ¹H-NMR (400 MHz, CDCl₃): 1.45 (t, 3H, J=7.0 Hz), 3.92 (s, 3H), 3.99 (s, 6H), 4.46 (q, 2H, J=7.0 Hz), 7.30 (s, 2H), 7.76 (dd, 1H, J=5.1 Hz, 1.6 Hz), 8.24 (dd, 1H, J=1.6 Hz, 0.8 Hz), 8.81 (dd, 1H, J=5.1 Hz, 0.8 Hz).

PREPARATION EXAMPLE 2

Synthesis of 4-hydroxymethyl-2-(3,4,5-trimethoxyphenyl)pyridine:

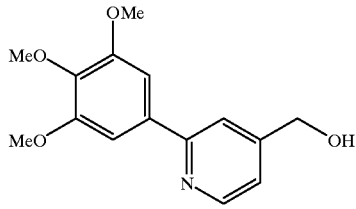

Ethyl 2-(3,4,5-trimethoxyphenyl)isonicotinate (24.57 g) was dissolved in dry THF (200 mL), and to the solution lithium aluminum hydride (2.94 g) was added at 0° C. under an argon atmosphere. The mixture was stirred at 0° C. for 1 hour as it is. A small amount of water and then sodium sulfate were added to the reaction mixture, and the reaction mixture was filtered through celite. The filtrate was evaporated, and the reultant crude crystals were recrystalized from ethyl acetate-hexane to give the title compound.

Yield: 17.53 g (82%). ¹H-NMR (400 MHz, CDCl₃): 3.90 (s, 3H), 3.95 (s, 6H), 4.79 (s, 2H), 7.19 (d, 1H, J=5.1 Hz), 7.21 (s, 2H), 7.66 (s, 1H), 8.60 (d, 1H, J=5.1 Hz).

PREPARATION EXAMPLE 3

Synthesis of 4-chloromethyl-2-(3,4,5-trimethoxyphenyl)pyridine:

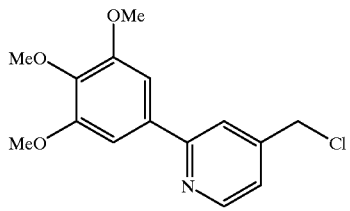

4-hydroxymethyl-2-(3,4,5-trimethoxyphenyl)pyridine (19.18 g) was dissolved in chloroform (100 mL), and to the solution thinly chloride (10.2 mL) was added at 0° C. After 30 minutes, the mixture was warmed to room temperature and stirred for 4 hours. The reaction mixture was washed with aqaueous saturated sodium hydrogendcarbonate and brine, dried over anhydrous sodium sulfate and evaporated. The residue was then recrystallized from ethyl acetate-hexane to give the title compound as pale yellow crystalline powder.

Yield: 18.24 g (89%). ¹H-NMR (400 MHz, CDCl₃): 3.91 (s, 3H), 3.97 (s, 6H), 4.61 (s, 2H), 7.24 (s, 2H), 7.26 (d, 1H, J=5.1 Hz), 7.68 (s, 1H), 8.67 (d, 1H, J=5.1 Hz).

PREPARATION EXAMPLE 4

Synthesis of N-[[2-(3,4,5-trimethoxyphenyl)pyridin-4-yl]methyl]phthalimide:

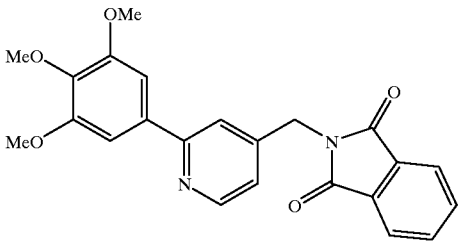

To a solution of 4-chloromethyl-2-(3,4,5-trimethoxyphenyl)pyridine (881 mg) in chloroform (10 mL) was added potassium phthalimide (556 mg). The mixture was stirred at room temperature overnight and water was added. After separating the organic layer, the aqueous layer was extracted with chloroform. Organic layers were combined, dried over anhydrous magnesium sulfate and evaporated to give the title compound as white powder.

Yield: 1.16 g (96%).

PREPARATION EXAMPLE 5

Synthesis of 4-aminomethyl-2-(3,4,5-trimethoxyphenyl)pyridine:

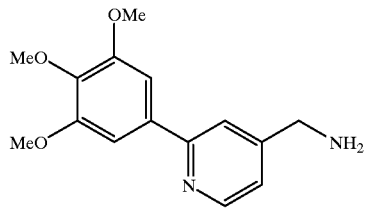

To a suspension of N-[[2-(3,4,5-trimethoxyphenyl)pyridin-4-yl]methyl]phthalimide (1.16 g) in ethanol (30 mL) was added hydrazine monohydrate (1 mL). The mixture was refluxed for 3 hours. After cooling, the precipitates were filtered off. The filtrate was evaporated and the residue was dissolved in chloroform. The solution was washed with saturated aqueous sodium hydrogen carbonate and brine, dried over anhydrous magnesium sulfate and evaporated to give the title compound as pale yellow oil.

Yield: 418 mg (53%).

PREPARATION EXAMPLE 6

Synthesis of ethyl 1-[[2-(3,4,5-trimethoxyphenyl)pyridin-4-yl]methyl]piperidine-4-carboxylate:

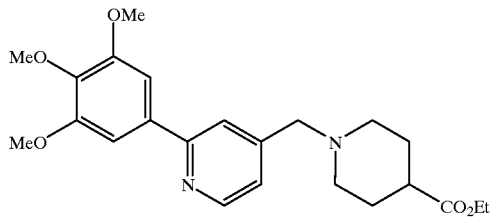

To a solution of ethyl piperidine-4-carboxylate (514 mg) and 4-chloromethyl-2-(3,4,5-trimethoxyphenyl)pyridine (969 mg) in acetonitrile (20 mL) was added potassium carbonate (452 mg). The mixture was stirred at room temperature for 4 hours and evaporated. The residual oil was subjected to a column of silica gel and eluted using hexane-ethyl acetate (2:1) and then chloroform-methanol (40:1). Fractions containing the product were collected and evaporated to give the title compound as white prisms.

Yield: 1.20 g (88%). $^1$H-NMR (400 MHz, CDCl$_3$): 1.25 (t, 3H, J=7.0 Hz), 1.72–1.93 (m, 4H), 2.10 (t, 2H, J=9.8 Hz), 2.27–2.35 (m, 1H), 2.86 (d, 2H, J=11.3 Hz), 3.55 (s, 2H), 3.91 (s, 3H), 3.98 (s, 6H), 4.14 (q, 2H, J=7.0 Hz), 7.21 (d, 1H, J=4.9 Hz), 7.24 (s, 2H), 7.63 (s, 1H), 8.59 (d, 1H, J=5.1 Hz).

PREPARATION EXAMPLE 7

Synthesis of 1-[[2-(3,4,5-trimethoxyphenyl)pyridin-4-yl]methyl]piperidine-4-carboxylic acid:

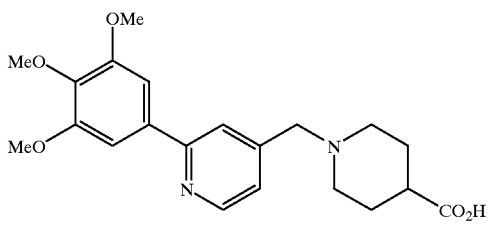

To a solution of ethyl 1-[[2-(3,4,5-trimethoxyphenyl)prydine-4-yl]methyl]piperidine-4-carboxylate (760 mg) in ethanol (10 mL) was added 1 M sodium hydroxide (10 mL). The mixture was stirred at room temperature for 4 hours and evaporated. The residue was dissolved in water (20 mL) and 5% aqueous potassium hydrogen sulfate was added dropwise until pH of the solution became 7. Precipitates were collected and the product was used for the next steps without further purification.

Yield: 779 mg (theoretical amount).

EXAMPLE 1

Synthesis of 1-[[2-(3,4,5-trimethoxyphenyl)pyridin-4-yl]methyl]-4-[[2-(3,4,5-trimethoxyphenyl)pyridin-4-yl]methylaminocarbonyl]piperidine maleate:

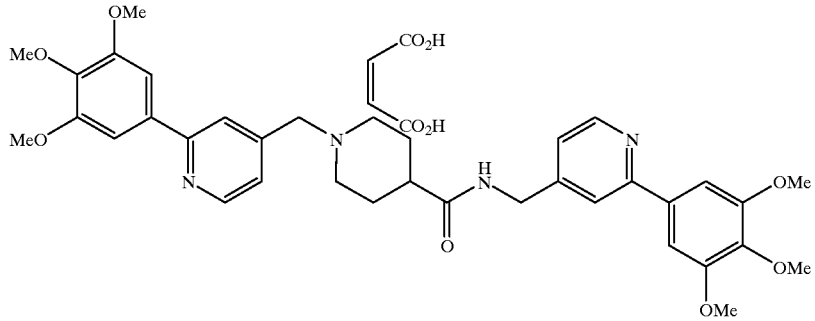

To a solution of 1-[[2-(3,4,5-trimethoxyphenyl)pyridin-4-yl]methyl]piperidine-4-caroxylic acid (97 mg) and 4-aminomethyl-2-(3,4,5-trimethoxyphenyl)pyridine (68 mg) in acetonitrile (5 mL) was added HBTU (95 mg). The mixture was stirred at room temperature for 12 hours and evaporated. The residual oil was dissolved in chloroform, washed with saturated aqueous sodium hydrogen carbonate and brine, dried over anhydrous magnesium sulfate and evaporated. Resulting residue was applied to a column of silica gel and eluted using chloroform-methanol (40:1) and then chloroform-methanol (20:1). Fractions containing the product were collected and evaporated. The free base of the product was then converted to a maleate by the usual method.

Yield: 93 mg (49%). $^1$H-NMR (400 MHz, measured as a maleate, DMSO-d$_6$): 1.87–2.01 (m, 4H), 2.48–2.56 (m, 1H), 2.78–2.86 (m, 2H), 3.26–3.31 (m, 2H), 3.78 (s, 3H), 3.79 (s, 3H), 3.87 (s, 6H), 3.90 (s, 6H), 4.15 (s, 2H), 4.39 (d, 2H, J=5.9 Hz), 6.16 (s, 2H), 7.16 (d, 1H, J=5.9 Hz), 7.35 (s, 2H), 7.39 (d, 1H, J=5.9 Hz), 7.39 (s, 2H), 7.73 (s, 1H), 7.95 (s, 1H), 8.15 (d, 1H, J=5.9 Hz), 8.54 (d, 1H, J=4.9 Hz), 8.68 (d, 1H, J=4.9 Hz).

PREPARATION EXAMPLE 8

Synthesis of 1-(benzyloxycarbonyl)-4-[[2-(3,4,5-trimethoxyphenyl)pyridin-4-yl]methyloxy]piperidine:

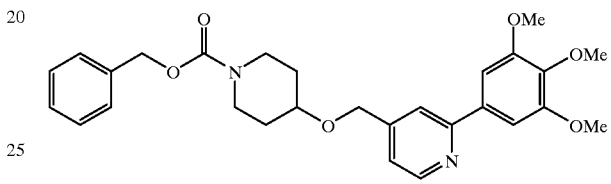

To a solution of 1-(benzyloxycarbonyl)-4-hydroxypiperidine (1.00 g) in DMF (20 mL) was added sodium hydride (55% dispersion in mineral oil, 222 mg). The mixture was stirred at room temperature for 1 hour and then, 4-chlolromethyl-2-(3,4,5-trimethoxyphenyl)pyridine (1.37 g) and potassium iodide (755 mg) was added. The mixture was stirred at 70° C. overnight, poured into water and extracted with chloroform. The organic layer was washed with brine, dried over anhydrous sodium sulfate and evaporated. The residual oil was applied to a column of silica gel and column chromatography was performed using chloroform-methanol (99:1) as an eluent giving the title compound.

Yield: 213 mg (10%). $^1$H NMR (400 MHz, CDCl$_3$): 1.63 (br, 2H), 1.89 (br, 2H), 3.20–3.35 (m, 2H), 3.57–3.68 (m, 1H), 3.84–3.92 (m, 5H), 3.94 (s, 6H), 4.62 (s, 2H), 5.11 (s, 2H), 7.21–7.35 (m, 8H), 7.61 (s, 1H), 8.61 (d, 1H, J=5.0 Hz).

PREPARATION EXAMPLE 9

Synthesis of 4-[[2-(3,4,5-trimethoxyphenyl)pyridin-4-yl]methyloxy]piperidine:

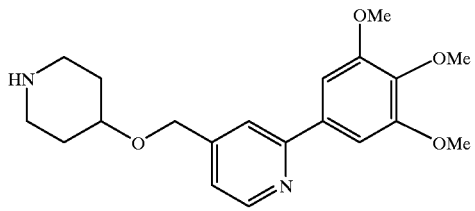

To a solution of 1-(benzyloxycarbonyl)-4-[[2-(3,4,5-trimethoxyphenyl)pyridin-4-yl]methyloxy]piperidine (213 mg) in methanol (10 mL) was added 40% aqueous potassium hydroxide (10 mL). The mixture was stirred at 100° C. for 3 hours and evaporated. Water was added to the residue and extracted with chloroform. The organic layer was washed with brine, dried over anhydrous sodium sulfate and evaporated. The residual oil was subjected to column chromatography of silica gel using chloroform-ammonia saturated methanol (20:1) to give the title compound.

Yield: 93 mg (60%). $^1$H NMR (400 MHz, CDCl$_3$): 1.55–1.68 (m, 2H), 2.01 (br, 2H), 2.67–2.72 (m, 2H), 3.13–3.18 (m, 2H), 3.50–3.60 (m, 1H), 3.91 (s, 3H), 3.97 (s, 6H), 4.64 (s, 2H), 7.22 (d, 1H, J=4.3 Hz), 7.24 (s, 2H), 7.64 (s, 1H), 8.63 (d, 1H, J=5.1 Hz).

EXAMPLE 2
Synthesis of 1-[2-[(3,4,5-trimethoxyphenyl)pyridin-4-yl]methyl]-4-[[2-(3,4,5-trimethoxyphenyl)pyridin-4-yl]methyloxy]piperidine trihydrochloride:

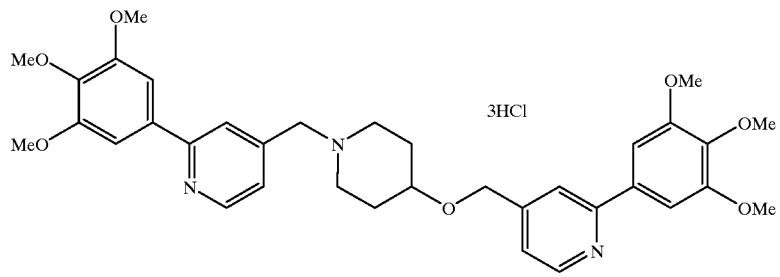

4-[[2-(3,4,5-trimethoxyphenyl)pyridin-4-yl]methyloxy]piperidine (70 mg), 4-chloromethyl-2-(3,4,5-trimethoxyphenyl)pyridine (22 mg), potassium carbonate (56 mg) and potassium iodide (40 mg) were suspended in acetonitrile (5 mL). The mixture was stirred at room temperature for 5 hr and evaporated. Chloroform and water were added to the residual oil and the organic layer was separated. Aqueous layer was then extracted with chloroform and the organic layers were combined, dried over anhydrous magnesium sulfate and evaporated. The residue was applied to a column of silica gel using chloroform-methanol (40:1) as an eluent. Fractions containing the product were collected and evaporated. The title compound was obtained by converting the free base to a trihydrochloride.

Yield: 42 mg (39%). $^1$H NMR (400 MHz, measured as a free base, CDCl$_3$): 1.53–2.42 (m, 6H), 2.80 (br, 2H), 3.57 (br, 3H), 3.88 (s, 6H), 3.94 (s, 6H), 3.95 (s, 6H), 4.60 (s, 2H), 7.18–7.24(m, 6H), 7.61 (s, 2H), 8.58–8.61 (m, 2H).

PREPARATION EXAMPLE 10
Synthesis of (3S)-1-(tert-butoxycarbonyl)-3-[(2-nitrobenzene)sulfonylamino]pyrrolidine:

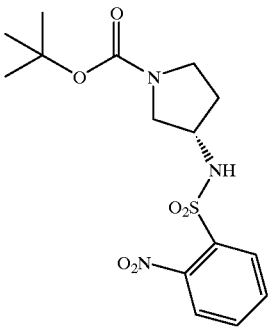

To an ice-cooled solution of(3S)-3-amino-1-(tert-butoxycarbonyl)pyrrolidine (404 mg) and triethylamine (220 mg) in THF (5 mL) was added 2-nitrobenzenesulfonyl chloride (481 mg). The mixture was stirred at room temperature for 30 minutes and evaporated. Ethyl acetate was added to the residue. The solution was washed with water and brine, dried over anhydrous sodium sulfate and evaporated. The residual oil was subjected to a column of silica gel and column chromatography was performed using chloroform-methanol (20:1) as an eluent. Fractions containing the product were collected and evaporated to give the title compound as pale yellow amorphous.

Yield: 597 mg (74%). $^1$H-NMR (400 MHz, CDCl$_3$): 1.44 (s, 9H), 1.80–2.12 (m, 2H), 3.14–3.44 (m, 4H), 4.02 (br, 1H), 5.48 (d, 1H, J=7.2 Hz), 7.77 (t, 2H, J=4.4 Hz), 7.87–7.90 (m, 1H), 8.17–8.19 (m, 1H).

PREPARATION EXAMPLE 11
Synthesis of (3S)-1-(tert-butoxycarbonyl)-3-[N-methyl-N-(2-nitrobenzene)sulfonylamino]pyrrolidine:

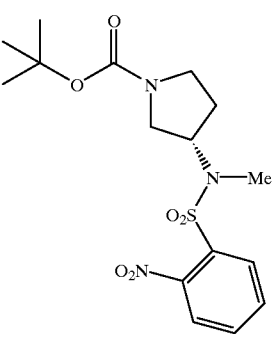

To a suspension of (3S)-1-(tert-butoxycarbonyl)-3-[(2-nitrobenzene)sulfonylamino]pyrrolidine (371 mg) and potassium carbonate (141 mg) in acetonitrile (10 mL) was added methyl iodide (141 mg). The mixture was stirred at 60° C. for 2 hours and evaporated. Ethyl acetate was added to the mixture. The solution was washed with saturated aqueous sodium hydrogen carbonate and brine, dried over anhydrous sodium sulfate and evaporated. The residue was applied to a column of silica gel using hexane-ethyl acetate (2:1) as an eluent. Fractions containing the product were collected and evaporated to give the title compound as yellow syrup.

Yield: 365 mg (95%). $^1$H-NMR (400 MHz, CDCl$_3$): 1.44 (s, 9H), 1.95 (br, 1H), 2.09 (br, 1H), 2.87 (s, 3H), 3.20–3.31 (m, 2H), 3.53 (br, 2H), 4.58 (br, 1H), 7.65 (br, 1H), 7.71 (br, 2H), 8.04 (br, 1H).

PREPARATION EXAMPLE 12
Synthesis of (3S)-3-[N-methyl-N-(2-nitrobenzene) sulfonylamino]pyrrolidine:

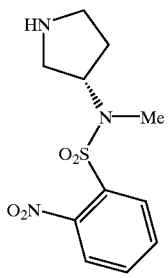

To an ice-cooled solution of (3S)-1-(tert-butoxycarbonyl)-3-[N-methyl-N-(2-nitrobenzenesulfonyl) amino]pyrrolidine (365 mg) in dichloromethane (25 mL) was added trifluoroacetic acid (1 mL). The mixture was stirred at room temperature for 3 hours and evaporated. The residue was dissolved in chloroform. The solution was washed with saturated aqueous sodium hydrogen carbonate and brine, dried over anhydrous sodium sulfate and evaporated to give the title compound as yellow syrup.

Yield: 135 mg (50%). $^1$H-NMR (400 MHz, CDCl$_3$): 1.69–1.74 (m, 1H), 1.87 (br, 1H), 1.95–2.02 (m, 1H), 2.80 (dd, 1H, J=11.7 Hz, 5.7 Hz), 2.84–2.91 (m, 4H), 2.96–3.05 (m, 1H), 3.10 (dd, 1H, J=11.7 Hz, 8.2 Hz), 4.48–4.56 (m, 1H), 7.61–7.63 (m, 1H), 7.66–7.73 (m, 2H), 8.01–8.04 (m, 1H).

PREPARATION EXAMPLE 13
Synthesis of (3S)-3-[N-methyl-N-(2-nitrobenzene) sulfonylamino]-1-[[2-(3,4,5-trimethoxyphenyl)pyridin-4-yl]methyl]pyrrolidine:

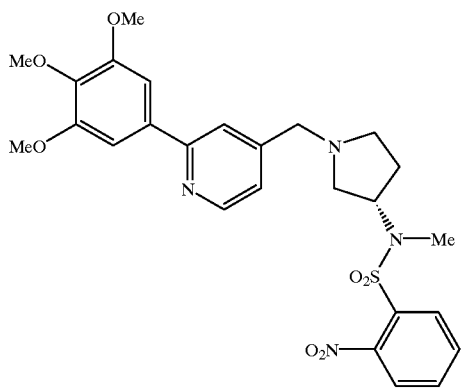

(3S)-3-[N-methyl-N-(2-nitrobenzene)sulfonylamino] pyrrolidine (135 mg) and 4-chloromethyl-2-(3,4,5-trimethoxyphenyl)pyridine (139 mg) were coupled in the same manner as described in Example 2 to give the title compound as yellow amorphous.

Yield: 247 mg (96%). $^1$H-NMR (400 MHz, CDCl$_3$): 1.80–1.87 (m, 1H), 2.15–2.30 (m, 2H), 2.52 (dd, 1H, J=10.5 Hz, 8.2 Hz), 2.71 (dd, 1H, J=10.5 Hz, 8.2 Hz), 2.90 (dt, 1H, J=8.8 Hz, 2.9 Hz), 2.96 (s, 3H), 3.53 (d, 1H, J=13.9 Hz), 3.68 (d, 1H, J=13.9 Hz), 3.90 (s, 3H), 3.96 (s, 6H), 4.61–4.68 (m, 1H), 7.16 (dd, 1H, J=4.9 Hz, 1.2 Hz), 7.21 (s, 2H), 7.58–7.60 (m, 2H), 7.64–7.69 (m, 2H), 7.99–8.02 (m, 1H), 8.58 (d, 1H, J=4.9 Hz,).

PREPARATION EXAMPLE 14
Synthesis of (3S)-3-methylamino-1-[[2-(3,4,5-trimethoxyphenyl)-pyridin-4-yl]methyl]pyrrolidine:

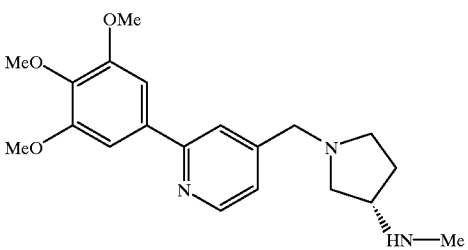

To a solution of (3S)-3-[N-methyl-N-(2-nitrobenzene) sulfonylamino]-1-[[2-(3,4,5-trimethoxyphenyl)pyridin-4-yl]methyl]pyrrolidine (242 mg) in acetonitrile (5 mL) was added potassium carbonate (94 mg) and thiophenol (75 mg). The mixture was stirred at 80° C. for 3 hours and evaporated. Ethyl acetate was added to the mixture, the solution was washed with saturated aqueous sodium hydrogen carbonate, water, and brine, dried over anhydrous sodium sulfate and evaporated. The residual oil was subjected to preparative TLC using chloroform-methanol (20:1) as a solvent system giving yellow syrup of the title compound.

Yield: 104 mg (64%). $^1$H-NMR (400 MHz, CDCl$_3$): 1.32 (br, 1H), 1.56–1.64 (m, 1H), 2.11–2.17 (m, 1H), 2.38 (s, 3H), 2.44 (dd, 1H, J=7.4 Hz, 4.5 Hz), 2.50–2.55 (m, 1H), 2.66–2.75 (m, 2H), 3.20–3.26 (m, 1H), 3.66 (s, 2H), 3.90 (s, 3H), 3.97 (s, 6H), 7.21 (d, 1H, J=4.1 Hz), 7.25 (s, 2H), 7.64 (s, 1H), 8.59 (d, 1H, J=4.9 Hz).

EXAMPLE 3
Synthesis of (3S)-3-[N-methyl-N-[[2-(3,4,5-trimethoxyphenyl)pyridin-4-yl]methyl]amino]-1-[[2-(3,4,5-trimethoxyphenyl)pyridin-4-yl]methyl]pirrolidine tetrahydrochloride.

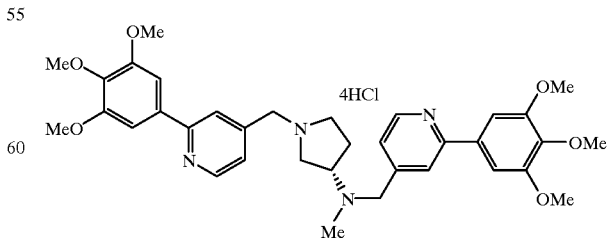

(3S)-3-methylamino-1-[[2-(3,4,5-trimethoxyphenyl) pyridin-4-yl]methyl]pyrrolidine (104 mg) and 4-chloromethyl-2-(3,4,5-trimethoxyphenyl)pyridine (85 mg) was condensed in the same manner as described in Example 2. Yellow syrup obtained was converted to a tetrahydrochloride by the usual method giving the title compound as yellow powder.

Yield: 151 mg (68%). $^1$H-NMR (400 MHz, measured as a free base, CDCl$_3$): 1.89–1.92 (m, 1H), 2.04–2.08 (m, 1H), 2.18 (s, 3H), 2.60–2.76 (m, 4H), 3.25–3.29 (m, 1H), 3.53 (d, 1H, J=14.3 Hz), 3.62 (d, 1H, J=14.3 Hz), 3.64 (d, 1H, J=13.9 Hz), 3.73 (d, 1H, J=13.9 Hz), 3.89 (s, 6H), 3.95 (s, 6H), 3.96 (s, 6H), 7.20–7.21 (m, 2H), 7.23 (s, 2H), 7.24 (s, 2H), 7.61 (s, 1H), 7.65 (s, 1H), 8.59 (d, 1H, J=5.7 Hz), 8.60 (d, 1H, J=5.3 Hz).

PREPARATION EXAMPLE 15

Synthesis of 1-[[2-(3,4,5-trimethoxyphenyl)pyridin-4-yl]methyl]piperidine-4-carboxamide:

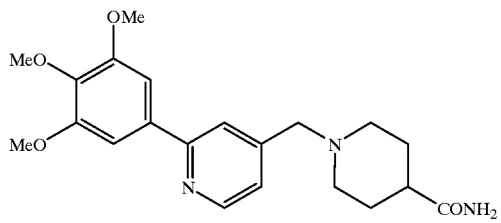

Piperidine-4-carboxamide (385 mg) and 4-chloromethyl-2-(3,4,5-trimethoxyphenyl)pyridine (881 mg) were condensed by the same method as described in Example 2 to give the title compound as white needles.

Yield: 1.01 g (87%). $^1$H-NMR (400 MHz, CDCl$_3$): 1.70–1.88 (m, 4H), 2.01–2.23 (m, 3H), 2.95 (d, 2H, J=11.0 Hz), 3.56 (s, 2H), 3.90 (s, 3H), 3.98 (s, 6H), 5.46 (d, 2H, J=16.3 Hz), 7.21 (d, 1H, J=5.0 Hz), 7.24 (s, 2H), 7.64 (s, 1H), 8.59 (d, 1H, J=5.0 Hz).

PREPARATION EXAMPLE 16

Synthesis of 4-amino-1-[[2-(3,4,5-trimethoxyphenyl)pyridin-4-yl]methyl]piperidine trihydrochloride:

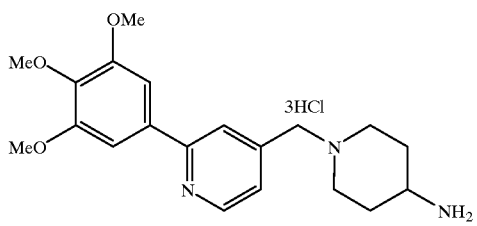

To a solution of 1-[[2-(3,4,5-trimethoxyphenyl)pyridin-4-yl]methyl]piperidine-4-carboxamide (192 mg) in a mixed solvent of water (50 mL) and acetonitrile (50 mL) was added [bis(trifluoroacetoxy)iodo]benzene (323 mg). The mixture was stirred at room temperature overnight and evaporated. Saturated aqueous sodium hydrogen carbonate was added to the residue and extracted with chloroform. The organic layer was washed with brine, dried over anhydrous magnesium sulfate and evaporated. Yellow syrup obtained was then converted to trihydrochloride which gave yellow powder. The title compound was used for next step without further purification.

Yield: 201 mg (theoretical amount).

PREPARATION EXAMPLE 17

Synthesis of 2-(3,4,5-trimethoxyphenyl)isonicotinic acid:

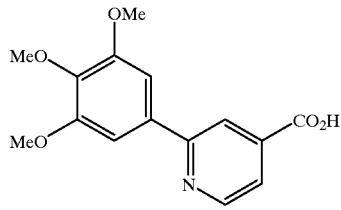

To a solution of ethyl 2-(3,4,5-trimethoxyphenyl)isonicotinate (3.17 g) in ethanol (40 mL) was added 10% potassium hydroxide (2.42 g). The mixture was stirred at room temperature for 5 hours and evaporated. Water was added to the residue and pH was adjusted to 7. White precipitates of the title compound were collected by filtration and the compound was used for next step without further purification.

Yield: 2.60 g (90%).

EXAMPLE 4

Synthesis of 4-[2-(3,4,5-trimethoxyphenyl)pyridin-4-carbonylamino]-1-[[2-(3,4,5-trimethoxyphenyl)pyridin-4-yl]methyl]piperidine maleate:

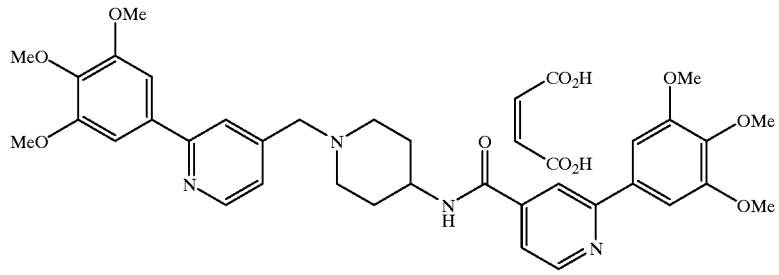

2-(3,4,5-trimethoxyphenyl)isonicotinic acid (72 mg) and 4-amino-1-[[2-(3,4,5-trimethoxyphenyl)pyridin-4-yl]methyl]piperidine (117 mg) were condensed in the same manner as described in Example 1. The title compound was obtained as a maleate.

Yield: 173 mg (93%). $^1$H-NMR (400 MHz, measured as a maleate, DMSO-$d_6$): 1.82–1.94 (m, 2H), 2.03–2.08 (m, 2H), 2.77–2.83 (m, 2H), 3.20–3.27 (m, 2H), 3.79 (s, 6H), 3.90 (s, 12H), 4.00 (br, 1H), 4.06 (s, 2H), 6.15 (s, 2H), 7.36–7.38 (m, 1H), 7.39 (s, 2H), 7.41 (s, 2H), 7.61–7.63 (m, 1H), 7.90 (s, 1H), 8.12 (s, 1H), 8.27–8.32 (m, 1H), 8.67 (d, 1H, J=4.9 Hz), 8.74 (d, 1H, J=5.1 Hz).

PREPARATION EXAMPLE 18

Synthesis of 4-[(2-nitrobenzene)sulfonylamino]-1-[[2-(3,4,5-trimethoxyphenyl)pyridin-4-yl]methyl]piperidine:

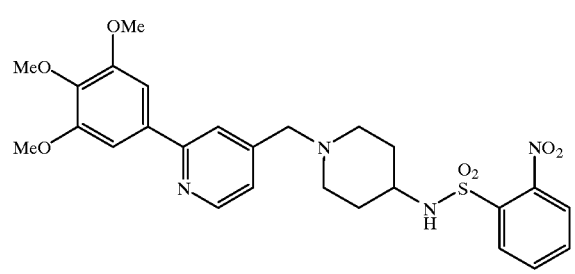

4-amino-1-[[2-(3,4,5-trimethoxyphenyl)pyridin-4-yl]methyl]piperidine (467 mg) and 2-nitrobenzenesulfonyl chloride (244 mg) were condensed in the same manner as described in Preparation Example 10 to give the title compound.

Yield: 494 mg (91%).

PREPARATION EXAMPLE 19

Synthesis of 4-[N-(2-nitrobenzene)sulfonyl-N-[[2-(3,4,5-trimethoxyphenyl)pyridin-4-yl]methyl]amino]-1-[[2-(3,4,5-trimethoxyphenyl)pyridin-4-yl]methyl]piperidine:

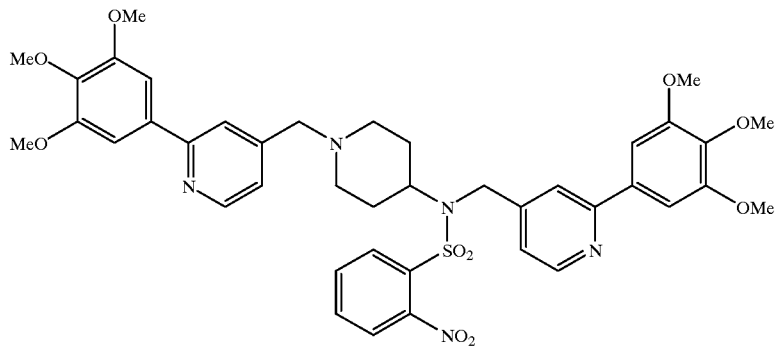

4-[(2-nitrobenzene)sulfonylamino]-1-[[2-(3,4,5-trimethoxyphenyl)pyridin-4-yl]methyl]piperidine (494 mg) and 4-chloromethyl-2-(3,4,5-trimethoxyphenyl)pyridine (267 mg) were condensed in the same manner as described in Example 2 to give the title compound.

Yield: 443 mg (61%).

EXAMPLE 5

Synthesis of 1-[[2-(3,4,5-trimethoxyphenyl)pyridin-4-yl]methyl]-4-[[2-(3,4,5-trimethoxyphenyl)pyridin-4-yl]methylamino]piperidine difumalate:

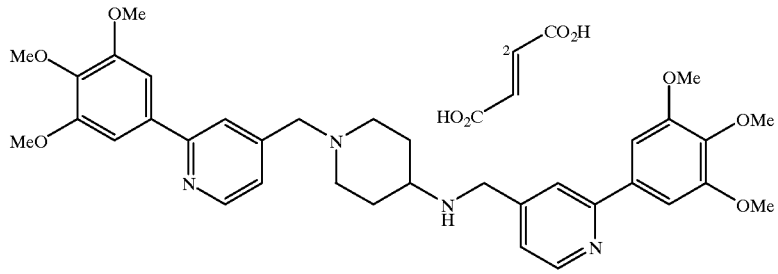

4-[N-(2-nitrobenzene)sulfonyl-N-[[2-(3,4,5-trimethoxyphenyl)pyridin-4-yl]methyl]amino]-1-[[2-(3,4,5-trimethoxyphenyl)pyridin-4-yl]methyl]piperidine (443 mg) was treated in the same manner as described in Preparation Example 14. The title compound was obtained after converting to a difumalate.

Yield: 103 mg (24%). $^1$H-NMR (400 MHz, measured as a free base, CDCl$_3$): 1.44–1.53 (m, 2H), 1.87–1.91 (m, 2H), 2.15 (t, 2H, J=1.1 Hz), 2.57–2.64 (m, 1H), 2.82–2.85 (m, 2H), 3.59 (s, 2H), 3.78 (s, 6H), 3.89 (s, 12H), 3.90 (s, 2H), 6.63 (s, 4H), 7.24 (d, 1H, J=4.9 Hz), 7.29 (d, 1H, J=4.9 Hz), 7.35 (s, 2H), 7.37 (s, 2H), 7.76 (s, 1H), 7.85 (s, 1H), 8.53–8.56 (m, 2H).

PREPARATION EXAMPLE 20

Synthesis of 4-(ethoxycarbonylamino)-1-[[2-(3,4,5-trimethoxyphenyl)pyridin-4-yl]methyl]piperidine:

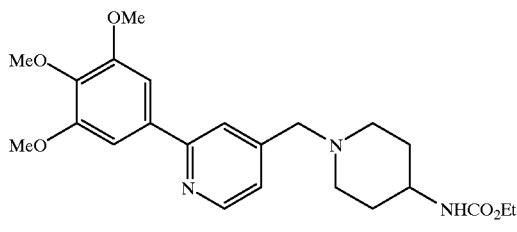

To a solution of 1-[[2-(3,4,5-trimethoxyphenyl)pyridin-4-yl]methyl]piperidine-4-carboxamide (528 mg) in a mixed solvent of ethanol (10 mL) and acetonitrile (10 mL) was added [bis(trifluoroacetoxy)iodo]benzene (884 mg). The mixture was stirred at room temperature overnight and evaporated. Saturated aqueous sodium hydrogen carbonate was added to the residue and extracted with chloroform. The organic layer was washed with brine, dried over anhydrous magnesium sulfate and evaporated. The residue was applied to a column of silica gel and purified using chloroform-methanol (20:1) as an eluent to give the title compound.

Yield: 566 mg (96%). $^1$H-NMR (400 MHz, CDCl$_3$): 1.21 (t, 3H, J=7.0 Hz), 1.40–1.51 (m, 2H), 1.92 (d, 2H, J=10.9 Hz), 2.15 (t, 2H, J=10.9 Hz), 2.78 (d, 2H, J=11.6 Hz), 3.52 (br, 3H), 3.87 (s, 3H), 3.94 (s, 6H), 4.07 (q, 2H, J=7.0 Hz), 4.56 (br, 1H), 7.17 (d, 1H, J=4.9 Hz), 7.21 (s, 2H), 7.59 (s, 1H), 8.56 (d, 1H, J=5.1 Hz).

PREPARATION EXAMPLE 21

Synthesis of 4-(methylamino)-1-[[2-(3,4,5-trimethoxyphenyl)pyridin-4-yl]methyl]piperidine:

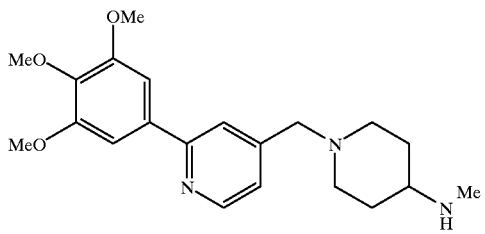

To a suspension of lithium aluminum hydride (100 mg) in dry THF (50 mL) was added a solution of 4-(ethoxycarbonylamino)-1-[[2-(3,4,5-trimethoxyphenyl)pyridin-4-yl]methyl]piperidine (566 mg) in dry THF (5 mL) under an argon atmosphere. The mixture was then refluxed overnight, then cooled down. Saturated aqueous ammonium chloride was added to the mixture and extracted with ethyl acetate. The organic layer was washed with brine, dried over anhydrous sodium sulfate and evaporated. The residue was subjected to silica gel column chromatography using chloroform-ammonia saturated methanol (9:1) to give the title compound as yellow oil.

Yield: 379 mg (78%). $^1$H-NMR (400 MHz, CDCl$_3$): 1.36–1.46 (m, 2H), 1.89 (d, 2H, J=12.5 Hz), 2.10 (dt, 2H, J=11.5 Hz, 1.1 Hz), 2.35–2.43 (m, 1H), 2.43 (s, 3H), 2.86 (d, 2H, J=11.6 Hz), 3.56 (s, 2H), 3.90 (s, 3H), 3.97 (s, 6H), 7.21 (d, 1H, J=5.1 Hz), 7.24 (s, 2H), 7.64 (s, 1H), 8.59 (d, 1H, J=4.9 Hz).

PREPARATION EXAMPLE 22

Synthesis of 1-[[2-(3,4,5-trimethoxyphenyl)pyridin-4-yl]methyl]-4-piperidone ethylene ketal:

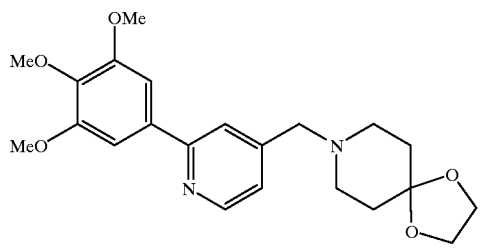

4-Piperidone ethylene ketal (12.0 g) and 4-chloromethyl-2-(3,4,5-trimethoxyphenyl)pyridine (12.3 g) was condensed in the same manner as described in Example 2 to give the title compound.

Yield: 19.0 g (theoretical amount). $^1$H-NMR (400 MHz, CDCl$_3$): 1.68 (t, 4H, J=5.6 Hz), 2.48 (br, 4H), 3.50 (s, 2H), 3.82 (s, 3H), 3.86 (s, 4H), 3.88 (s, 6H), 7.13 (d, 1H, J=4.9 Hz), 7.17 (s, 2H), 7.57 (s, 1H), 8.51 (d, 1H, J=4.9 Hz).

PREPARATION EXAMPLE 23

Synthesis of 1-[[2-(3,4,5-trimethoxyphenyl)pyridin-4-yl]methyl]-4-piperidone:

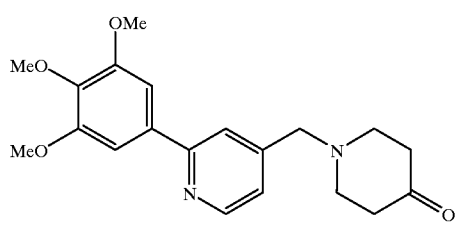

To a solution of 1-[[2-(3,4,5-trimethoxyphenyl)pyridin-4-yl]methyl]-4-piperidone ethylene ketal (19.0 g) in THF (200 mL) was added 1 M hydrochloric acid (200 mL). The mixture was stirred at 90° C. overnight, then neutralized with 2 M sodium hydroxide and extracted with ethyl acetate. The organic layer was washed with brine, dried over anhydrous sodium sulfate and evaporated. The residual oil was applied to a column of silica gel using chloroform-methanol (40:1) as an eluent. Fractions containing the product were collected and evaporated to give the title compound.

Yield: 15.0 g (75%). $^1$H-NMR (400 MHz, CDCl$_3$): 2.48 (t, 4H, J=6.1 Hz), 2.79 (t, 4H, J=6.0 Hz), 3.69 (s, 2H), 3.89 (s, 3H), 3.96 (s, 6H), 7.24 (s, 2H), 7.26 (d, 1H, J=4.9 Hz), 7.66 (s, 1H), 8.62 (d, 1H, J=4.9 Hz).

PREPARATION EXAMPLE 24

Synthesis of 1-[[2-(3,4,5-trimethoxyphenyl)pyridin-4-yl]methyl]-4-piperidone:

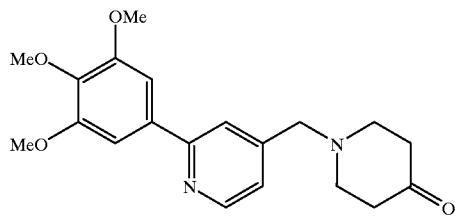

4-Piperidone hydrochloride monohydrate (3.07 g) and 4-chloromethyl-2-(3,4,5-trimethoxyphenyl)pyridine (2.94 g) were coupled by the same manner as described in Example 2 to give the title compound.

Yield: 3.55 g (99%).

PREPARATION EXAMPLE 25
Synthesis of 4-(methylamino)-1-[[2-(3,4,5-trimethoxyphenyl)pyridin-4-yl]methyl]piperidine:

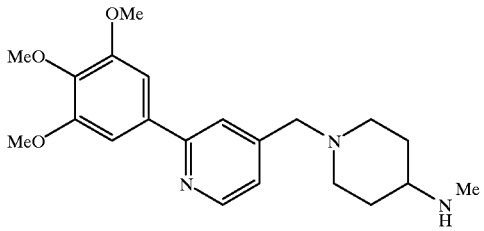

To a solution of 1-[[2-(3,4,5-trimethoxyphenyl)pyridin-4-yl]methyl]-4-piperidone (1.00 g) in 1,2-dichloroethane (60 mL) was added 30% solution of methylamine in ethanol (750 mg) and sodium triacetoxyborohydride (1.66 g). The mixture was stirred at room temperature for 3 hours, then small amount of water was added and evaporated. Water was added to the residue and extracted with chloroform. The organic layer was washed with brine, dried over anhydrous sodium sulfate and evaporated. The residue was subjected to silica gel column chromatography using chloroform-methanol (40:1) to give the title compound.

Yield: 640 mg (62%).

PREPARATION EXAMPLE 26
Synthesis of ethyl 3-(3,4,5-trimethoxyphenyl)benzoate:

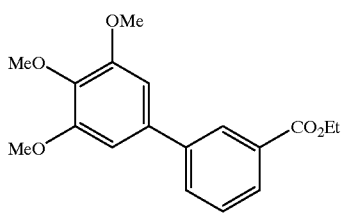

3,4,5-Trimethoyphenylboronic acid (3.7 g) and ethyl 3-bromobenzoate (4.02 g) were condensed in the same manner as described in Preparation Example 1 to give the title compound.

Yield: 5.09 g (92%). $^1$H-NMR (400 MHz, CDCl$_3$): 1.42 (t, 3H, J=7.1 Hz), 3.90 (s, 3H), 3.94 (s, 6H), 4.41 (q, 2H, J=7.1 Hz), 6.79 (s, 2H), 7.50 (t, 1H, J=7.8 Hz), 7.73 (dt, 1H, J=7.1 Hz, 1.5 Hz), 8.01 (dt, 1H, J=7.8 Hz, 1.4 Hz), 8.23 (t, 1H, J=1.8 Hz).

PREPARATION EXAMPLE 27
Synthesis of 3-(3,4,5-trimethoxyphenyl)benzoic acid:

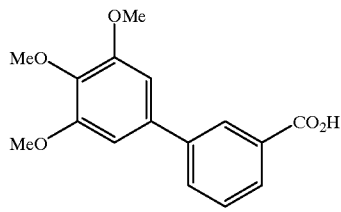

Ethyl 3-(3,4,5-trimethoxyphenyl)benzoate (1.19 g) was treated in the same manner as described in Preparation Example 17 to give the title compound.

Yield: 986 mg (91%).

EXAMPLE 6
Synthesis of 4-[N-methyl-N-[3-(3,4,5-trimethoxyphenyl)]benzoylamino]-1-[[2-(3,4,5-trimethoxyphenyl)pyridin-4-yl]methyl]piperidine dihydrochloride:

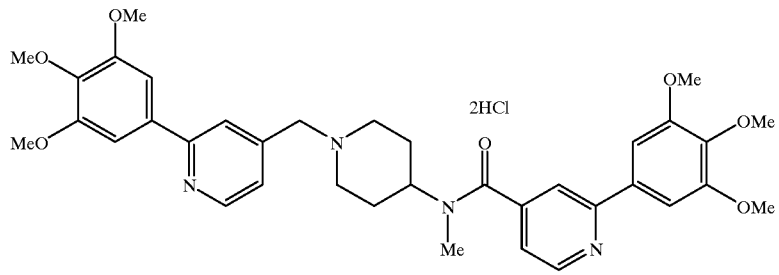

3-(3,4,5-trimethoxyphenyl)benzoic acid (1.03 g) and 4-(methylamino)-1-[[2-(3,4,5-trimethoxyphenyl)pyridin-4-yl]methyl]piperidine (1.32 g) were condensed in the same method as described in Example 1. The title compound was obtained after converting a free amine to a dihydrochloride.

Yield: 1.44 g (57%). $^1$H-NMR (400 MHz, measured as a dihydrochloride, DMSO-d$_6$): 1.89 (d, 2H, J=11.7 Hz), 2.54–2.62 (m, 2H), 2.89 (s, 3H), 3.09 (t, 2H, J=12.7 Hz), 3.43 (d, 2H, J=14.4 Hz), 3.76 (s, 3H), 3.78 (s, 3H), 3.88 (s, 6H), 3.91 (s, 6H), 4.34 (br, 3H), 6.91 (s, 2H), 7.33 (d, 1H, J=7.6 Hz), 7.47–7.51 (m, 2H), 7.54 (s, 2H), 7.60 (s, 1H), 7.71 (d, 1H, J=7.8 Hz), 8.55 (s, 1H), 8.68 (d, 1H, J=5.1 Hz).

EXAMPLE 7
Synthesis of 4-[N-methyl-N-[[5-(3,4,5-trimethoxyphenyl)pyridin-3-yl]methyl]amino]-1-[[2-(3,4,5-trimethoxyphenyl)pyridin-4-yl]methyl]piperidine difumarate:

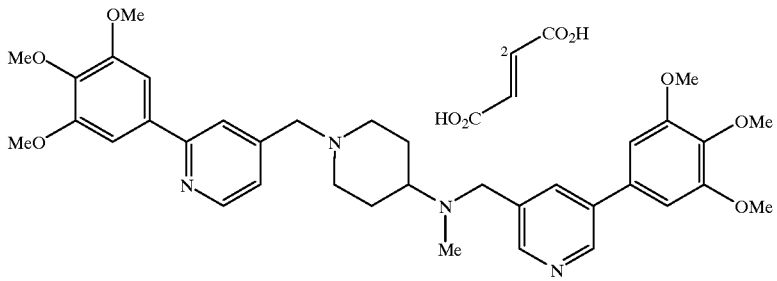

4-methylamino-1-[[2-(3,4,5-trimethoxyphenyl)pyridin-4-yl]methyl]piperidine (135 mg) and 3-chloromethyl-5-(3,4,5-trimethoxyphenyl)pyridine (107 mg) were condensed by the same method as described in Example 2. White powder of the title compound was obtained after converting a free base to a difumarate.

Yield: 180 mg (58%). $^1$H-NMR (400 MHz, measured as a free base, CDCl$_3$): 1.69–1.73 (m, 2H), 1.82–1.85 (m, 2H), 2.03–2.08 (m, 2H), 2.25 (s, 3H), 2.48–2.51 (m, 1H), 2.97–2.99 (m, 2H), 3.56 (s, 2H), 3.67 (s, 2H), 3.90 (s, 3H), 3.91 (s, 3H), 3.94 (s, 6H), 3.98 (s, 6H), 6.76 (s, 2H), 7.22 (d, 1H, J=5.1 Hz), 7.24 (s, 2H), 7.62 (s, 1H), 7.80 (s, 1H), 8.50 (d, 1H, J=2.0 Hz), 8.60 (d, 1H, J=4.3 Hz), 8.69 (d, 1H, J=5.1 Hz).

PREPARATION EXAMPLE 28
Synthesis of 1-bromo-4-chloro-3,5-dimethoxybenzene:

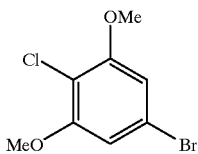

A solution of sodium nitrite (97 mg) in water (2.0 mL) was added dropwise to an ice-cold suspension of 4-bromo-2,6-dimethoxyaniline (232 mg) in 6.0 M hydrochloric acid (2.5 mL). After stirring in ice for 30 minutes, a solution of cupric chloride (495 mg) in concentrated hydrochloric acid (2.0 mL) was added. The reaction mixture was stirred at room temperature for 30 minutes, then at 100° C. for 2 hours, and extracted with ethyl acetate. The organic layer was washed with a saturated aqueous sodium hydrogencarbonate and water, dried over anhydrous sodium sulfate, and evaporated. The residue was subjected to a column of silica gel using hexane-ethyl acetate (10:1) as an eluent to give the title compound as white powder.

Yield: 230 mg (92%).

PREPARATION EXAMPLE 29
Synthesis of 4-chloro-3,5-dimethoxyphenylboronic acid:

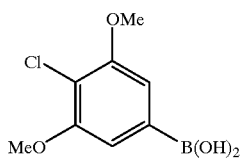

Under an argon atomsphere, to dry THF (2 mL) stirred in a dry ice-methanol bath was gradually added a 1.57 M solution of n-butyllithium in hexane (0.8 mL), followed by the dropwise addition of a solution of 1-bromo-4-chloro-3,5-dimethoxybenzene (160 mg) in dry THF (2 mL). After the mixture was stirred for 20 minutes in the dry ice-methanol bath, triisopropyl borate (0.18 mL) was added and the mixture was additionally stirred for 20 minutes. The reaction mixture was then stirred at room temperature for 1 hour and pH of the mixture was adjusted at 3 using 4 M hydrochloric acid. The mixture was stirred at 0° C. for 1 hour and extracted with ethyl acetate. The organic layer was washed with brine, dried over anhydrous sodium sulfate and evaporated. The residue was recrystallized from ethyl acetate-hexane giving the title compound as white powder.

Yield: 90 mg (66%).

PREPARATION EXAMPLE 30
Synthesis of ethyl 2-(4-chloro-3,5-dimethoxyphenyl)isonicotinate:

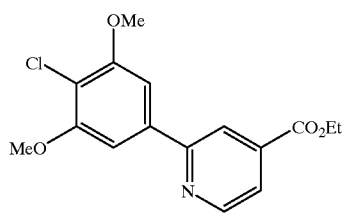

4-Chloro-3,5-dimethoxyphenylboronic acid (7.45 g) and ethyl 2-chloroisonicotinate (6.39 g) were condensend in the same manner as described in Preparation Example 1 to give the title compound.

Yield: 8.55 g (77%). $^1$H-NMR (400 MHz, CDCl$_3$): 1.45 (t, 3H, J=7.3 Hz), 4.03 (s, 6H), 4.45 (q, 2H, J=7.3 Hz), 7.32 (s, 2H), 7.80 (d, 1H, J=5.1 Hz), 8.27 (s, 1H), 8.83 (d, 1H, J=5.0 Hz).

PREPARATION EXAMPLE 31
Synthesis of 2-(4-chloro-3,5-dimethoxyphenyl)isonicotinic acid:

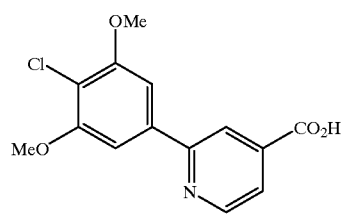

To a solution of ethyl 2-(4-chloro-3,5-dimethoxyphenyl)isonicotinate (8.55 g) in ethanol (80 mL) was added 2 M sodium hydroxide (100 mL). The mixture was refluxed for 30 min and evaporated. The aqueous layer was neutralized by 1 M hydrochloric acid and precipitates were dissolved in a mixed solvent of ethyl acetate-THF (3:1). After drying over anhydrous sodium sulfate, the solvent was evaporated to give the title compound.

Yield: 7.20 g (92%). $^1$H-NMR (400 MHz, CDCl$_3$): 4.02 (s, 6H), 7.34 (s, 2H), 7.83 (d, 1H, J=4.9 Hz), 7.84 (s, 1H), 8.82 (d, 1H, J=4.9 Hz).

PREPARATION EXAMPLE 32

Synthesis of 2-(4-chloro-3,5-dimethoxyphenyl)-4-hydroxymethylpyridine:

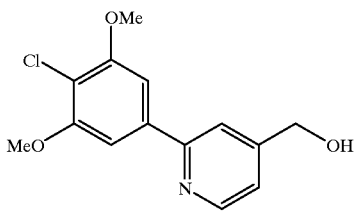

To an ice-cooled solution of 2-(4-chloro-3,5-dimethoxyphenyl)isonicotinic acid (7.20 g) and triethylamine (5.6 mL) in THF (70 mL) was added ethyl chloroformate (2.8 mL). The mixture was stirred at room temperature for 1 hour and filtered. To the filtrate was then added a solution of sodium borohydride (1.25 g) in water (4 mL). The mixture was stirred at room temperature for another hour and evaporated. Water was added to the residue and extracted with chloroform. The organic layer was washed with brine, dried over anhydrous sodium sulfate and evaporated. The residue was subjected to silica gel column chromatography using chloroform-methanol (20:1) and then chloroform-methanol (15:1) to give the title compound.

Yield: 4.10 g (60%). $^1$H-NMR (400 MHz, CDCl$_3$+ DMSO-d$_6$): 4.01 (s, 6H), 4.76 (s, 2H), 7.20–7.35 (m, 3H), 7.78 (s, 1H), 8.62 (s,1H).

PREPARATION EXAMPLE 33

Synthesis of 2-(4-chloro-3,5-dimethoxyphenyl)-4-chloromethylpyridine:

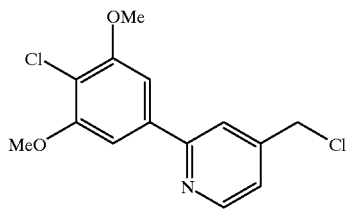

2-(4-Chloro-3,5-dimethoxyphenyl)-4-hydroxymethylpyridine (4.10 g) was treated in the same manner as described in Preparation Example 3 to give the title compound.

Yield: 4.20 g (96%). $^1$H-NMR (400 MHz, CDCl$_3$): 4.02 (s, 6H), 4.63 (s, 2H), 7.26 (s, 2H), 7.29 (d, 1H, J=4.9 Hz), 7.72 (s, 1H), 8.69 (d, 1H, J=4.9 Hz).

PREPARATION EXAMPLE 34

Synthesis of 1-[[2-(4-chloro-3,5-dimethoxyphenyl)pyridin-4-yl]methyl]piperidine-4-carboxamide:

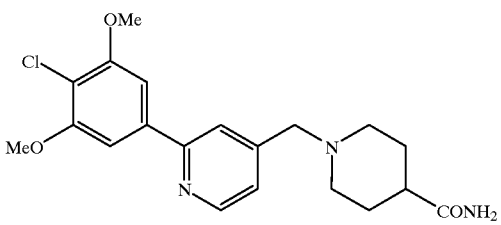

Piperidine-4-carboxamide (301 mg) and 2-(4-chloro-3,5-dimethoxyphenyl)pyridine (600 mg) were coupled in the same manner as described in Example 2 to give the title compound.

Yield: 743 mg (95%). $^1$H-NMR (400 MHz, CDCl$_3$): 1.75–1.90 (m, 4H), 2.07–2.25 (m, 3H), 2.94 (d, 2H, J=11.6 Hz), 3.57 (s, 2H), 4.02(s, 6H), 7.24–7.31 (m, 3H), 7.67 (s, 1H), 8.61 (d, 1H, J=5.1 Hz).

PREPARATION EXAMPLE 35

Synthesis of 1-[[2-(4-chloro-3,5-dimethoxyphenyl)pyridin-4-yl]methyl]-4-(ethoxycarbonylamino)piperidine:

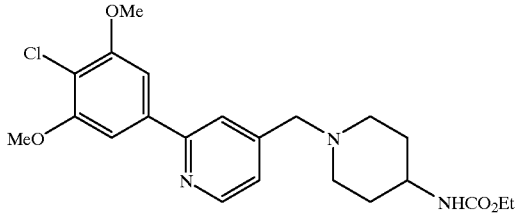

1-[[2-(4-chloro-3,5-dimethoxyphenyl)pyridin-4-yl] methyl]piperidine-4-carboxamide (743 mg) was treated in the same manner as described in Preparation Example 20 to give the title compound.

Yield: 887 mg (theoretical amount). $^1$H-NMR (400 MHz, CDCl$_3$): 1.24 (t, 3H, J=7.1 Hz), 1.43–1.59 (m, 2H), 1.96 (d, 2H, J=11.4 Hz), 2.19 (t, 2H, J=11.0 Hz), 2.82 (d, 2H, J=11.5 Hz), 3.56 (s, 2H), 4.02 (s, 6H), 4.10 (q, 2H, J=7.1 Hz), 7.26 (s, 2H), 7.66 (s, 1H), 7.71 (dd, 1H, J=5.6 Hz, 1.0 Hz), 8.6 (dd, 1H, J=4.9 Hz, 0.5 Hz).

PREPARATION EXAMPLE 36

Synthesis of 1-[[2-(4-chloro-3,5-dimethoxyphenyl)pyridin-4-yl]methyl]-4-methylaminopiperidine:

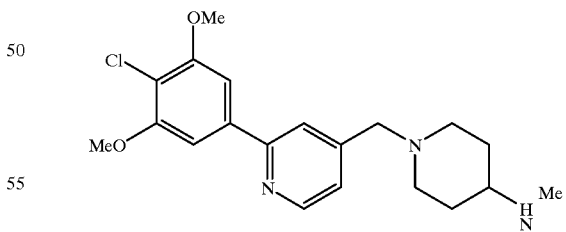

1-[[2-(4-chloro-3,5-diemthoxyphenyl)pyridin-4-yl] methyl]-4-(ethoxy-carbonylamino)piperidine (887 mg) was treated in the same manner as described in Preparation Example 21 to give the title compound.

Yield: 195 mg (27%). $^1$H-NMR (400 MHz, CDCl$_3$): 1.35–1.49 (m, 2H), 1.89 (d, 2H, J=12.3 Hz), 2.11 (t, 2H, J=9.4 Hz), 2.38–2.45 (m, 1H), 2.44 (s, 3H), 2.87 (d, 2H, J=10.7 Hz), 3.57 (s, 2H), 4.02 (s, 6H), 7.23–7.29 (m, 3H), 7.68 (s, 1H), 8.61 (d, 1H, J=4.9 Hz).

EXAMPLE 8

Synthesis of 1-[[2-(4-chloro-3,5-dimethoxyphenyl)pyridin-4-yl]methyl]-4-[N-[[2-(4-chloro-3,5-dimethoxyphenyl)pyridin-4-yl]methyl]-N-methylamino]piperidine tetrahydrochloride:

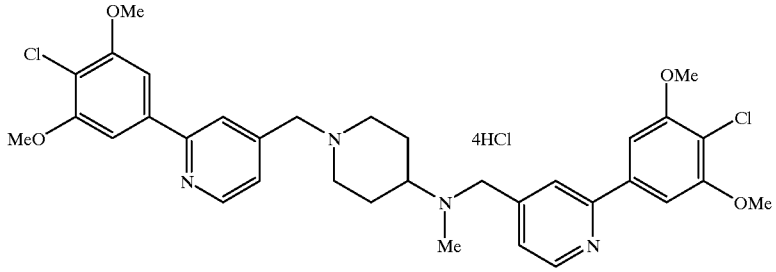

1-[[2-(4-chloro-3,5-dimethoxyphenyl)pyridin-4-yl]methyl]-4-methylamino-piperidine (195 mg) and 2-(4-chloro-3,5-dimethoxyphenyl)-4-chloromethylpyridine (152 mg) were condensed in the same manner as described in Example 2. A free base obtained was converted to a tetrahydrochloride giving yellow powder.

Yield: 300 mg (75%). $^1$H-NMR (400 MHz, CDCl$_3$): 1.60–1.90 (m, 4H), 2.06 (t, 2H, J=11.7 Hz), 2.26 (s, 3H), 2.45–2.55 (m, 1H), 2.97 (d, 2H, J=11.3 Hz), 3.57 (s, 2H), 3.67 (s, 2H), 4.01 (s, 6H), 4.02 (s, 6H), 7.24–7.28 (m, 6H), 7.65 (s, 1H), 7.67 (s, 1H), 8.61 (d, 1H, J=5.4 Hz), 8.62 (d, 1H, J=5.4 Hz).

PREPARATION EXAMPLE 37

Synthesis of 4-(p-anisidino)-1-[[2-(3,4,5-trimethoxyphenyl)pyridin-4-yl]methyl]-piperidine:

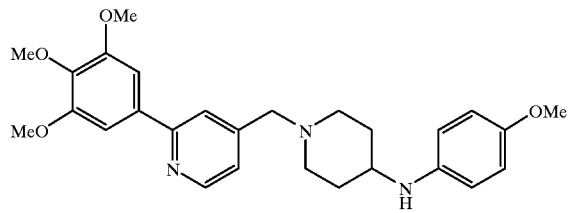

To a solution of 1-[[2-(3,4,5-trimethoxyphenyl)pyridin-4-yl]methyl]-4-piperidone (2.17 g) in toluene (40 mL) was added p-anisidine (900 mg) and molecular sieves 4A (6.0 g). The mixture was refluxed overnight, then filtered and the filtrate was evaporated. The residual oil was dissolved in ethanol (40 mL) and sodium borohydride (276 mg) was added. The mixture was stirred at room temperature for 2 hours before concentration in vacuo. The residue was dissolved in ethyl acetate, washed with brine, dried over anhydrous sodium sulfate and evaporated. The residual oil was subjected to silica gel column chromatography using chloroform-methanol (50:1) to give the title compound as yellow amorphous.

Yield: 1.56 g (55%). $^1$H-NMR (400 MHz, CDCl$_3$): 1.48 (br, 2H), 2.05 (br, 2H), 2.20 (br, 2H), 2.86 (br, 2H), 3.23 (s, 1H), 3.58 (s, 2H), 3.74 (s, 3H), 3.91 (s, 3H), 3.97 (s, 6H), 6.58 (d, 2H, J=8.8 Hz), 6.77 (d, 2H, J=9.0 Hz), 7.22 (d, 1H, J=5.1 Hz), 7.26 (s, 2H), 7.64 (s, 1H), 8.59 (d, 1H, J=4.9 Hz).

PREPARATION EXAMPLE 38

Synthesis of ethyl 2-(3,4,5-trimethoxyphenyl)nicotinate:

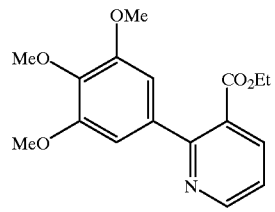

3,4,5-Trimethoxyphenylboronic acid (694 mg) and ethyl 2-chloronicotinate (608 mg) were reacted in the same manner as described in Preparation Example 1 to give the title compound.

Yield: 799 mg (77%). $^1$H-NMR (400 MHz, CDCl$_3$): 1.10 (t, 3H, J=7.2 Hz), 3.89 (s, 9H), 4.19 (q, 2H, J=7.2 Hz), 6.79 (s, 2H), 7.34 (dd, 1H, J=7.8 Hz, 4.8 Hz), 8.06 (dd, 1H, J=7.8 Hz, 1.7 Hz), 8.75 (dd, 1H, J=4.8 Hz, 1.7 Hz).

PREPARATION EXAMPLE 39

Synthesis of 3-hydroxymethyl-2-(3,4,5-trimethoxyphenyl)pyridine:

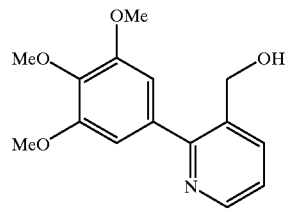

Ethyl 2-(3,4,5-trimethoxyphenyl)nicotinate (468 mg) was treated in the same manner as described in Preparation Example 2 to give the title compound.

Yield: 293 mg (72%). $^1$H-NMR (400 MHz, CDCl$_3$): 3.90 (s, 9H), 4.72 (s, 2H), 6.83 (s, 2H), 7.32 (dd, 1H, J=7.9 Hz, 4.8 Hz), 7.92 (dd, 1H, J=7.9 Hz, 1.7 Hz), 8.62 (dd, 1H, J=4.8 Hz, 1.7 Hz),

PREPARATION EXAMPLE 40

Synthesis of 3-chloromethyl-2-(3,4,5-trimethoxyphenyl)pyridine:

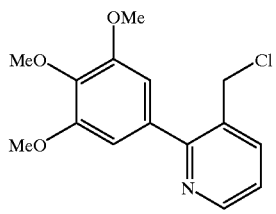

3-Hydroxymethyl-2-(3,4,5-trimethoxyphenyl)pyridine (293 mg) was treated in the same manner as described in the Preparation Example 3 to give the title compound.
Yield: 311 mg (theoretical amount).

EXAMPLE 9

Synthesis of 4-[N-(4-methoxyphenyl)-N-[[2-(3,4,5-trimethoxyphenyl)pyridin-3-yl]methyl]amino]-1-[[2-(3,4,5-trimethoxyphenyl)pyridin-4-yl]methyl]piperidine trihydrochloride:

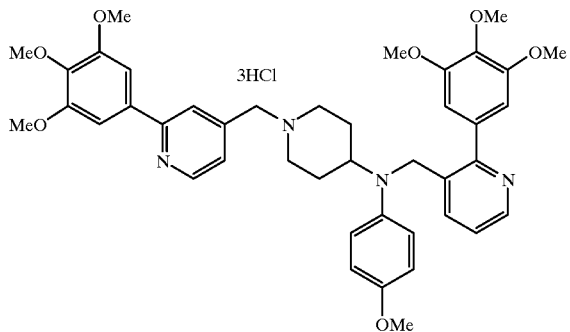

To a solution of 4-(p-anisidino)-1-[[2-(3,4,5-trimethoxyphenyl)pyridin-4-yl]methyl]piperidine (139 mg) and 3-chloromethyl-2-(3,4,5-trimethoxyphenyl)pyridine (114 mg) in acetonitrile (5 ml) was added potassium carbonate (83 mg) and potassium iodide (63 mg). The mixture was stirred at 70° C. overnight and evaporated. The residue was dissolved in chloroform, washed with water and brine, dried over anhydrous magnesium sulfate and evaporated. The residual oil was applied to a column of silica gel using diethylether-metanol (20:1) as an eluent. A free base obtained was converted to a trihydrochloride to give the title compound as yellow powder.
Yield: 16 mg, (8%). $^1$H-NMR (400 MHz, measured as a free base, CDCl$_3$): 1.60 (br, 2H), 1.77 (br, 2H), 2.09 (br, 2H), 2.93 (br, 2H), 3.45 (br, 1H), 3.54 (s, 2H), 3.73 (s, 3H), 3.90 (s, 6H), 3.91 (s, 6H), 3.96 (s, 6H), 4.34 (s, 2H), 6.65 (d, 2H, J=9.0 Hz), 6.71 (s, 2H), 6.74 (d, 2H), J=9.0 Hz), 7.16–7.19 (m, 2H), 7.22 (s, 2H), 7.55 (s, 1H), 7.79 (d, 1H, J=7.0 Hz), 8.50 (br, 1H), 8.58 (d, 1H, J=4.9 Hz).

EXAMPLE 10

Synthesis of 4-[N-(4-methoxyphenyl)-N-[[2-(3,4,5-trimethoxyphenyl)pyridin-4-yl]methyl]amino]-1-[[2-(3,4,5-trimethoxyphenyl)pyridin-4-yl]methyl]piperidine trihydrochloride:

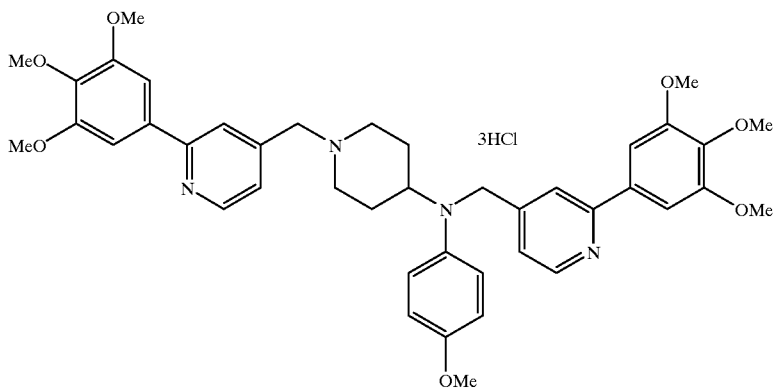

4-(p-Anisidino)-1-[[2-(3,4,5-trimethoxyphenyl)pyridin-4-yl]methyl]piperidine (1.56 g) and 4-chloromethyl-2-(3,4,5-trimethoxyphenyl)pyridine (1.08 g) were condensed by the same manner as described in Example 9. Yellow oil of a free base was converted to a trihydrochloride which gave the title compound as yellow powder.
Yield: 1.17 g (40%). $^1$H-NMR (400 MHz, measured as a free base, CDCl$_3$): 1.68–1.97 (m, 4H), 2.09–2.23 (m, 2H), 2.98 (br, 2H), 3.54–3.66 (m, 3H), 3.73 (s, 3H), 3.89 (s, 3H), 3.90 (s, 3H), 3.93 (s, 6H), 3.96 (s, 6H), 4.45 (s, 2H), 6.74 (d, 2H, J=9.2 Hz), 6.79 (d, 2H, J=9.2 H), 7.15 (s, 2H), 7.16–7.21 (m, 2H), 7.23 (s, 2H), 7.57 (s, 1H), 7.60 (s, 1H), 8.54 (d, 1H, J=5.1 Hz), 8.59 (d, 1H, J=4.9 Hz).

PREPARATION EXAMPLE 41

Synthesis of 3-(3,4,5-trimethoxyphenyl)benzyl alcohol:

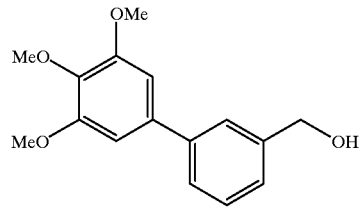

Ethyl 3-(3,4,5-trimethoxyphenyl)benzoate (5.09 g) was treated in the same manner as described in Preparation Example 2 to give the title compound.
Yield: 4.25 g (97%). $^1$H-NMR (400 MHz, CDCl$_3$): 1.87 (t, 1H, J=6.0 Hz), 3.89 (s, 3H), 3.92 (s, 6H), 4.76 (d, 1H, J=5.6 Hz), 6.77 (s, 2H), 7.34 (d, 1H, J=7.4 Hz), 7.42 (t, 1H, J=7.5 Hz), 7.48 (d, 1H, J=7.6 Hz), 7.55 (s, 1H).

PREPARATION EXAMPLE 42
Synthesis of 3-(3,4,5-trimethoxyphenyl)benzyl chloride:

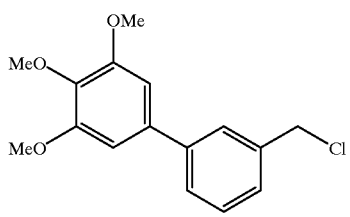

3-(3,4,5-Trimethoxyphenyl)benzyl alcohol (1.21 g) was treated in the same manner as described in Preparation Example 3 to give the title compound.

Yield: 893 mg (69%). $^1$H-NMR (400 MHz, CDCl$_3$): 3.87 (s, 3H), 3.90 (s, 6H), 4.62 (s, 2H), 6.75 (s, 2H), 7.33 (d, 1H, J=7.6 Hz), 7.39 (t, 1H, J=7.7 Hz), 7.48 (d, 1H, J=7.6 Hz), 7.54 (s, 1H).

EXAMPLE 11
Synthesis of 4-[N-(4-methoxyphenyl)-N-[3-(3,4,5-trimethoxyphenyl)benzyl]-amino]-1-[[2-(3,4,5-trimethoxyphenyl)pyridin-4-yl]methyl]piperidine dihydrochloride:

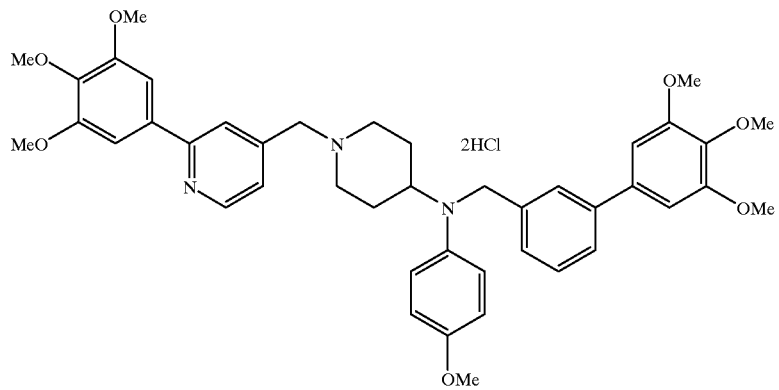

4-(p-Anisidino)-1-[[2-(3,4,5-trimethoxyphenyl)pyridin-4-yl]methyl]piperidine (139 mg) and 3-(3,4,5-trimethoxyphenyl)benzyl chloride (114 mg) were condensed by the same manner as described in Example 9. Yellow oil of a free base was converted to a dihydrochloride which gave the title compound as yellow powder.

Yield: 52 mg (22%). $^1$H-NMR (400 MHz, measured as a free base, CDCl$_3$): 1.77–1.92 (m, 5H), 2.14–2.20 (m, 2H), 2.95–3.00 (m, 5H), 2.14–2.20 (m, 2H), 2.95–3.00 (m, 2H), 3.58 (s, 2H), 3.72 (s, 3H), 3.88 (s, 3H), 3.89 (s, 6H), 3.90 (s, 3H), 3.96 (s, 6H), 4.47 (s, 2H), 6.70 (s, 2H), 6.74–6.83 (m, 4H), 7.20 (d, 1H, J=7.4 Hz), 7.23 (s, 2H), 7.25–7.27 (m, 1H), 7.33 (t, 1H, J=7.4 Hz), 7.38 (d, 1H, J=8.7 Hz), 7.43 (s, 1H), 7.62 (s, 1H), 8.59 (d, 1H, J=5.1 Hz).

PREPARATION EXAMPLE 43
Synthesis of ethyl 6-(3,4,5-trimethoxyphenyl)nicotinate:

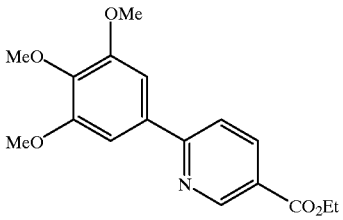

3,4,5-Trimethoxyphenylboronic acid (1.16 g) and ethyl 6-chloronitotinate (1.02 g) were coupled in the same manner as described in the Preparation Example 1 to give the title compound.

Yield: 1.42 g (82%) $^1$H-NMR (400 MHz, CDCl$_3$): 1.43 (t, 3H, J=7.2 Hz), 3.92 (s, 3H), 3.98 (s, 6H), 4.44 (q, 2H, J=7.2 Hz), 7.32 (s, 2H), 7.76 (d, 1H, J=8.3 Hz), 8.33 (dd, 1H, J=8.2 Hz, 2.2 Hz), 9.26 (d, 1H, J=2.2 Hz).

PREPARATION EXAMPLE 44

Synthesis of 5-hydroxymethyl-2-(3,4,5-trimethoxyphenyl)pyridine:

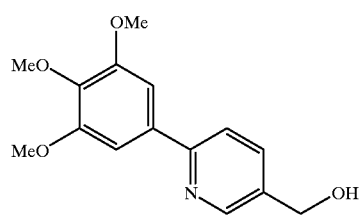

Ethyl 6-(3,4,5-trimethoxyphenyl)nicotinate (658 mg) was treated in the same manner as described in Preparation Example 2 to give the title compound.

Yield; 482 mg (85%). $^1$H-NMR (400 MHz, CDCl$_3$): 3.91 (s, 3H), 3.97 (s, 6H), 4.76 (s, 2H), 7.23 (s, 2H), 7.68 (d, 1H, J=7.4 Hz), 7.78 (dd, 1H, J=7.4 Hz, 2.3 Hz), 8.63 (d, 1H, J=2.3 Hz).

PREPARATION EXAMPLE 45
Synthesis of 5-chloromethyl-2-(3,4,5-trimethoxyphenyl)pyridine:

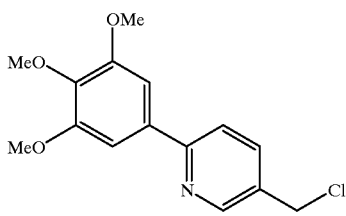

5-Hydroxymethyl-2-(3,4,5-trimethoxyphenyl)pyridine (685 mg) was treated in the same manner as described in Preparation Example 3 to give the title compound.

Yield: 717 mg (theoretical amount).

EXAMPLE 12

Synthesis of 4-[N-(4-methoxyphenyl)-N-[[2-(3,4,5-trimethoxyphenyl)pyridin-5-yl]methyl]amino]-1-[[2-(3,4,5-trimethoxyphenyl)pyridin-4-yl]methyl]piperidine trihydrochloride:

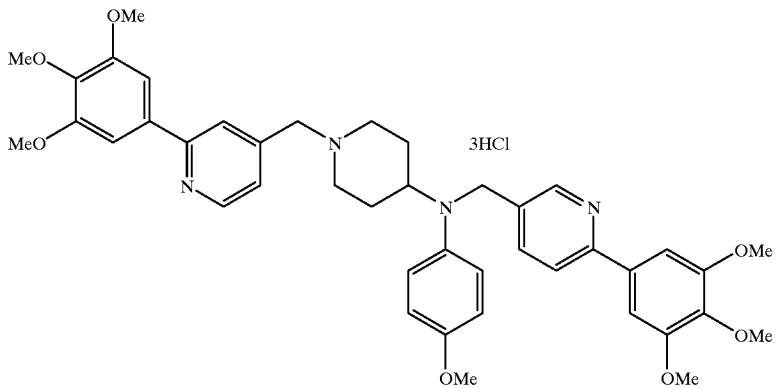

4-(p-Anisidino)-1-[[2-(3,4,5-trimethoxyphenyl)pyridin-4-yl]methyl]piperidine (139 mg) and 5-chloromethyl-2-(3,4,5-trimethoxyphenyl)pyridine (114 mg) were condensed by the same manner as described in Example 9. Yellow oil of a free base was converted to a trihydrochloride which gave the title compound as yellow powder.

Yield: 13 mg (5%). $^1$H-NMR (400 MHz, measured as a free base, CDCl$_3$): 1.76 (br, 2H), 1.88 (br, 2H), 2.14 (br, 2H), 2.97 (br, 2H), 3.51 (br, 1H), 3.57 (s, 2H), 3.73 (s, 3H), 3.89 (s, 3H), 3.90 (s, 3H), 3.94 (s, 6H), 3.96 (s, 6H), 4.42 (s, 2H), 6.78 (br, 4H), 7.20 (br, 3H), 7.23 (s, 2H), 7.57–7.70 (m, 3H), 8.58–8.60 (m, 2H).

PREPARATION EXAMPLE 46

Synthesis of ethyl 5-(3,4,5-trimethoxyphenyl)nicotinate:

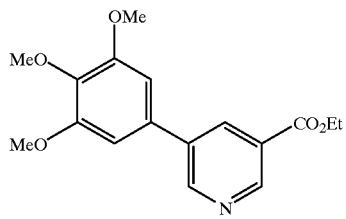

3,4,5-Trimethoxyphenylboronic acid (6.36 g) and ethyl 5-bromonicotinate (6.90 g) were reacted in the same manner as described in Preparation Example 1 to give the title compound.

Yield: 7.19 g (76%). $^1$H-NMR (400 MHz, CDCl$_3$): 1.44 (t, 3H, J=7.1 Hz), 3.91 (s, 3H), 3.95 (s, 6H), 4.46 (q, 2H, J=7.1 Hz), 6.79 (s, 2H), 8.44 (t, 1H, J=2.1 Hz), 8.96 (d, 1H, J=2.1 Hz), 9.18 (d, 1H, J=1.8 Hz).

PREPARATION EXAMPLE 47

Synthesis of 3-hydroxymethyl-5-(3,4,5-trimethoxyphenyl)pyridine:

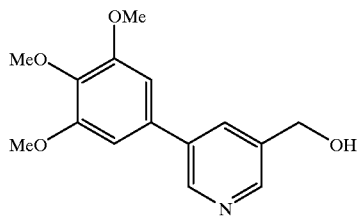

Ethyl 5-(3,4,5-trimethoxyphenyl)nicotinate (7.19 g) was treated in the same manner as described in the Preparation Example 2 to give the title compound.

Yield; 3.83 g (61%). $^1$H-NMR (400 MHz, CDCl$_3$): 3.88 (s, 3H), 3.89 (s, 6H), 4.39 (br, 1H), 4.80 (s, 2H), 6.72 (s, 2H), 7.89 (t, 1H, J=1.2 Hz), 8.47 (d, 1H, J=2.1 Hz), 8.63 (d, 1H, J=2.2 Hz).

PREPARATION EXAMPLE 48

Synthesis of 3-chloromethyl-5-(3,4,5-trimethoxyphenyl)pyridine:

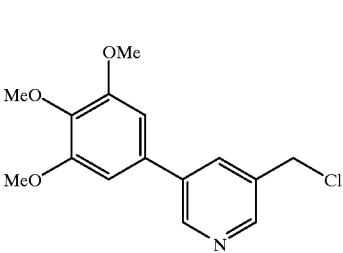

3-Hydroxymethyl-5-(3,4,5-trimethoxyphenyl)pyridine (2.85 g) was treated in the same manner as described in Preparation Example 3 to give the title compound.

Yield: 1.97 g (65%). $^1$H-NMR (400 MHz, CDCl$_3$): 3.90 (s, 3H), 3.94 (s, 6H), 4.67 (s, 2H), 6.75 (s, 2H), 7.87 (t, 1H, J=2.1 Hz), 8.59 (d, 1H, J=2.0 Hz), 8.76 (d, 1H, J=2.1 Hz).

EXAMPLE 13

Synthesis of 4-[N-(4-methoxyphenyl)-N-[[5-(3,4,5-trimethoxyphenyl)pyridin-3-yl]methyl]amino]-1-[[2-(3,4,5-trimethoxyphenyl)pyridin-4-yl]methyl]piperidine trihydrochloride:

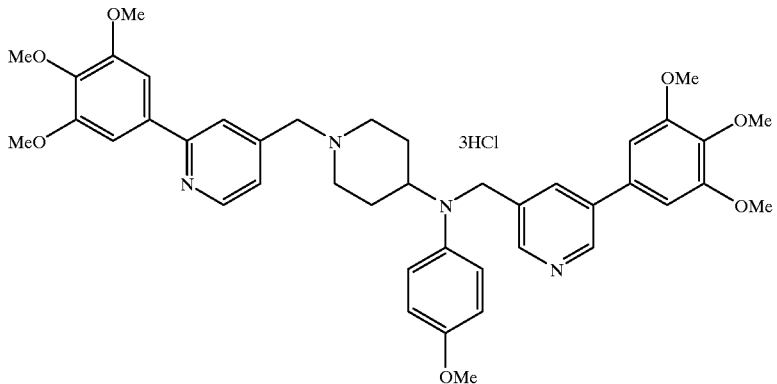

4-(p-Anisidino)-1-[[2-(3,4,5-trimethoxyphenyl)pyridin-4-yl]methyl]piperidine (139 mg) and 3-chloromethyl-5-(3,4,5-trimethoxyphenyl)pyridine (114 mg) were condensed by the same manner as described in Example 9. Yellow oil of a free base was converted to a trihydrochloride which gave the title compound as yellow powder.

Yield: 14 mg (5%). $^1$H-NMR (400 MHz, measured as a free base, CDCl$_3$); 1.73–1.75 (m, 2H), 1.88 (d, 2H, J=11.3 Hz), 2.13 (t, 2H, J=11.3 Hz), 2.96 (d, 2H, J=11.5 Hz), 3.50 (br, 1H), 3.55 (s, 2H), 3.72 (s, 3H), 3.88 (s, 3H), 3.89 (s, 9H), 3.96 (s, 6H), 4.45 (s, 2H), 6.65 (s, 2H), 6.76 (d, 2H, J=9.6 Hz), 6.80 (d, 2H, J=9.4 Hz), 7.20 (d, 1H, J=5.3 Hz), 7.22 (s, 2H), 7.59 (s, 1H), 7.67 (s, 1H), 8.50 (s, 1H), 8.59 (d, 1H, J=4.7 Hz), 8.62 (s, 1H).

PREPARATION EXAMPLE 49

Synthesis of 2,6-dimethoxy-4-iodophenol:

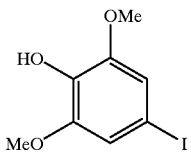

To a solution of 5-iodo-1,2,3-trimethoxybenzene (3.2 g) in 1,2-dichloroethane (40 mL) was added aluminum chloride (1.6 g). The mixture was stirred at 60° C. for 4 hours and evaporated. The residue was dissolved in 1 M aqueous sodium hydroxide solution and washed with ether. The aqueous layer was then acidified and extracted with chloroform. The organic layer was washed with brine, dried over anhydrous magnesium sulfate and evaporated to give the title compound as white crystalline powder.

Yield: 1.0 g (31%)

PREPARATION EXAMPLE 50

Synthesis of 1,3-dimethoxy-5-iodo-2-isopropoxybenzene:

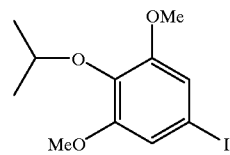

To a suspension of 2,6-dimethoxy-4-iodophenol (1.0 g) and potassium carbonate (938 mg) in DMF (10 mL) was added isopropyl iodide (507. L). The mixture was stirred at 60° C. for 3 hours and evaporated. Ethyl acetate and water were added to the residue, the organic layer was separated, washed with brine, dried over anhydrous sodium sulfate and evaporated. The residue was applied to a column of silica gel using hexane-ethyl acetate (5:1) as an eluent to give the title compound.

Yield: 788 mg (72%).

PREPARATION EXAMPLE 51

Synthesis of 3,5-dimethoxy-4-isopropoxyphenylboronic acid:

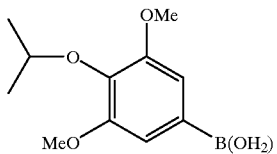

1,3-Dimethoxy-5-iodo-2-isopropoxybenzene (2.25 g) was treated in the same manner as described in Preparation Example 27 to give the title compound.

Yield: 1.23 g (74%).

PREPARATION EXAMPLE 52

Synthesis of ethyl 2-(3,5-dimethoxy-4-isopropoxyphenyl)isonicotinate:

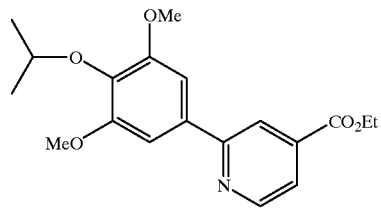

To a solution of 3,5-dimethoxy-4-isopropoxyphenylboronic acid (1.23 g) and ethyl 2-chloroisonicotinate (0.95 g) were condensed in the same manner as described in Preparation Example 1 to give the title compound.

Yield: 1.57 g(89%). $^1$H-NMR (400 MHz, CDCl$_3$): 1.33 (d, 6H, J=4.9 Hz), 1.44 (t, 3H, J=7.1 Hz), 3.95 (s, 6H), 4.42–4.49 (m, 3H), 7.29 (s, 2H), 7.75 (dd, 1H, J=4.9 Hz, 1.4 Hz), 8.24 (s, 1H), 8.80 (d, 1H, J=4.9 Hz).

PREPARATION EXAMPLE 53

Synthesis of 2-(3,5-dimethoxy-4-isopropoxyphenyl)-4-hydroxymethylpyridine:

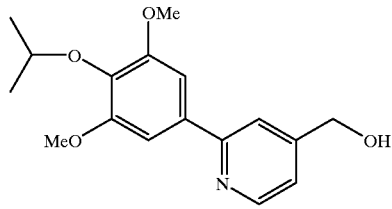

Ethyl 2-(3,5-dimethoxy-4-isopropoxyphenyl) isonicotinate (157 g) was treated in the same manner as described in the Preparation Example 2 to give the title compound.

Yield: 1.27 g (92%). $^1$H-NMR (400 MHz, CDCl$_3$): 1.32 (d, 6H, J=6.1 Hz), 3.93 (s, 6H), 4.45 (quint, 1H, J=6.1 Hz), 4.81 (s, 2H), 7.20 (d, 1H, J=5.1 Hz), 7.23 (s, 2H), 7.68 (s, 1H), 8.62 (d, 1H, J=5.1 Hz).

PREPARATION EXAMPLE 54

Synthesis of 4-chloromethyl-2-(3,5-dimethoxy-4-isopropoxyphenyl)pyridine:

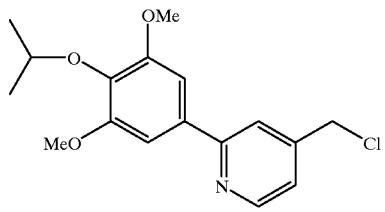

2-(3,5-Dimethoxy-4-isopropoxyphenyl)-4-hydroxymethylpyridine (1.49 g) was treated in the same manner as described in Preparation Example 3 to give the title compound.

Yield: 1.33 g (84%). $^1$H-NMR (400 MHz, CDCl$_3$): 1.32 (d, 6H, J=6.2 Hz), 3.94 (s, 6H), 4.45 (quint, 1H, J=6.1 Hz), 4.61 (s, 2H), 7.23–7.26 (m, 3H), 7.69 (s, 1H), 8.66 (d, 1H, J=5.1 Hz).

PREPARATION EXAMPLE 55

Synthesis of 1-[[2-(3,5-dimethoxy-4-isopropoxyphenyl) pyridin-4-yl]methyl]-4-piperidone ethylene ketal:

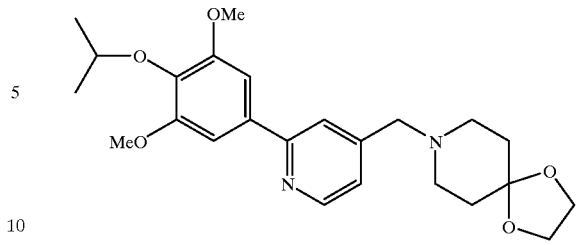

4-Chloromethyl-2-(3,5-dimethoxy-4-isopropoxyphenyl) pyridine (643 mg) and 4-piperidone ethylene ketal (287 mg) were coupled in the same manner as described in Example 2 to give the title compound.

Yield: 818 mg (95%). $^1$H-NMR (400 MHz, CDCl$_3$): 1.32 (d, 6H, J=6.1 Hz), 1.78 (t, 4H, J=5.7 Hz), 2.57 (br, 4H), 3.49 (s, 4H), 3.59 (s, 2H), 3.94 (s, 6H), 4.44 (quint, 1H, J=6.1 Hz), 7.21 (d, 1H, J=5.1 Hz), 7.23 (s, 2H), 7.65 (s, 1H), 8.59 (d, 1H, J=5.1 Hz).

PREPARATION EXAMPLE 56

Synthesis of 1-[[2-(3,5-dimethoxy-4-isopropoxyphenyl) pyridin-4-yl]methyl]-4-piperidone:

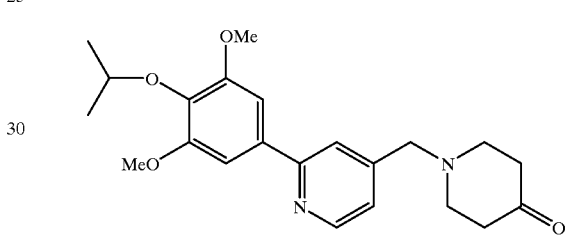

1-[[2-(3,5-Dimethoxy-4-isopropoxyphenyl)pyridin-4-yl] methyl]-4-piperidone ethylene ketal (818 mg) was treated in the same manner as described in Preparation Example 23 to give the title compound.

Yield: 717 mg (98%). $^1$H-NMR (400 MHz, CDCl$_3$): 1.32 (d, 6H, J=6.2 Hz), 2.50 (t, 4H, J=6.1 Hz), 2.81 (t, 4H, J=6.1 Hz), 3.69 (s, 2H), 3.95 (s, 6H), 4.45 (quint, 1H, J=6.2 Hz), 7.24 (s, 2H), 7.25–7.27 (m, 1H), 7.68 (s, 1H), 8.63 (d, 1H, J=5.1 Hz).

PREPARATION EXAMPLE 57

Synthesis of 4-(p-anisidino)-1-[[2-(3,5-dimethoxy-4-isopropoxyphenyl)pyridin-4-yl]methyl]piperidine:

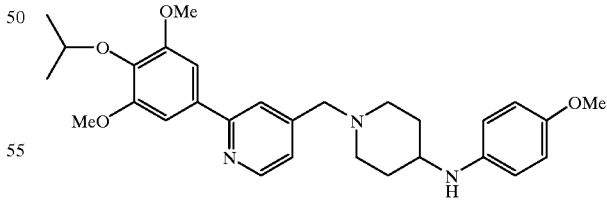

1-[[2-(3,5-dimethoxy-4-isopropoxyphenyl)pyridin-4-yl] methyl]-4-piperidone (350 mg) and p-anisidine (123 mg) were condensed in the same manner as described in Preparation Example 37 to give the title compound.

Yield: 307 mg (69%). $^1$H-NMR (400 MHz, CDCl$_3$): 1.32 (d, 6H, J=6.3 Hz), 1.46–1.52 (m, 2H), 2.00–2.24 (m, 2H), 2.22 (t, 2H, J=11.1 Hz), 2.86 (d, 2H, J=12.1 Hz), 3.18–3.28 (m, 1H), 3.58 (s, 2H), 3.74 (s, 3H), 3.94 (s, 6H), 4.40 (quint, 1H, J=6.3 Hz), 6.58 (d, 2H, J=6.6 Hz), 6.78 (d, 2H, J=6.6

Hz), 7.20 (d, 1H, J=5.1 Hz), 7.24 (s, 2H), 7.64 (s, 1H), 8.59 (d, 1H, J=5.1 Hz).

EXAMPLE 14

Synthesis of 1-[[2-(3,5-dimethoxy-4-isopropoxyphenyl) pyridin-4-yl]methyl]-4-[N-[[2-(3,5-dimethoxy-4-isopropoxyphenyl)pyridin-4-yl]methyl]-N-(4-methoxyphenyl)amino]piperidine trihydrochloride:

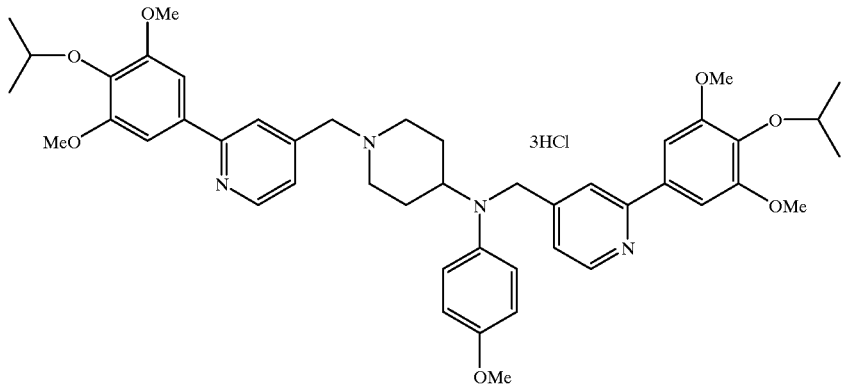

4-(p-anisidino)-1-[[2-(3,5-dimethoxy-4-isopropoxyphenyl)pyridin-4-yl]methyl]piperidine (307 mg) and 4-chloromethyl-2-(3,5-dimethoxy-4-isopropoxyphenyl) pyridine (201 mg) were condensed in the same manner as described in Example 9. A free base obtained was converted to a trihydrochloride giving the title compound as yellow powder.

Yield: 230 mg (46%). $^1$H-NMR (400 MHz, CDCl$_3$): 1.31 (d, 6H, J=3.3 Hz), 1.32 (d, 6H, J=6.8 Hz), 1.70–1.92 (m, 4H), 2.10–2.20 (m, 2H), 2.92–3.01 (m, 2H), 3.56 (s, 2H), 3.73 (s, 3H), 3.85–3.95 (m, 1H), 3.90 (s, 6H), 3.93 (s, 6H), 4.39–4.49 (m, 4H), 6.73 (d, 2H, J=4.8 Hz), 6.78 (d, 2H, J=4.8 Hz), 7.14 (s, 2H), 7.15–7.20 (m, 2H), 7.23 (s, 2H), 7.58 (s, 1H), 7.60 (s, 1H), 8.53 (d, 1H, J=5.1 Hz), 8.58 (d, 1H, J=5.1 Hz).

PREPARATION EXAMPLE 58

Synthesis of 4-benzylamino-1-[[2-(3,4,5-trimethoxyphenyl) pyridin-4-yl]-methyl]piperidine:

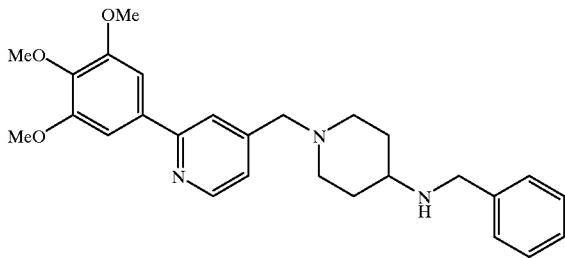

1-[[2-(3,4,5-Trimethoxyphenyl)pyridin-4-yl]methyl-4-piperidone (1.40 g) and benzylamine (0.51 g) was condensed in the same manner as described in Preparation Example 37 to give the title compound as yellow amorphous.

Yield: 1.20 g (68%). $^1$H-NMR (400 MHz, CDCl$_3$): 1.40–1.60 (m, 2H), 1.88–2.09 (m, 5H), 2.54 (br, 1H), 2.82–2.85 (m, 2H), 3.52 (s, 2H), 3.80 (s, 2H), 3.89 (s, 2H), 3.95 (s, 6H), 7.18–7.31 (m, 8H), 7.64 (s, 1H), 8.57 (d, 1H, J=5.1 Hz).

EXAMPLE 15

Synthesis of 4-[N-benzyl-N-[[2-(3,4,5-trimethoxyphenyl) pyridin-3-yl]-methyl]amino]-1-[[2-(3,4,5-trimethoxyphenyl)pyridin-4-yl]methyl]piperidine tetrahydrochloride:

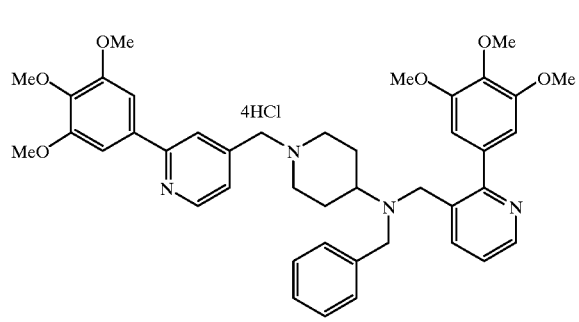

4-Benzylamino-1-[[2-(3,4,5-trimethoxyphenyl)pyridin-4-yl]methyl]piperidine (134 mg) and 3-chloromethyl-2-(3,4,5-trimethoxyphenyl)pyridine (114 mg) were condensed in the same manner as described in Example 9. A free base obtained was converted to a tetrahydrochloride to give the title compound as yellow powder.

Yield: 43 mg, (17%). $^1$H-NMR (400 MHz, measured as a free base, CDCl$_3$): 1.63 (br, 4H), 1.87 (br, 2H), 2.39 (br, 1H), 2.88 (br, 2H), 3.49 (s, 2H), 3.57 (s, 2H), 3.68 (s, 2H), 3.86 (s, 6H), 3.88 (s, 3H), 3.90 (s, 3H), 3.96 (s, 6H), 6.60 (s, 2H), 7.17 (d 1H, J=5.1 Hz), 7.22–7.29 (m, 8H), 7.56 (s, 1H), 8.02 (d, 1H, J=8.0 Hz), 8.50 (d, 1H, J=6.4 Hz), 8.58 (d, 1H, J=5.1 Hz).

EXAMPLE 16

Synthesis of 4-[N-benzyl-N-[[2-(3,4,5-trimethoxyphenyl) pyridin-4-yl]methyl]amino]-1-[[2-(3,4,5-trimethoxyphenyl) pyridin-4-yl]methyl]piperidine tetrahydrochloride:

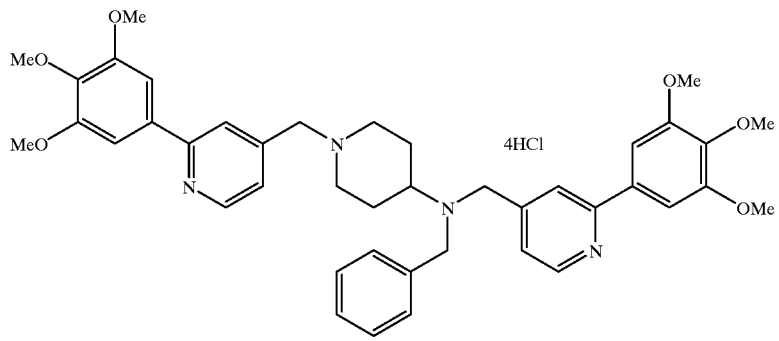

4-Benzylamino-1-[[2-(3,4,5-trimethoxyphenyl)pyridin-4-yl]methyl]piperidine (230 mg) and 4-chloromethyl-2-(3,4,5-trimethoxyphenyl)pyridine (158 mg) were condensed by the same manner as described in Example 9. Yellow oil of a free base was converted to a tetrahydrochloride which gave the title compound as yellow powder.

Yield: 172 mg (47%). $^1$H-NMR (400 MHz, measured as a free base, CDCl$_{3)}$: 1.69–1.85 (m, 4H), 1.93–1.99 (m, 2H), 2.56 (br, 1H), 2.93–3.00 (m, 2H), 3.51 (s, 2H), 3.71 (s, 2H), 3.74 (s, 2H), 3.90 (s, 6H), 3.96 (s, 6H), 3.96 (s, 6H), 7.18–7.32 (m, 9H), 7.38 (d, 2H, J=7.1 Hz), 7.59 (s, 1H), 7.68 (s, 1H), 8.56 (d, 1H, J=5.1 Hz), 8.60 (d, 1H, J=5.1 Hz).

EXAMPLE 17

Synthesis of 4-[N-benzyl-N-[3-(3,4,5-trimethoxyphenyl)benzyl]amino]-1-[[2-(3,4,5-trimethoxyphenyl)pyridin-4-yl]methyl]piperidine trihydrochloride:

trimethoxyphenyl)benzyl chloride (114 mg) were condensed by the same manner as described in Example 9. Yellow oil of a free base was converted to a trihydrochloride which gave the title compound as yellow powder.

Yield: 47 mg (18%). $^1$H-NMR (400 MHz, measured as a free base, CDCl$_3$): 1.70–1.86 (m, 4H), 1.96 (br, 2H), 2.59 (br, 1H), 2.94 (br, 2H), 3.51 (s, 2H), 3.70 (s, 2H), 3.74 (s, 2H), 3.89 (s, 3H), 3.90 (s, 3H), 3.92 (s, 6H), 3.96 (s, 6H), 6.75 (s, 2H), 7.18–7.30 (m, 6H), 7.35–7.40 (m, 5H), 7.56 (s, 1H), 7.60 (s, 1H), 8.58 (d, 1H, J=5.1 Hz).

EXAMPLE 18

Synthesis of 4-[N-benzyl-N-[[2-(3,4,5-trimethoxyphenyl)pyridin-5-yl]methyl]amino]-1-[[2-(3,4,5-trimethoxyphenyl)pyridin-4-yl]methyl]piperidine tetrahydrochloride:

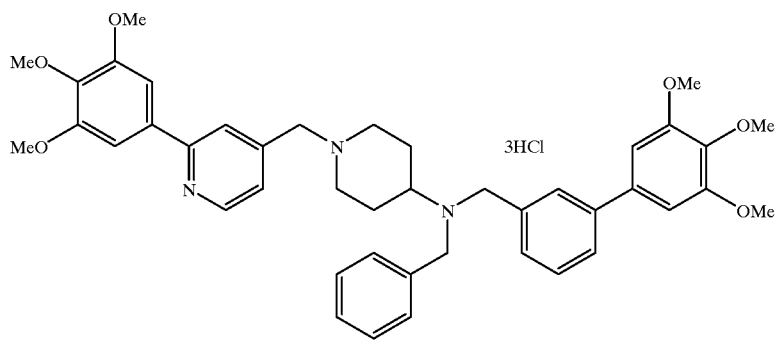

4-Benzylamino-1-[[2-(3,4,5-trimethoxyphenyl)pyridin-4-yl]methyl]piperidine (134 mg) and 3-(3,4,5-

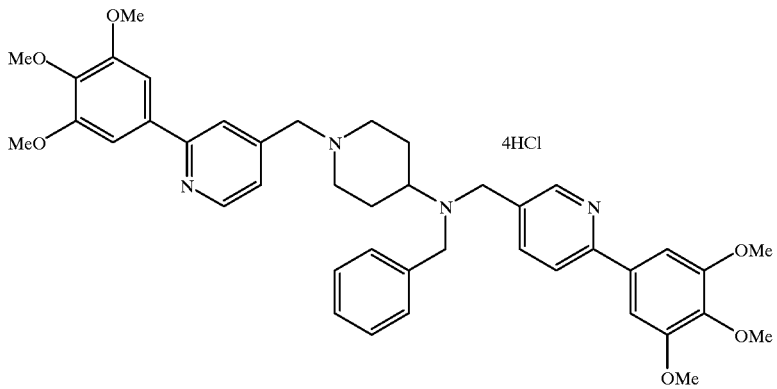

4-Benzylamino-1-[[2-(3,4,5-trimethoxyphenyl)pyridin-4-yl]methyl]piperidine (134 mg) and 5-chloromethyl-2-(3,4,5-trimethoxyphenyl)pyridine (114 mg) were condensed by the same manner as described in Example 9. Yellow oil of a free base was converted to a tetrahydrochloride which gave the title compound as yellow powder.

Yield: 44 mg (17%). ¹H-NMR (400 MHz, measured as a free base, CDCl₃): 1.81 (br, 4H), 1.96 (br, 2H), 2.55 (br, 1H), 2.96 (br, 2H), 3.52 (s, 2H), 3.69 (s, 4H), 3.89 (s, 6H), 3.95 (s, 6H), 3.96 (s, 6H), 7.19–7.32 (m, 8H), 7.36–7.38 (m, 2H), 7.61 (d, 2H, J=7.6 Hz), 7.69–7.73 (m, 1H), 8.59 (d, 1H, J=4.9 Hz), 8.63 (s, 1H).

EXAMPLE 19

Synthesis of 4-[N-benzyl-N-[[5-(3,4,5-trimethoxyphenyl)pyridin-3-yl]methyl]amino]-1-[[2-(3,4,5-trimethoxyphenyl)pyridin-4-yl]methyl]piperidine tetrahydrochloride:

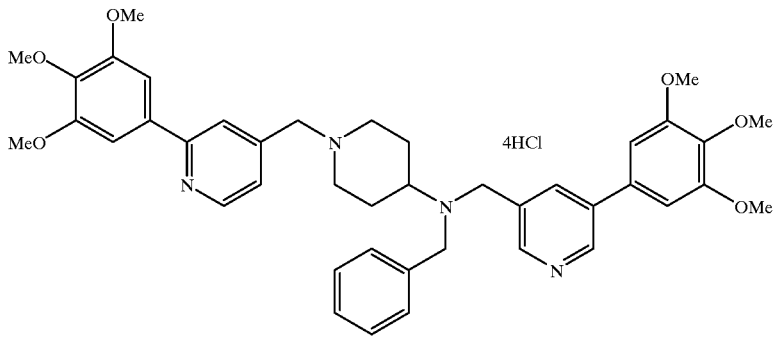

4-Benzylamino-1-[[2-(3,4,5-trimethoxyphenyl)pyridin-4-yl]methyl]piperidine (134 mg) and 3-chloromethyl-5-(3,4,5-trimethoxyphenyl)pyridine (114 mg) were condensed by the same manner as described in Example 9. Yellow oil of a free base was converted to a tetrahydrochloride which gave the title compound as yellow powder.

Yield: 26 mg (10%). ¹H-NMR (400 MHz, measured as a free base, CDCl₃): 1.83 (br, 4H), 1.97 (br, 2H), 2.58 (br, 1H), 2.95 (br, 2H), 3.53 (s, 2H), 3.71 (s, 2H), 3.75 (s, 2H), 3.90 (s, 6H), 3.93 (s, 6H), 3.96 (s, 6H), 6.74 (s, 2H), 7.19–7.30 (m, 6H), 7.36 (d, 2H, J=6.8 Hz), 7.60 (s, 1H), 7.79 (s, 1H), 8.54 (s, 1H), 8.59 (d, 1H, J=5.1 Hz), 8.64 (s, 1H).

PREPARATION EXAMPLE 59

Synthesis of 1-(tert-butoxycarbonyl)-4-[N-[[2-(3,4,5-trimethoxyphenyl)pyridin-4-yl]methyl]aminomethyl]piperidine:

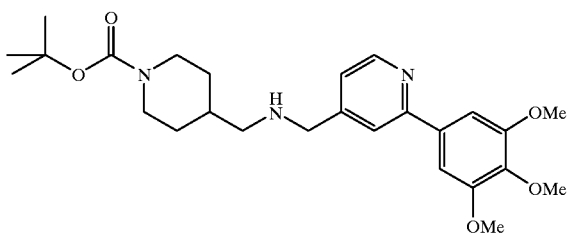

1-(tert-Butoxycarbonyl)-4-aminomethylpiperidine (200 mg) and 4-chloromethyl-2-(3,4,5-trimethoxyphenyl)pyridine (183 mg) were condensed in the same manner as described in Example 2 to give the title compound as yellow syrup.

Yield: 264 mg (90%). ¹H-NMR (400 MHz, CDCl₃): 1.12–1.27 (m, 3H), 1.45 (s, 9H), 1.60 (br, 1H), 1.74 (d, 2H, J=12.9 Hz), 2.54 (d, 2H, J=6.6 Hz), 2.69 (br, 2H), 3.87 (s, 2H), 3.90 (s, 3H), 3.97 (s, 6H), 4.03–4.14 (m, 2H), 7.20 (d, 1H, J=3.9 Hz), 7.24 (s, 2H), 7.65 (s, 1H), 8.60 (d, 1H, J=4.9 Hz).

PREPARATION EXAMPLE 60

Synthesis of 1-(tert-butoxycarbonyl)-4-[N-methyl-N-[[2-(3,4,5-trimethoxyphenyl)pyridin-4-yl]methyl]aminomethyl]piperidine:

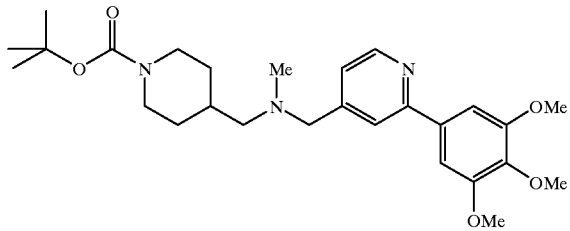

1-(tert-butoxycarbonyl)-4-[N-[[2-(3,4,5-trimethoxyphenyl)pyridin-4-yl]methyl]aminomethyl]piperidine (264 mg) was treated in the same manner as described in Preparation Example 11 to give the title compound as yellow syrup.

Yield: 157 mg (58%). $^1$H-NMR (400 MHz, CDCl$_3$): 1.00–1.09 (m, 2H), 1.43 (s, 9H), 1.65–1.70 (m, 1H), 1.79 (d, 2H, J=12.7 Hz), 2.21 (d, 2H, J=7.4 Hz), 2.23 (s, 3H), 2.69 (br, 2H), 3.52 (s, 2H), 3.89 (s, 3H), 3.96 (s, 6H), 4.07–4.13 (m, 2H), 7.20 (d, 1H, J=4.9 Hz), 7.24 (s, 2H), 7.64 (s, 1H), 8.58 (d, 1H, J=5.1 Hz).

PREPARATION EXAMPLE 61

Synthesis of 4-[N-methyl-N-[[2-(3,4,5-trimethoxyphenyl)pyridin-4-yl]methyl]aminomethyl]piperidine:

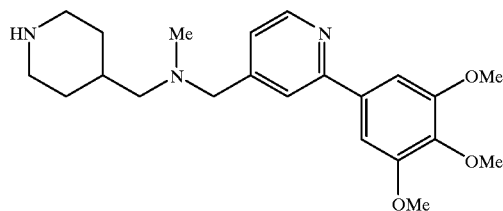

1-(tert-Butoxycarbonyl)-4-[N-methyl-N-[[2-(3,4,5-trimethoxyphenyl)pyridin-4-yl]methyl]aminomethyl]piperidine (152 mg) was treated in the same manner as described in Preparation Example 12 to give the title compound as yellow crystals.

Yield: 105 mg (88%). $^1$H-NMR (400 MHz, CDCl$_3$): 1.00–1.10 (m, 2H), 1.60–1.68 (m, 1H), 1.80 (d, 2H, J=12.5 Hz), 2.03 (br, 1H), 2.20 (d, 2H, J=8.4 Hz), 2.21 (s, 3H), 2.58 (dt, 2H, J=12.1 Hz, 2.1 Hz), 3.05 (d, 2H, J=12.1 Hz), 3.51 (s, 2H), 3.89 (s, 3H), 3.95 (s, 6H), 7.20 (d, 1H, J=5.1 Hz), 7.24 (s, 2H), 7.65 (s, 1H), 8.57 (d, 1H, J=5.9 Hz).

EXAMPLE 20

Synthesis of 4-[N-methyl-N-[[2-(3,4,5-trimethoxyphenyl)pyridin-4-yl]methyl]aminomethyl]-1-[[2-(3,4,5-trimethoxyphenyl)pyridin-4-yl]methyl]piperidine dioxalate:

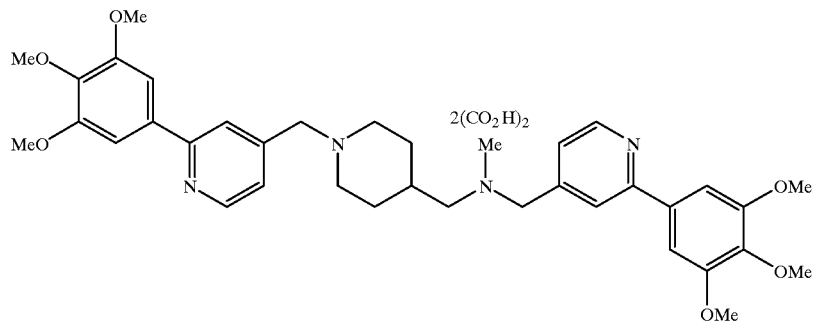

4-[N-methyl-N-[[2-(3,4,5-trimethoxyphenyl)pyridin-4-yl]methyl]aminomethyl]piperidine (96 mg) and 4-chloromethyl-2-(3,4,5-trimethoxyphenyl)pyridine (73 mg) were condensed in the same manner as described in Example 2. The title compound was obtained as white powder after converting a free base to a dioxalate.

Yield: 109 mg (40%). $^1$H-NMR (400 MHz, measured as a free base, CDCl$_3$): 1.19–1.27 (m, 2H), 1.56 (br, 1H), 1.81 (d, 2H, J=11.1 Hz), 1.99–2.04 (m, 2H), 2.23 (s, 5H), 2.88 (d, 2H, J=11.1 Hz), 3.53 (s, 4H), 3.89 (s, 3H), 3.90 (s, 3H), 3.94 (s, 6H), 3.96 (s, 6H), 7.20 (br, 2H), 7.23 (s, 4H), 7.61 (s, 1H), 7.64 (s, 1H), 8.58 (d, 2H, J=4.9 Hz).

PREPARATION EXAMPLE 62

Synthesis of 4-(3,5-dimethoxyphenylamino)-1-[[2-(3,4,5-trimethoxyphenyl)pyridin-4-yl]methyl]piperidine:

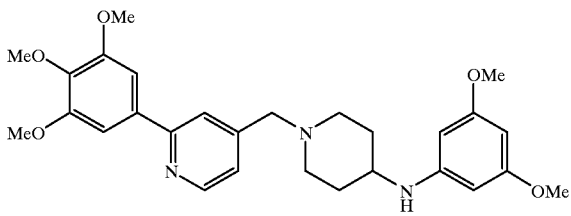

1-[[2-(3,4,5-Trimethoxyphenyl)pyridin-4-yl]methyl-4-piperidone (1.40 g) and 3,5-dimethoxyaniline (722 mg) were treated in the same manner as described in Preparation Example 37 to give the title compound.

Yield: 800 mg (41%). $^1$H-NMR (400 MHz, CDCl$_3$): 1.40–1.90 (m, 2H), 1.95–2.50 (m, 4H), 2.93 (br, 2H), 3.31 (br, 1H), 3.65 (br, 2H), 3.72 (s, 6H), 3.88 (s, 3H), 3.96 (s, 6H), 5.76 (s, 2H), 5.85 (s, 1H), 7.20–7.35 (m, 3H), 7.73 (br, 1H), 8.60 (d, 1H, J=4.9 Hz).

EXAMPLE 21

Synthesis of 4-[N-(3,5-dimethoxyphenyl)-N-[[2-(3,4,5-trimethoxyphenyl)pyridin-3-yl]methyl]amino]-1-[[2-(3,4,5-trimethoxyphenyl)pyridin-4-yl]methyl]piperidine trihydrochloride:

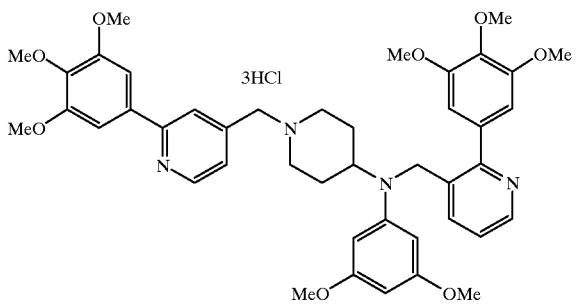

4-(3,5-Dimethoxyphenylamino)-1-[[2-(3,4,5-trimethoxyphenyl)pyridin-4-yl]methyl]piperidine (148 mg) and 3-chloromethyl-2-(3,4,5-trimethoxyphenyl)pyridine (114 mg) were condensed in the same manner as described in Example 9. Yellow syrup obtained was converted to a trihydrochloroide to give the title compound as yellow powder.

Yield: 29 mg, (11%). $^1$H-NMR (400 MHz, measured as a free base, CDCl$_3$): 1.60–1.63 (m, 2H), 1.79 (d, 2H, J=11.7 Hz), 2.13 (t, 2H, J=11.4 Hz), 2.94 (d, 2H, J=11.3 Hz), 3.54 (s, 2H), 3.71 (s, 6H), 3.78–3.84 (m, 1H), 3.90 (s, 3H), 3.91 (s, 6H), 3.92 (s, 3H), 3.96 (s, 6H), 4.41 (s, 2H), 5.84 (s, 2H), 6.72 (s, 2H), 7.09–7.24 (m, 5H), 7.53 (s, 1H), 7.71 (d, 1H, J=6.6 Hz), 8.51 (dd, 1H, J=4.7 Hz, 1.6 Hz), 8.59 (d, 1H, J=4.9 Hz).

PREPARATION EXAMPLE 63
Synthesis of ethyl 2-(3,4,5-trimethoxyphenyl)benzoate:

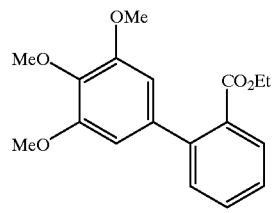

3,4,5-Trimethoxyphenylboronic acid (639 mg) and ethyl 2-bromobenzoate (479 mg) were condensed in the same manner as described in Preparation Example 1 to give the title compound.

Yield: 655 mg (69%). $^1$H-NMR (400 MHz, CDCl$_3$): 1.04 (t, 3H, J=7.2 Hz), 3.86 (s, 6H), 3.89 (s, 3H), 4.12 (q, 2H, J=7.2 Hz), 6.54 (s, 2H), 7.40–7.42 (m, 2H), 7.51 (t, 1H, J=7.8 Hz), 7.77 (d, 1H, J=6.8 Hz).

PREPARATION EXAMPLE 64
Synthesis of 2-(3,4,5-trimethoxyphenyl)benzyl alcohol:

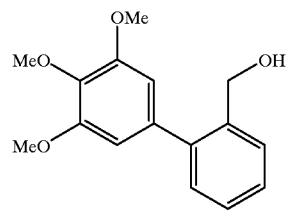

Ethyl 2-(3,4,5-trimethoxyphenyl)benzoate (655 mg) was treated in the same manner as described in Preparation Example 2 to give the title compound.

Yield: 630 mg (theoretical amount). $^1$H-NMR (400 MHz, CDCl$_3$): 3.85 (s, 6H), 3.90 (s, 3H), 4.61 (s, 2H), 6.61 (s, 2H), 7.26–7.39 (m, 3H), 7.53 (d, 1H, J=6.8 Hz).

PREPARATION EXAMPLE 65
Synthesis of 2-(3,4,5-trimethoxyphenyl)benzyl chloride:

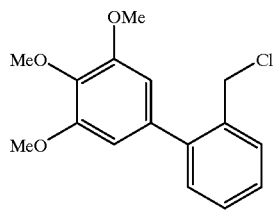

2-(3,4,5-Trimethoxyphenyl)benzyl alcohol (630 mg) was treated in the same manner as described in Preparation Example 3 to give the title compound.

Yield: 615 mg (theoretical amount). $^1$H-NMR (400 MHz, CDCl$_3$): 3.87 (s, 6H), 3.90 (s, 3H), 4.53 (s, 2H), 6.66 (s, 2H), 7.29–7.32 (m, 1H), 7.34–7.39 (m, 2H), 7.50–7.52 (m, 1H).

EXAMPLE 22
Synthesis of 4-[N-(3,5-dimethoxyphenyl)-N-[2-(3,4,5-trimethoxyphenyl)benzyl]amino]-1-[[2-(3,4,5-trimethoxyphenyl)pyridin-4-yl]methyl]piperidine dihydrochloride:

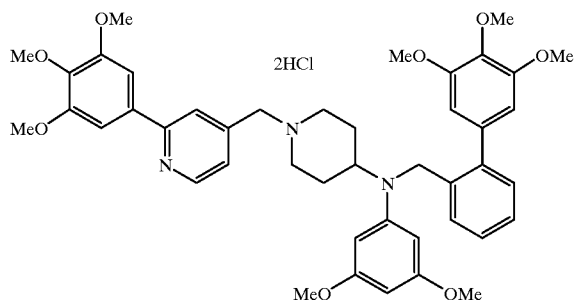

4-(3,5-Dimethoxyphenylamino)-1-[[2-(3,4,5-trimethoxyphenyl)pyridin-4-yl]methyl]piperidine (148 mg) and 2-(3,4,5-trimethoxyphenyl)benzyl chloride (114 mg) were condensed in the same manner as described in Example 9. A free base obtained was converted to a dihydrochloroide to give the title compound as yellow powder.

Yield: 20 mg, (8%). $^1$H-NMR (400 MHz, measured as a free base, CDCl$_{3)}$: 1.50–1.90 (m, 4H), 2.05–2.20 (m, 2H), 2.92 (br, 2H), 3.52 (br, 3H), 3.68 (s, 6H), 3.85 (s, 6H), 3.88 (s, 3H), 3.89 (s, 3H), 3.94 (s, 6H), 4.31 (s, 2H), 5.85 (br, 3H), 6.52 (s, 2H), 7.05–7.27 (m, 6H), 7.34 (s, 1H), 7.51 (s, 1H), 8.56 (s, 1H).

EXAMPLE 23

Synthesis of 4-[N-(3,5-dimethoxyphenyl)-N-[[2-(3,4,5-trimethoxyphenyl)pyridin-4-yl]methyl]amino]-1-[[2-(3,4,5-trimethoxyphenyl)pyridin-4-yl]methyl]piperidine trihydrochloride:

4-(3,5-Dimethoxyphenylamino)-1-[[2-(3,4,5-trimethoxyphenyl)pyridin-4-yl]methyl]piperidine (148 mg) and 4-chloromethyl-2-(3,4,5-trimethoxyphenyl)pyridine (114 mg) were condensed by the same manner as described in Example 9. Yellow oil of a free base was converted to a trihydrochloride which gave the title compound as yellow powder.

Yield: 40 mg (18%). $^1$H-NMR (400 MHz, measured as a free base, CDCl$_3$): 1.68–1.90 (m, 4H), 2.12–2.22 (m, 2H), 2.94–3.02 (m, 2H), 3.57 (s, 2H), 3.71 (s, 6H), 3.81–3.83 (m, 1H), 3.89 (s, 3H), 3.90 (s, 3H), 3.93 (s, 6H), 3.96 (s, 6H), 4.52 (s, 2H), 5.89–5.94 (m, 3H), 7.14 (d, 1H, J=5.3 Hz), 7.16 (s, 2H), 7.20 (d, 1H, J=3.7 Hz), 7.22 (s, 2H), 7.54–7.60 (m, 2H), 8.55 (d, 1H, J=5.1 Hz), 8.59 (d, 1H, J=5.1 Hz).

EXAMPLE 24

Synthesis of 4-[N-(3,5-dimethoxyphenyl)-N-[3-(3,4,5-trimethoxyphenyl)benzyl]amino]-1-[[2-(3,4,5-trimethoxyphenyl)pyridin-4-yl]methyl]piperidine dihydrochloride:

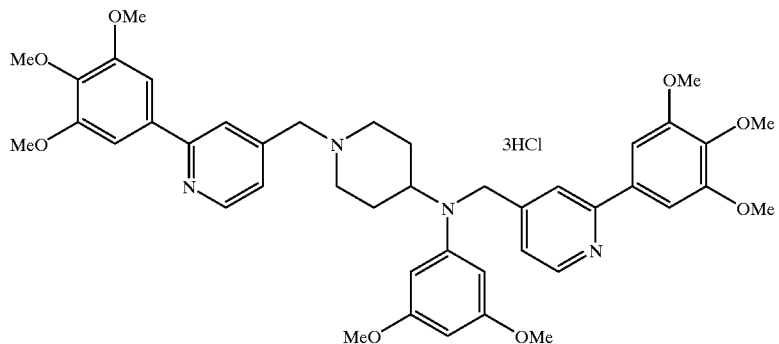

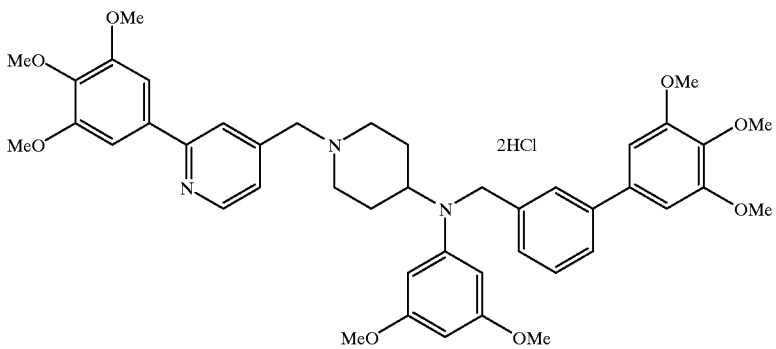

4-(3,5-Dimethoxyphenylamino)-1-[[2-(3,4,5-trimethoxyphenyl)pyridin-4-yl]methyl]piperidine (148 mg) and 3-(3,4,5-trimethoxyphenyl)benzyl chloride (114 mg) were condensed by the same manner as described in Example 9. Yellow oil of a free base was converted to a dihydrochloride which gave the title compound as yellow powder.

Yield: 41 mg (16%). $^1$H-NMR (400 MHz, measured as a free base, CDCl$_3$): 1.78–1.88 (m, 4H), 2.16 (t, 2H, J=10.7 Hz), 2.96 (d, 2H, J=11.3 Hz), 3.56 (s, 2H), 3.70 (s, 6H), 3.73–3.84 (m, 1H), 3.87 (s, 3H), 3.89 (s, 6H), 3.90 (s, 3H), 3.95 (s, 6H), 4.54 (s, 2H), 5.95 (s, 2H), 6.71 (s, 2H), 7.19–7.26 (m, 4H), 7.31–7.39 (m, 3H), 7.42 (s, 1H), 7.59 (s, 1H), 8.58 (d, 1H, J=4.9 Hz).

EXAMPLE 25

Synthesis of 4-[N-(3,5-dimethoxyphenyl)-N-[[2-(3,4,5-trimethoxyphenyl)pyridin-5-yl]methyl]amino]-1-[[2-(3,4,5-trimethoxyphenyl)pyridin-4-yl]methyl]piperidine trihydrochloride:

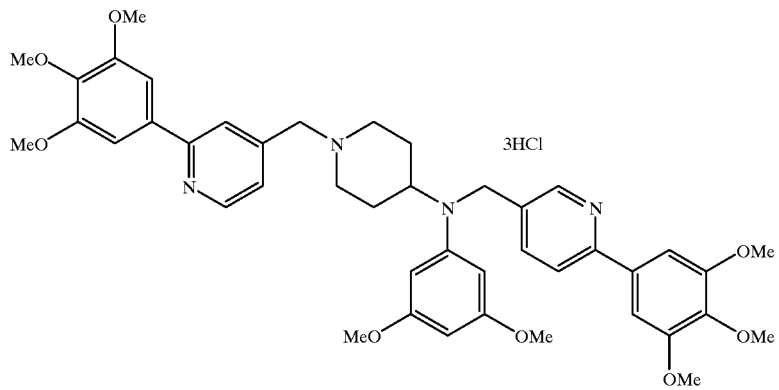

4-(3,5-Dimethoxyphenylamino)-1-[[2-(3,4,5-trimethoxyphenyl)pyridin-4-yl]methyl]piperidine (148 mg) and 5-chloromethyl-2-(3,4,5-trimethoxyphenyl)pyridine (114 mg) were condensed by the same manner as described in Example 9. Yellow oil of a free base was converted to a trihydrochloride which gave the title compound as yellow powder.

Yield: 23 mg (10%). $^1$H-NMR (400 MHz, measured as a free base, CDCl$_3$): 1.64 (br, 2H), 1.82 (br, 2H), 2.10 (br, 2H), 2.94 (br, 2H), 3.48–3.60 (m, 3H), 3.64 (s, 6H), 3.82 (s, 3H), 3.83 (s, 3H), 3.87 (s, 6H), 3.90 (s, 6H), 4.46 (s, 2H), 5.85 (br, 3H), 7.05–7.24 (m, 6H), 7.53–7.54 (m, 2H), 8.51 (s, 1H), 8.54 (br, 1H).

PREPARATION EXAMPLE 66

Synthesis of ethyl 4-(3,4,5-trimethoxyphenyl)benzoate:

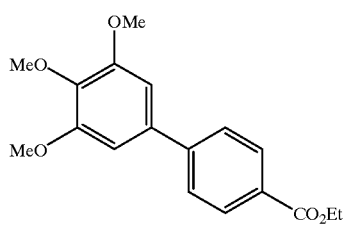

3,4,5-Trimethoxyphenylboronic acid (2.01 g) and ethyl 4-bromobenzoate (2.29 g) were condensed in the same manner as described in Preparation Example 1 to give the title compound.

Yield: 2.99 g (95%). $^1$H-NMR (400 MHz, CDCl$_3$): 1.42 (t, 3H, J=7.2 Hz), 3.90 (s, 3H), 3.94 (s, 6H), 4.38 (q, 2H, J=7.2 Hz), 6.81 (s, 2H), 7.62 (d, 2H, J=8.2 Hz), 8.10 (d, 2H, J=8.2 Hz).

PREPARATION EXAMPLE 67

Synthesis of 4-(3,4,5-trimethoxyphenyl)benzyl alcohol:

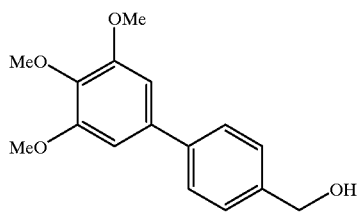

Ethyl 4-(3,4,5-trimethoxyphenyl)benzoate (2.99 g) was treated in the same manner as described in Preparation Example 2 to give the title compound.

Yield: 1.83 g (71%).

PREPARATION EXAMPLE 68

Synthesis of 4-(3,4,5-trimethoxyphenyl)benzyl chloride:

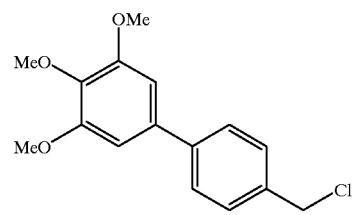

4-(3,4,5-Trimethoxyphenyl)benzyl alcohol (1.83 g) was treated in the same manner as describe in Preparation Example 3 to give the title compound.

Yield: 1.65 g (84%); $^1$H-NMR (400 MHz, CDCl$_3$): 3.90 (s, 3H), 3.93 (s, 6H), 4.65 (s, 2H), 6.77 (s, 2H), 7.46 (d, 2H, J=8.0 Hz), 7.55 (d, 2H, J=8.0 Hz).

EXAMPLE 26

Synthesis of 4-[N-(3,5-dimethoxyphenyl)-N-[[4-(3,4,5-trimethoxyphenyl)benzyl]amino]-1-[[2-(3,4,5-trimethoxyphenyl)pyridin-4-yl]methyl]piperidine dihydrochloride:

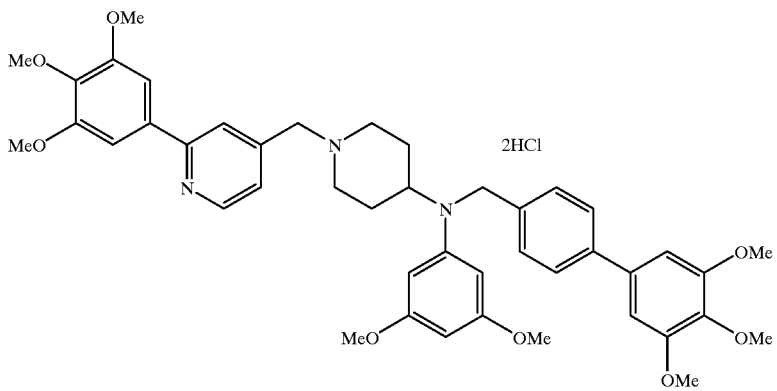

4-(3,5-Dimethoxyphenylamino)-1-[[2-(3,4,5-trimethoxyphenyl)pyridin-4-yl]methyl]piperidine (148 mg) and 4-(3,4,5-trimethoxyphenyl)benzyl chloride (114 mg) were condensed by the same manner as described in Example 9. Yellow oil of a free base was converted to a dihydrochloride which gave yellow powder of the title compound.

Yield: 35 mg (14%). $^1$H-NMR (400 MHz, measured as a free base, CDCl$_3$); 1.80–1.89 (m, 4H), 2.17 (br, 2H), 2.97 (d, 2H, J=10.5 Hz), 3.57 (s, 2H), 3.70 (s, 6H), 3.77–3.84 (m, 1H), 3.87 (s, 3H), 3.90 (s, 3H), 3.91 (s, 6H), 3.96 (s, 6H), 4.52 (s, 2H), 5.93 (s, 2H), 6.74 (s, 2H), 7.19–7.22 (m, 4H), 7.31 (d, 2H, J=8.2 Hz), 7.46 (d, 2H, J=8.2 Hz), 7.60 (s, 1H), 8.59 (d, 1H, J=5.1 Hz).

PREPARATION EXAMPLE 68

Synthesis of 4-(3,4-methylenedioxyphenylamino)-1-[[2-(3,4,5-trimethoxyphenyl)pyridin-4-yl]methyl]piperidine:

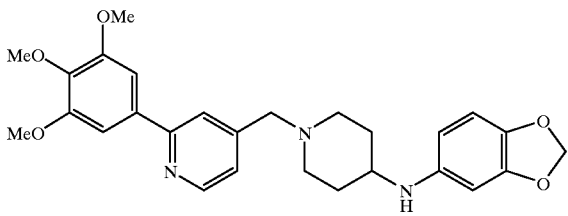

1-[[2-(3,4,5-Trimethoxyphenyl)pyridin-4-yl]methyl-4-piperidone (1.40 g) and 3,4-methylenedioxyaniline (646 mg) were treated in the same manner as described in Preparation Example 29 to give the title compound.

Yield: 810 mg (43%). $^1$H-NMR (400 MHz, CDCl$_3$): 1.63 (br, 2H), 2.02–2.60 (m, 4H), 2.80–3.15 (m, 2H), 3.25 (br, 1H), 3.70 (br, 2H), 3.88 (s, 3H), 3.96 (s, 6H), 5.83 (s, 2H), 6.02 (d, 1H, J=8.3 Hz), 6.22 (s, 1H), 6.61 (d, 1H, J=8.3 Hz), 7.18–7.28 (m, 3H), 7.64 (br, 1H), 8.60 (d, 1H, J=4.9 Hz).

EXAMPLE 27

Synthesis of 4-[N-(3,4-methylenedioxyphenyl)-N-[[2-(3,4,5-trimethoxyphenyl)pyridin-3-yl]methyl]amino]-1-[[2-(3,4,5-trimethoxyphenyl)pyridin-4-yl]methyl]piperidine trihydrochloride:

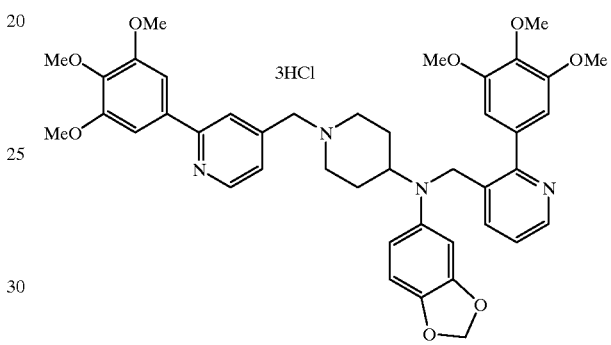

4-(3,4-Methylenedioxyphenylamino)-1-[[2-(3,4,5-trimethoxyphenyl)pyridin-4-yl]methyl]piperidine (119 mg) and 3-chloromethyl-2-(3,4,5-trimethoxyphenyl)pyridine (114 mg) were condensed in the same manner as described in Example 9. Yellow syrup obtained was converted to a trihydrochloroide to give the title compound as yellow powder.

Yield: 30 mg (14%). $^1$H-NMR (400 MHz, measured as a free base, CDCl$_3$): 1.45–2.25 (m, 6H), 2.90 (br, 2H), 3.40 (br, 1H), 3.55 (br, 2H), 3.87 (s, 3H), 3.88 (s, 9H), 3.93 (s, 6H), 4.28 (s, 2H), 5.82 (s, 2H), 6.10 (br, 1H), 6.28 (s, 1H), 6.58 (d, 1H, J=8.4 Hz), 6.67 (s, 2H), 7.12–7.30 (m, 4H), 7.52 (br, 1H), 7.75 (br, 1H), 8.51 (br, 1H), 8.57 (br, 1H).

EXAMPLE 28

Synthesis of 4-[N-(3,4-methylenedioxyphenyl)-N-[2-(3,4,5-trimethoxyphenyl)benzyl]amino]-1-[[2-(3,4,5-trimethoxyphenyl)pyridin-4-yl]methyl]piperidine dihydrochloride:

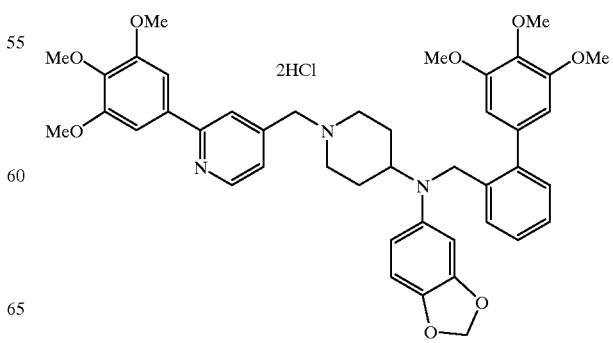

4-(3,4-Methylenedioxyphenylamino)-1-[[2-(3,4,5-trimethoxyphenyl)pyridin-4-yl]methyl]piperidine (119 mg) and 2-(3,4,5-trimethoxyphenyl)benzyl chloride (114 mg) were condensed in the same manner as described in Example 9. A free base obtained was converted to a dihydrochloroide to give the title compound as yellow powder.

Yield: 13 mg (6%). $^1$H-NMR (400 MHz, measured as a free base, CDCl$_3$): 1.61 (br, 2H), 1.78 (br, 2H), 2.10 (br, 2H), 2.91 (br, 2H), 3.50–3.54 (m, 3H), 3.87 (s, 6H), 3.90 (s, 3H), 3.92 (s, 3H), 3.99 (s, 6H), 4.26 (s, 2H), 5.82 (s, 2H), 6.12 (d, 1H, J=8.6 Hz), 6.32 (s, 1H), 6.53 (s, 2H), 6.62 (d, 1H, J=8.6 Hz), 7.17–7.26 (m, 6H), 7.42 (br, 1H), 7.55 (s, 1H), 8.58 (d, 1H, J=4.9 Hz).

EXAMPLE 29

Synthesis of 4-[N-(3,4-methylenedioxyphenyl)-N-[[2-(3,4,5-trimethoxyphenyl)pyridin-4-yl]methyl]amino]-1-[[2-(3,4,5-trimethoxyphenyl)pyridin-4-yl]methyl]piperidine trihydrochloride:

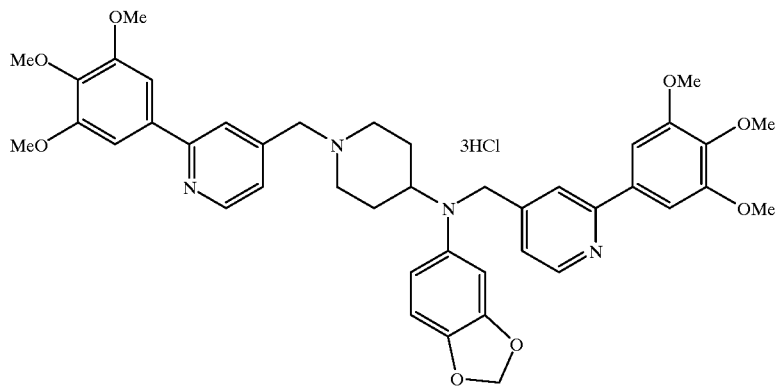

4-(3,4-Methylenedioxyphenylamino)-1-[[2-(3,4,5-trimethoxyphenyl)pyridin-4-yl]methyl]piperidine (119 mg) and 4-chloromethyl-2-(3,4,5-trimethoxyphenyl)pyridine (114 mg) were condensed by the same manner as described in Example 9. Yellow oil of a free base was converted to a trihydrochloride which gave the title compound as yellow powder.

Yield: 52 mg (25%). $^1$H-NMR (400 MHz, measured as a free base, CDCl$_3$): 1.60–1.95 (m, 4H), 2.20 (br, 2H), 3.00 (br, 2H), 3.58 (br, 3H), 3.86 (s, 3H), 3.87 (s, 3H), 3.91 (s, 6H), 3.94 (s, 6H), 4.41 (s, 2H), 5.82 (s, 2H), 6.17 (d, 1H, J=8.4 Hz), 6.39 (s, 1H), 6.62 (d, 1H, J=8.4 Hz), 7.12–7.13 (m, 3H), 7.18 (d, 1H, J=4.1 Hz), 7.23 (br, 2H), 7.54 (br, 2H), 8.51 (d, 1H, J=5.1 Hz), 8.57 (d, 1H, J=4.9 Hz).

EXAMPLE 30

Synthesis of 4-[N-(3,4-methylenedioxyphenyl)-N-[3-(3,4,5-trimethoxyphenyl)benzyl]amino]-1-[[2-(3,4,5-trimethoxyphenyl)pyridin-4-yl]methyl]piperidine dihydrochloride:

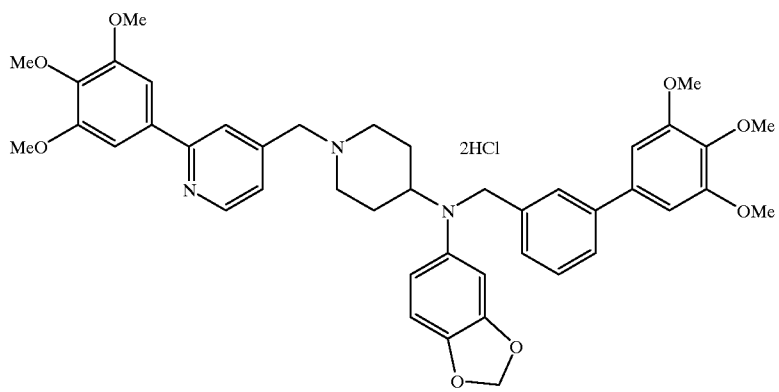

4-(3,4-Methylenedioxyphenylamino)-1-[[2-(3,4,5-trimethoxyphenyl)pyridin-4-yl]methyl]piperidine (119 mg) and 3-(3,4,5-trimethoxyphenyl)benzyl chloride (114 mg) were condensed by the same manner as described in Example 9. Yellow oil of a free base was converted to a dihydrochloride which gave the title compound as yellow powder.

Yield: 58 mg (29%). $^1$H-NMR (400 MHz, measured as a free base, CDCl$_3$): 1.60–1.97 (m, 4H), 2.15 (br, 2H), 3.00 (br, 2H), 3.58 (br, 3H), 3.86 (s, 3H), 3.88 (s, 9H), 3.94 (s, 6H), 4.43 (s, 2H), 5.81 (s, 2H), 6.21 (br, 1H), 6.42 (s, 1H), 6.62 (d, 1H, J=8.4 Hz), 6.69 (s, 2H), 7.18 (d, 1H, J=4.9 Hz), 7.22–7.39 (m, 6H), 7.60 (br, 1H), 8.57 (d, 1H, J=4.9 Hz).

EXAMPLE 31

Synthesis of 4-[N-(3,4-methylenedioxyphenyl)-N-[[2-(3,4,5-trimethoxyphenyl)pyridin-5-yl]methyl]amino]-1-[[2-(3,4,5-trimethoxyphenyl)pyridin-4-yl]methyl]piperidine trihydrochloride:

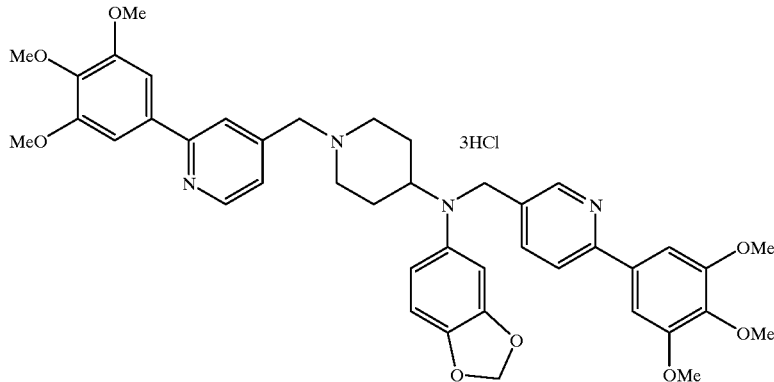

4-(3,4-Methylenedioxyphenylamino)-1-[[2-(3,4,5-trimethoxyphenyl)pyridin-4-yl]methyl]piperidine (119 mg) and 5-chloromethyl-2-(3,4,5-trimethoxyphenyl)pyridine (114 mg) were condensed by the same manner as described in Example 9. Yellow oil of a free base was converted to a trihydrochloride which gave the title compound as yellow powder.

Yield: 69 mg (27%). $^1$H-NMR (400 MHz, measured as a free base, CDCl$_3$): 1.71–1.88 (m, 4H), 2.14 (d, 2H, J=11.2 Hz), 2.97 (d, 2H, J=11.5 Hz), 3.45–3.52 (m, 1H), 3.56 (s, 2H), 3.89 (s, 3H), 3.90 (s, 3H), 3.94 (s, 6H), 3.96 (s, 6H), 4.12 (s, 2H), 5.85 (s, 2H), 6.24 (dd, 1H, J=8.5 Hz, 2.5 Hz), 6.45 (d, 1H, J=2.4 Hz), 6.64 (d, 1H, J=8.5 Hz), 7.20–7.21 (m, 1H), 7.21 (s, 2H), 7.23 (s, 2H), 7.58–7.65 (m, 3H), 8.57 (d, 1H, J=1.5 Hz), 8.59 (d, 1H, J=4.9 Hz).

EXAMPLE 32

Synthesis of 4-[N-(3,4-Methylenedioxyphenyl)-N-[4-(3,4,5-trimethoxyphenyl)benzyl]amino]-1-[[2-(3,4,5-trimethoxyphenyl)pyridin-4-yl]methyl]piperidine dihydrochloride:

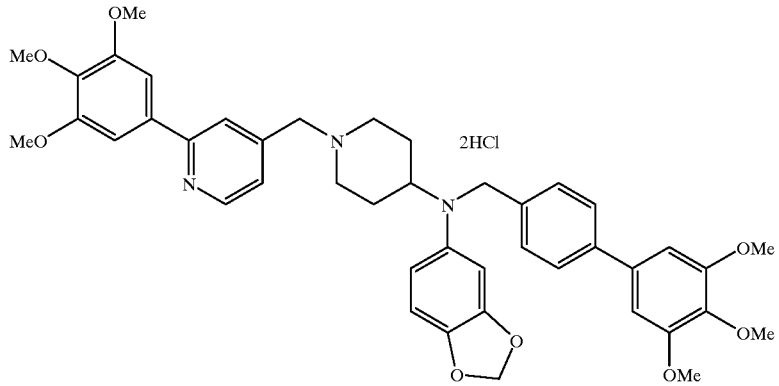

4-(3,4-Methylenedioxyphenylamino)-1-[[2-(3,4,5-trimethoxyphenyl)pyridin-4-yl]methyl]piperidine (119 mg) and 4-(3,4,5-trimethoxyphenyl)benzyl chloride (114 mg) were condensed by the same manner as described in Example 9. Yellow oil of a free base was converted to a dihydrochloride which gave the title compound as yellow powder.

Yield: 29 mg (14%). $^1$H-NMR (400 MHz, measured as a free base, CDCl$_3$); 1.62–2.00 (m, 4H), 2.20 (br, 2H), 2.99 (br, 2H), 3.58 (br, 3H), 3.86 (s, 3H), 3.87 (s, 3H), 3.88 (s, 6H), 3.89 (s, 6H), 4.41 (s, 2H), 5.82 (s, 2H), 6.19 (d, 1H, J=8.6 Hz), 6.39 (s, 1H), 6.63 (d, 1H, J=8.4 Hz), 6.72 (s, 2H), 7.18 (d, 1H, J=5.1 Hz), 7.23 (s, 2H), 7.29 (d, 2H, J=8.0 Hz), 7.43 (d, 2H, J=8.2 Hz), 7.60 (br, 1H), 8.57 (d, 1H, J=4.9 Hz).

TEST EXAMPLE 1

(Inhibitory effect on cell adhesion)

The test was conducted by reference to the method by Ross et al. (J. Biol. Chem., 267, 8537–8543 (1992)). More specifically, after human umbilical venous endothelial cells (HUVEC) were cultured on a 48-well plate to confluent growth, TNF a was added thereto. Upon elapsed time of 5 hours after the addition, U937, which was a human monocytic/histocytic cell fluorescence-labeled with PKH2 (product of Sigma-Aldrich Co., Ltd.), was added in a proportion of $1\times10^6$ cells per well. After the plate was left at rest at room temperature for 1 hour, unadhered U937 was washed out and lysed in 1% Triton X-100 to measure a remaining fluorescence intensity (excitation wavelength: 480 nm; measuring wavelength: 530 nm). HUVEC and U937 were cultured in EGM-2 (product of Sanko Junyaku K. K.) and 10% FCS-containing RPMI1640, respectively. Each test agent was added to HUVEC upon the addition of TNFα and to U937 24 hours prior to the cell adhesion test. The inhibitory activity was calculated out as $IC_{50}$ value after inhibitory ratio at each concentration of test compounds was determined. The inhibitory ratio was calculated according to the by equation [(C−B)/(A−B)×100 (%)], wherein A is the number of U937 cells adhered to HUVEC stimulated by TNFα when no test agent was added, B is the number of U937 cells adhered to HUVEC not stimulated by TNFα when no test agent was added, and C is the number of U937 cells adhered to HUVEC stimulated by TNFα when the test agent was added. The results are shown in Table 1. As control compounds, Test Compound 1 described in Japanese Patent Application Laid-Open No. 9-143075 and dilazep described in Japanese Patent Application Laid-Open No. 11-92382 were simultaneously evaluated.

| Example | $IC_{50}$ (μM) |
| --- | --- |
| 3 | 0.3 |
| 5 | 0.2 |
| 7 | 0.3 |
| 10 | 0.04 |
| 13 | 0.03 |
| 16 | 0.3 |
| 19 | 0.3 |
| 23 | 0.03 |
| 29 | 0.03 |
| Test compound 1 | 10 |
| Dilazep | >10 |

Specific formulation examples will hereinafter be described.

| Preparation Example 33: (Capsule preparation) | |
| --- | --- |
| Compound obtained by Example 13 | 30 mg |
| Microcrystalline cellulose | 30 mg |
| Lactose | 57 mg |
| Magnesium stearate | 3 mg |
| Total amount | 120 mg. |

The above ingredients were mixed in accordance with a method known per se in the art and then charged in capsules to obtain capsule preparations.

| Preparation Example 34: (Tablet preparation) | |
| --- | --- |
| Compound obtained by Example 13 | 30 mg |
| Starch | 44 mg |
| Starch (for glue) | 5.6 mg |
| Magnesium stearate | 0.4 mg |
| Calcium carboxymethyl cellulose | 20 mg |
| Total amount | 100 mg. |

The above ingredients were mixed in accordance with a method known per se in the art to obtain tablet preparations.

PREPARATION EXAMPLE 35
(Injection preparation)
Compound obtained by Example 13(100 mg) and sodium chloride (900 mg) were dissolved in distilled water (about 80 mL) for injection, and distilled water for injection was added to the resultant solution to 100 mL in total. This diluted solution was sterilized by filtration and then subdivided and charged into 10 ampoules, and the ampoules were sealed to obtain injection preparations.

As described above, the compounds (1) according to the present invention have inhibitory effects on both cell adhesion and cell infiltration and are useful as medicines for prevention or treatment of allergy, asthma, rheumatism, arteriosclerosis, inflammatory, Sjogren's syndrome, etc.

Obviously, numerous modifications of the above teachings are apparent to those skilled in the art. Therefore, within the scope of the appended claims the invention may be practiced otherwise than as specifically described herein.

What is claimed is:

1. A cyclic amine compound represented by the following general formula (1):

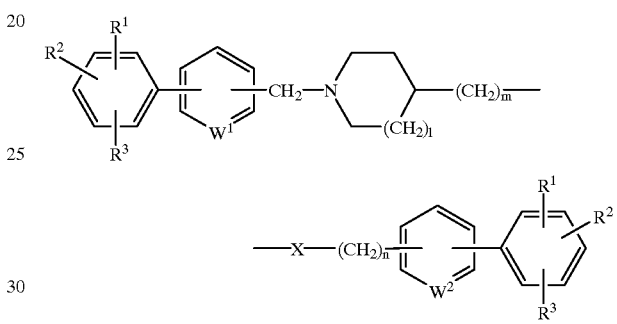

wherein,
$R^1$, $R^2$ and $R^3$ each independently represent a hydrogen atom, a halogen atom, or a hydroxy, alkyl, halogen-substituted alkyl, alkoxy, alkylthio, carboxyl, alkoxycarbonyl or alkanoyl group;
$W^1$ and $W^2$ each independently represent N or CH;
X represents O, $NR^4$, $CONR^4$ or $NR^4CO$;
$R^4$ each independently represents a hydrogen atom, or an alkyl, alkenyl, alkynyl, substituted or unsubstituted aryl, substituted or unsubstituted heteroaryl, substituted or unsubstituted aralkyl, or substituted or unsubstituted heteroaralkyl group; and
l, m and n are a number of 0 or 1,
as well as a salt thereof and a hydrate thereof.

2. The compound according to claim 1, wherein $R^1$, $R^2$ and $R^3$ each independently represent a hydrogen atom, a halogen atom, or a hydroxy, $C_1$–$C_8$ alkyl, halogen-substituted $C_1$–$C_8$ alkyl, $C_1$–$C_8$ alkoxy, $C_1$–$C_8$ alkylthio, carboxyl, $C_1$–$C_6$ alkoxycarbonyl or $C_1$–$C_6$ alkanoyl group.

3. The compound according to claim 1, wherein $R^4$ each independently represents a hydrogen atom, a $C_1$–$C_8$ alkyl group, a $C_3$–$C_8$ alkenyl group, a $C_3$–$C_8$ alkynyl group, a substituted or unsubstituted $C_6$–$C_{14}$ aryl group, a substituted or unsubstituted 5- or 6-membered ring heteroaryl group containing 1 to 4 nitrogen atoms, a substituted or unsubstituted $C_6$–$C_{14}$ aryl—$C_1$–$C_6$ alkyl group, or a substituted or unsubstituted 5- or 6-membered ring, 1 to 4 nitrogen atoms-containing heteroaryl—$C_1$–$C_6$ alkyl group.

4. The compound according to claim 1, wherein the substituent(s) of aryl, aralkyl, heteroaryl or heteroaralkyl group representing $R^4$ are 1 to 3 groups or atoms selected from alkyl, alkoxy, halogen-substituted alkoxy, alkylthio, halogen, nitro, amino, acetylamino, trifluoromethyl and alkylenedioxy.

5. The compound according to claim 1, wherein X represents $NR^4$, and $R^4$ represents a substituted or unsubstituted $C_6$–$C_{14}$ aryl group or a substituted or unsubstituted 5- or 6-membered ring heteroaryl group containing 1 to 4 nitrogen atoms in the ring.

6. A pharmaceutical composition which comprises as an active ingredient a cyclic amine compound represented by the following general formula (1):

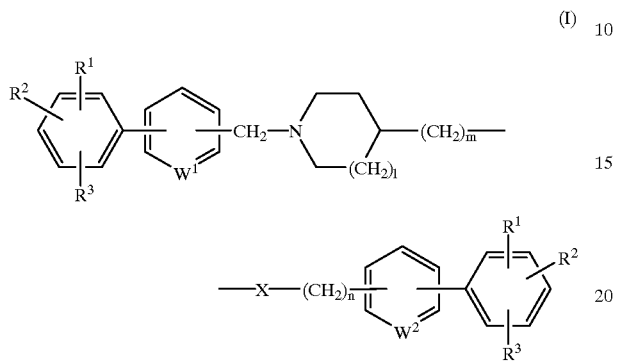

(I)

wherein,
- $R^1$, $R^2$ and $R^3$ each independently represent a hydrogen atom, a halogen atom, or a hydroxy, alkyl, halogen-substituted alkyl, alkoxy, alkylthio, carboxyl, alkoxycarbonyl or alkanoyl group;
- $W^1$ and $W^2$ each independently represent N or CH;
- X represents O, $NR^4$, $CONR^4$ or $NR^4CO$;
- $R^4$ each independently represents a hydrogen atom, or an alkyl, alkenyl, alkynyl, substituted or unsubstituted aryl, substituted or unsubstituted heteroaryl, substituted or unsubstituted aralkyl, or substituted or unsubstituted heteroaralkyl group; and
- l, m and n are a number of 0 or 1, a salt thereof or a hydrate thereof, and a pharmaceutical acceptable carrier.

7. The pharmaceutical composition according to claim 6, wherein $R^1$, $R^2$ and $R^3$ each independently represent a hydrogen atom, a halogen atom, or a hydroxy, $C_1$–$C_8$ alkyl, halogen-substituted $C_1$–$C_8$ alkyl, $C_1$–$C_8$ alkoxy, $C_1$–$C_8$ alkylthio, carboxyl, $C_1$–$C_6$ alkoxycarbonyl or $C_1$–$C_6$ alkanoyl group.

8. The pharmaceutical composition according to claim 6, wherein $R^4$ each independently represents a hydrogen atom, a $C_1$–$C_8$ alkyl group, a $C_3$–$C_8$ alkenyl group, a $C_3$–$C_8$ alkynyl group, a substituted or unsubstituted $C_6$–$C_{14}$ aryl group, a substituted or unsubstituted 5- or 6-membered ring heteroaryl group containing 1 to 4 nitrogen atoms, a substituted or unsubstituted $C_6$–$C_{14}$ aryl—$C_1$–$C_6$ alkyl group, or a substituted or unsubstituted 5- or 6-membered ring, 1 to 4 nitrogen atoms-containing heteroaryl—$C_1$–$C_6$ alkyl group.

9. The pharmaceutical composition according to claim 6, wherein the substituent(s) of aryl, aralkyl, heteroaryl or heteroaralkyl group representing $R^4$ are 1 to 3 groups or atoms selected from alkyl, alkoxy, halogen-substituted alkoxy, alkylthio, halogen, nitro, amino, acetylamino, trifluoromethyl and alkylenedioxy.

10. The pharmaceutical composition according to claim 6, wherein X represents $NR^4$, and $R^4$ represents a substituted or unsubstituted $C_6$–$C_{14}$ aryl group or a substituted or unsubstituted 5- or 6-membered ring heteroaryl group containing 1 to 4 nitrogen atoms in the ring.

11. The pharmaceutical composition according to claim 6 comprising said active ingredient in an amount effective for treating a disease caused by cell adhesion and/or cell infiltration.

12. The pharmaceutical composition according to claim 11, wherein said disease is selected from allergy, asthma, inflammation, rheumatic disease, arteriosclerosis and Sjogren's syndrome.

13. A method for treating a disease caused by cell adhesion and/or cell infiltration, which comprises administering an effective amount of a cyclic amine compound represented by the following general formula (1):

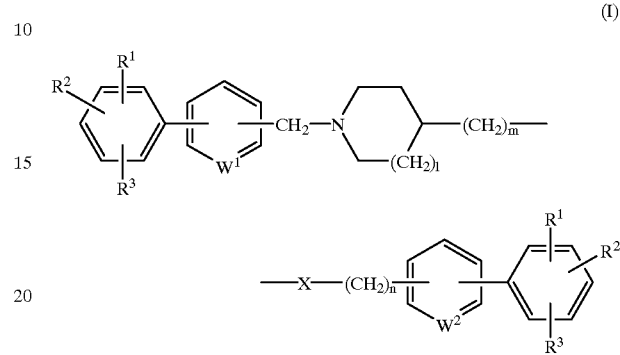

(I)

wherein,
- $R^1$, $R^2$ and $R^3$ each independently represent a hydrogen atom, a halogen atom, or a hydroxy, alkyl, halogen-substituted alkyl, alkoxy, alkylthio, carboxyl, alkoxycarbonyl or alkanoyl group;
- $W^1$ and $W^2$ each independently represent N or CH;
- X represents O, $NR^4$, $CONR^4$ or $NR^4CO$;
- $R^4$ each independently represents a hydrogen atom, or an alkyl, alkenyl, alkynyl, substituted or unsubstituted aryl, substituted or unsubstituted heteroaryl, substituted or unsubstituted aralkyl, or substituted or unsubstituted heteroaralkyl group; and
- l, m and n are a number of 0 or 1, a salt thereof or a hydrate thereof, to a patient who requires such treatment.

14. The method according to claim 13, wherein $R^1$, $R^2$ and $R^3$ each independently represent a hydrogen atom, a halogen atom, or a hydroxy, $C_1$–$C_8$ alkyl, halogen-substituted $C_1$–$C_8$ alkyl, $C_1$–$C_8$ alkoxy, $C_1$–$C_8$ alkylthio, carboxyl, $C_1$–$C_6$ alkoxycarbonyl or $C_1$–$C_6$ alkanoyl group.

15. The method according to claim 13, wherein $R^4$ each independently represent a hydrogen atom, a $C_1$–$C_8$ alkyl group, a $C_3$–$C_8$ alkenyl group, a $C_3$–$C_8$ alkynyl group, a substituted or unsubstituted $C_6$–$C_{14}$ aryl group, a substituted or unsubstituted 5- or 6-membered ring heteroaryl group containing 1 to 4 nitrogen atoms, a substituted or unsubstituted $C_6$–$C_{14}$ aryl—$C_1$–$C_6$ alkyl group, or a substituted or unsubstituted 5- or 6-membered ring 1 to 4 nitrogen atoms-containing heteroaryl—$C_1$–$C_6$ alkyl group.

16. The method according to claim 13, wherein the substituent(s) of aryl, aralkyl, heteroaryl or heteroaralkyl group representing $R^4$ are 1 to 3 groups or atoms selected from alkyl, alkoxy, halogen-substituted alkoxy, alkylthio, halogen, nitro, amino, acetylamino, trifluoromethyl and alkylenedioxy.

17. The method according to claim 13, wherein X represents $NR^4$, and $R^4$ represents a substituted or unsubstituted $C_6$–$C_{14}$ aryl group or a substituted or unsubstituted 5- or 6-membered ring heteroaryl group containing 1 to 4 nitrogen atoms in the ring.

18. The method according to claim 13, wherein said disease is selected from allergy, asthma, inflammation, rheumatic disease, arteriosclerosis and Sjogren's syndrome.

* * * * *

UNITED STATES PATENT AND TRADEMARK OFFICE
CERTIFICATE OF CORRECTION

PATENT NO. : 6,395,753 B1
DATED : May 28, 2002
INVENTOR(S) : Tatsuhiko Kodama et al.

It is certified that error appears in the above-identified patent and that said Letters Patent is hereby corrected as shown below:

Column 3,
Line 27, "$R^4$ each independently represents" should read -- $R^4$ represents --.

Column 4,
Lines 6 and 12, "ethyoxy" should read -- ethoxy --.

Column 8,
Line 33, "X=$NR^4$ and $R^4$" should read -- X=$NR^4$ CO and $R^4$ --.

Column 25,
Line 29, "1-[2-[(3,4,5-" should read -- 1[[2-(3,4,5 --.

Column 40,
Lines 13 and 14, "2-(4-chloro-3,5-dimethoxphenyl)" should read -- 2-(4-chloro-3,5-dimethoxphenyl)-4-chloromethyl --.

Column 41,
Line 54, "-4-yl]methyl-4-" should read -- -4-yl]methy]-4- --.

Column 45,
Line 26, "-amino]-" should read -- amino]- --.

Column 47,
Line 19, "-(3,4,5-trimethoxpheny)pyridine-" should read -- -(3,4,5-trimethoxphenyl)pyridine --.

UNITED STATES PATENT AND TRADEMARK OFFICE
CERTIFICATE OF CORRECTION

PATENT NO.   : 6,395,735 B1
DATED        : May 28, 2002
INVENTOR(S)  : Tatsuhiko Kodama et al.

It is certified that error appears in the above-identified patent and that said Letters Patent is hereby corrected as shown below:

Column 66,
Line 64, "-[[4-(3,4,5-" should read -- -[4-(3,4,5- --.

Signed and Sealed this

Thirty-first Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,395,753 B1                                        Page 1 of 1
DATED         : May 28, 2002
INVENTOR(S)   : Tatsuhiko Kodama et al.

It is certified that error appears in the above-identified patent and that said Letters Patent is hereby corrected as shown below:

<u>Column 36,</u>
Lines 30-40,

"
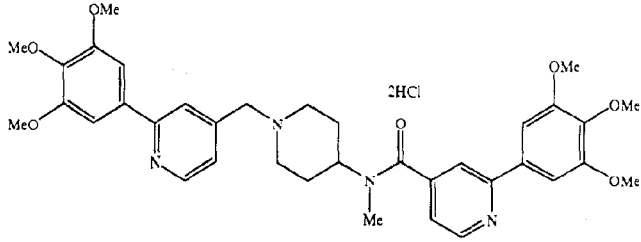
"

should read --
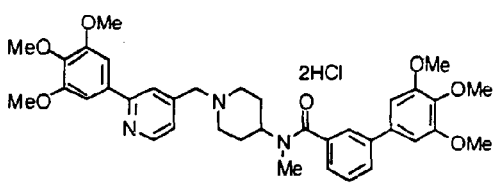
--

Signed and Sealed this

Thirteenth Day of May, 2003

JAMES E. ROGAN
*Director of the United States Patent and Trademark Office*